United States Patent
Fu et al.

(10) Patent No.: US 11,420,936 B2
(45) Date of Patent: Aug. 23, 2022

(54) HYPOXIA INDUCIBLE FACTOR-2(ALPHA) INHIBITORS AND THEIR USE IN THE TREATMENT OF DISEASES

(71) Applicant: NIKANG THERAPEUTICS, INC., Wilmington, DE (US)

(72) Inventors: Jiping Fu, Danville, CA (US); Yan Lou, Pleasanton, CA (US); Yigang He, Newark, DE (US)

(73) Assignee: NIKANG THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 17/686,385

(22) Filed: Mar. 3, 2022

(65) Prior Publication Data

US 2022/0185771 A1 Jun. 16, 2022

Related U.S. Application Data

(63) Continuation of application No. PCT/US2021/027811, filed on Apr. 16, 2021, which is a continuation-in-part of application No. 16/851,018, filed on Apr. 16, 2020, now abandoned.

(60) Provisional application No. 63/093,734, filed on Oct. 19, 2020.

(51) Int. Cl.
  *C07C 255/54* (2006.01)
  *A61P 35/00* (2006.01)

(52) U.S. Cl.
  CPC ............ *C07C 255/54* (2013.01); *A61P 35/00* (2018.01); *C07C 2603/10* (2017.05)

(58) Field of Classification Search
  CPC ..... C07C 255/54; C07C 2603/10; A61P 35/00
  USPC ........................................................ 514/646
  See application file for complete search history.

(56) References Cited

U.S. PATENT DOCUMENTS

| 6,133,279 | A | 10/2000 | Cynshi et al. |
|---|---|---|---|
| 9,908,845 | B2 | 3/2018 | Dixon et al. |
| 10,098,878 | B2 | 10/2018 | Bruick et al. |
| 10,155,726 | B2 | 12/2018 | Wehn et al. |
| 10,278,942 | B2 | 5/2019 | Josey et al. |
| 11,267,782 | B2 | 3/2022 | Fu et al. |
| 2012/0316204 | A1 | 12/2012 | Shalwitz et al. |
| 2016/0362390 | A1 | 12/2016 | Wehn et al. |
| 2019/0048421 | A1 | 2/2019 | Kim et al. |
| 2019/0282535 | A1 | 9/2019 | Josey et al. |
| 2022/0162158 | A1 | 5/2022 | Fu et al. |

FOREIGN PATENT DOCUMENTS

| WO | WO 2006/094292 A2 | 9/2006 |
|---|---|---|
| WO | WO 2015/035223 A1 | 3/2015 |
| WO | WO 2015/095048 A1 | 6/2015 |
| WO | WO 2016/144825 A1 | 9/2016 |
| WO | WO 2018/031680 A1 | 2/2018 |
| WO | WO 2019/191227 A1 | 10/2019 |
| WO | WO 2020/055883 A1 | 3/2020 |
| WO | WO 2020/081695 A1 | 4/2020 |
| WO | WO 2020/214853 A1 | 10/2020 |
| WO | WO 2021/016280 A1 | 1/2021 |

OTHER PUBLICATIONS

International Search Report and Written Opinion of PCT/US2021/027811 dated Jun. 21, 2021, 13 pages.
International Search Report and Written Opinion of PCT/US2020/028579 dated Aug. 3, 2020, 10 pages.
Renal-Cancer-Cure, 2021, https://www.cancer.gov/types/kidney/hp/kidney-treatment-pdg#::text=Renal%20cell%20cancer%2C%20also%20called,or%20degree%20of%20tunnor%20dissennination.
Renal-Cancer-Prevention, 2021, https://www.cancer.org/cancer/kidney-cancer/causes-risksprevention/prevention.htnnl.
Renal-Carcinoma, 2021, https://ascopost.conn/news/february-2020/oral-hif2a-inhibitor-for-advanced-clear-cell-renal-cell-carcinonna/.
Wehn et al., "Design and Activity of Specific Hypoxia-Inducible Factor 2# (HIF-2#) Inhibitors for the Treatment of Clear Cell Renal Cell Carcinoma: Discovery of Clinical Candidate (S)-3-((2,2-difluoro-1-hydroxy-7-(methylsulfonyl)-2,3-dihydro-1H-inden-4-yl)oxy)-5-fluorobenzonitrile (PT2385)", J. Med. Chem., DOI: 10.1021/acs.jmedchem.8b01196 Publication Date (Web): Oct. 5, 2018.
Xu et al., "3-[(1S,2S,3R)-2,3-Difluoro-1-hydroxy-7-methylsulfonyl-indan-4-yl]oxy-5-fluoro-benzonitrile (PT2977), a Hypoxia-Inducible Factor 2# (HIF-2#) Inhibitor for the Treatment of Clear Cell Renal Cell Carcinoma", J. Med. Chem., DOI: 10.1021/acs.jmedchem.9b00719, Publication Date (Web): Jun. 24, 2019.

*Primary Examiner* — Ana Z Muresan
(74) *Attorney, Agent, or Firm* — Squire Patton Boggs (US) LLP

(57) ABSTRACT

The present disclosure is directed certain Hypoxia Inducible Factor 2α (HIF-2α) inhibitors and their use in the treatment of diseases mediated by HIF-2α such as cancer. Also provided is the use of HIF-2α inhibitors in combination with a poly (ADP-ribose) polymerase (PARP) inhibitor. In particular, the present disclosure is directed to methods for the treatment of cancers using a HIF-2α inhibitor in combination with a PARP inhibitor and pharmaceutical compositions comprising the same.

15 Claims, 1 Drawing Sheet

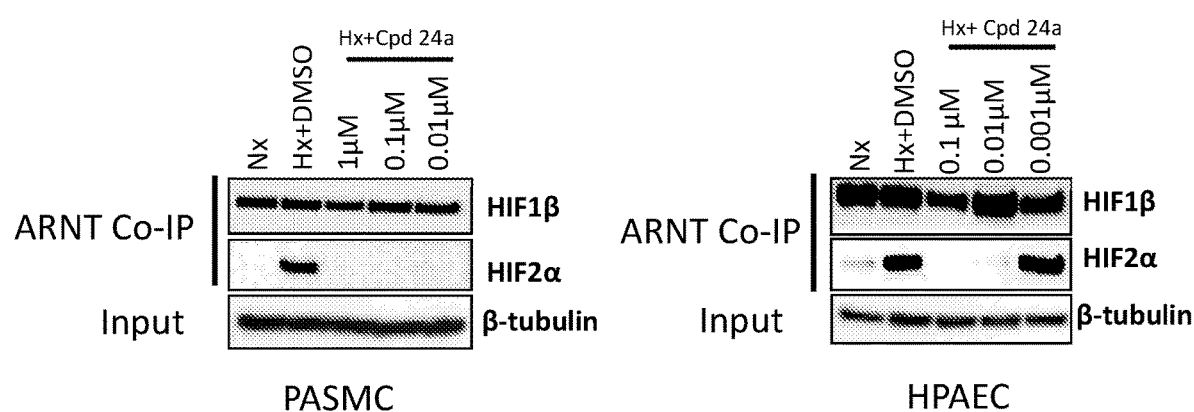
Nx: Normoxia; Hx: Hypoxia; Co-IP: Co-immunoprecipitation

HYPOXIA INDUCIBLE FACTOR-2(ALPHA) INHIBITORS AND THEIR USE IN THE TREATMENT OF DISEASES

CROSS-REFERENCE TO RELATED APPLICATIONS

This application is a continuation of PCT International Application No. PCT/US2021/027811, filed on Apr. 16, 2021, which is a continuation-in-part of and claims priority to, and the benefit of, U.S. nonprovisional application Ser. No. 16/851,018, filed Apr. 16, 2020, and PCT/US2021/027811, filed on Apr. 16, 2021, claims priority to, and the benefit of, U.S. Provisional application no. 63/093,734, filed Oct. 19, 2020, and the contents of all of which are hereby incorporated by reference in their entireties.

FIELD OF THE DISCLOSURE

The present disclosure is directed certain Hypoxia Inducible Factor 2α (HIF-2α) inhibitors and their use in the treatment of diseases mediated by HIF-2α such as cancer. Also provided is the use of HIF-2α inhibitors in combination with a poly (ADP-ribose) polymerase (PARP) inhibitor. In particular, the present disclosure is directed to methods for the treatment of cancers using a HIF-2α inhibitor in combination with a PARP inhibitor and pharmaceutical compositions comprising the same.

BACKGROUND

Hypoxia is a characteristic feature of solid tumors and the adaptation of cancer cells to hypoxia is instrumental in the development of aggressive phenotype and associated with poor prognostic in cancer patients. The cellular response to hypoxia is governed largely by a family of transcription factors known as Hypoxia Inducible Factors (HIFs), including HIF-1α, HIF-2α and HIF-3α (see Wang, G. L., et al. (1995), Proc Natl Acad Sci USA, 92(12), 5510-5514; Tian, H., et al. (1997), Genes Dev, 11(1), 72-82; and Gu, Y. Z., et al. (1998), Gene Expr, 7(3), 205-213). In sufficiently oxygenated cells, HIFα subunits are hydroxylated by prolyl-4-hydroxylases, and then polyubiquitinated by Von Hippel Lindau (VHL) E3 ubiquitin ligase complex, followed by proteasome mediated degradation (see Bishop, T., et al. (2014), Hypoxia (Auckl), 2, 197-213). Under hypoxia condition, the hydroxylation on HIFαs is inhibited, resulting in the stabilization and accumulation of HIFα in the nucleus, where they dimerize with HIF-1β and regulates the transcription of a large panel of target genes (see Greer, S. N., et al. (2012), EMBO J, 31(11), 2448-2460). This allows the coordinated activation of genes essential in the adaptive response to hypoxia including genes important for angiogenesis, metabolic reprogramming, survival, proliferation, and metastasis.

Angiogenesis genes increased by HIF transcriptional complex in response to hypoxia include VEGF, FLT-1, ANG1, ANG2, TIE2, PDGF, MMP2, 9 and FLK1 (see Favaro, E., et al. (2011), Genome Med, 3(8), 55; and Semenza, G. L. (2014), Annu Rev Pathol, 9, 47-71). The importance of tumor angiogenesis in driving tumor progression has been validated by the clinical benefit of both VEGFR inhibitors and anti-VEGF antibodies in multiple types of cancers, including colorectal cancer, glioblastoma, hepatocellular carcinoma, renal cell carcinoma, thyroid cancer, and neuroendocrine cancers. Despite initial response to anti-VEGF pathway treatment, many patients develop resistance mechanism(s) and become refractory. Important resistance mechanisms to anti-angiogenic therapy include HIF mediated up-regulation of alternative pro-angiogenic factors, and metabolic reprogramming (see Bergers, G., & Hanahan, D. (2008), Nat Rev Cancer, 8(8), 592-603; Welti, J., et al. (2013), J Clin Invest, 123(8), 3190-3200). Thus, targeting HIF represents an alternative strategy to targeting VEGF or VEGFR directly.

HIF-1α and HIF-2α are the best characterized HIFα subunits with HIF-2α being recognized as a critical oncogenic driver in clear cell renal cell carcinoma (ccRCC), which often constitutively expresses HIF-2α due to the high frequency of functional deficiency in VHL (up to 90%) as a result of either genetic inactivation VHL gene or its promoter hypermethylation (see Network, C. G. A. R. (2013), Nature, 499(7456), 43-49; Sato, Y., et al. (2013), Nat Genet, 45(8), 860-867; Melendez-Rodriguez, F., et al. (2018), Front Oncol, 8, 214; Rathmell, W. K., & Chen, S. (2008), Expert Rev Anticancer Ther, 8(1), 63-73). Pre-clinical and clinical data have demonstrated that pharmacological inhibitors of HIF-2α can efficiently combat ccRCC growth (see Wallace, E. M., et al. (2016), Cancer Res, 76(18), 5491-5500; Courtney, K. D., et al. (2018), J Clin Oncol, 36(9), 867-874; and Choueiri, T. K., et al. (2020), ASCO).

Poly(ADP-ribose)polymerase-1 (PARP1) is an enzyme highly expressed in the nuclei of mammalian cells and plays an important role in repairing damaged DNA and maintaining genomic stability. PARP functions to detect and initiate cellular response to metabolic, chemical, or radiation-induced single-strand DNA breaks (SSB) by synthesis of a polymeric adenosine diphosphate ribose (poly (ADP-ribose) or PAR) chain and subsequently signaling a complex enzymatic machinery, including DNA-repairing enzymes DNA ligase III (LigIII), DNA polymerase beta (polβ), and scaffolding proteins such as X-ray cross-complementing gene 1 (XRCC1), to repair these SSB (see Dulaney, C., et al. (2017), Semin Cell Dev Biol, 63, 144-153; and Morales, J., et al. (2014), Crit Rev Eukaryot Gene Expr, 24(1), 15-28). When PARP activity is impaired, such as when inhibited by a PARP inhibitor, SSB will eventually progress to double strand breaks (DSBs) that can be highly toxic to the cell (see Dulaney, C., et al. (2017), Semin Cell Dev Biol, 63, 144-153). DSB can be repaired by the homologous recombination (HR) machinery (see Li, X., & Heyer, W. D. (2008), Cell Res, 18(1), 99-113). Tumors lacking the ability to repair DSBs, i.e. those with mutations in BRCA1/2 genes, key components of HR pathway, are particularly sensitive to PARP inhibitors (see Slade, D. (2020), Genes Dev, 34(5-6), 360-394). This synthetic lethality has been validated both preclinically, and clinically by the approval of PARP inhibitors in BRCA1/2-deficient ovarian, fallopian tube, or primary peritoneal cancer and breast cancer (see Yi et al., et al. (2019), Exp Hematol Oncol, 8, 29; and Slade, D. (2020), Genes Dev, 34(5-6), 360-394). Additionally, PARP inhibitors such as veliparib is currently being tested in clinical trials in various cancer settings, including renal cell carcinoma (RCC).

RCC is not commonly associated with genetic alterations in the HR pathways, such as BRCA1/2 mutations, but exhibits a "BRCAness" phenotype (see Warsow et al., et al. (2018), Sci Rep, 8(1), 7477). "BRCAness" is a term specifically coined to describe tumors with a defect in DNA double-strand break repair by homologous recombination in the absence of BRCA1 or BRCA2 mutations (see Turner, N., et al. (2004), Nat Rev Cancer, 4(10), 814-819). Recently, VHL-deficient RCC has been shown to share some features with "BRCAness" tumors (see Scanlon, S. E., et al. (2018), Oncotarget, 9(4), 4647-4660). An analysis of the Cancer Genome Atlas (TCGA) ccRCC database for DNA repair gene expression in VHL-deficient and VHL-WT renal tumor samples identified a correlation between VHL inactivation and reduced expression of homologous recombination pathway genes including ANCD2, BRCA1, RAD51 (see Scanlon, S. E., et al. (2018), Oncotarget, 9(4), 4647-4660). Thus, VHL deficient ccRCC, may exhibit higher sensitivity to PARP inhibitors than normal tissues do.

In addition, it has been found that hypoxia can lead to the down regulation of BRCA1 expression, thus resulting in decreased homologous recombination activity which is important in mediating sensitivity to PARP inhibitors (see Bindra, R. S., et al. (2005), Cancer Res, 65(24), 11597-11604). Since one of the key mechanisms by which HIF-2α inhibition works is by creating hypoxic conditions in tumor tissues, administration of a HIF-2α inhibitor with a PARP inhibitor should cause reduction of important genes in HR pathway, thereby providing greater therapeutic effect in suppressing ccRCC tumor progression or inducing ccRCC tumor regression.

In addition to VHL deficiency, ccRCC tumors exhibit frequent mutation or deletion in many genes with known function in chromatin remodeling and DNA damage response. PBRM1, the second most commonly mutated gene in ccRCC, regardless of stages, encodes BRG1-associated factor (BAF) 180, the defining subunit of the ~2 MDa Polybromo BAF (PBAF) SWI/SNF complex that functions to modulate chromatin structure (see Hsieh et al., et al. (2017), Eur Urol, 71(3), 405-414; and Varela et al., et al. (2011), Nature, 469(7331), 539-542). Other frequently altered genes in ccRCC, including SETD2 (a histone methyltransferase), KDMSC (a demethylase) and BAP1 (a deubiquitinating enzyme) are also implicated in chromatin remodeling and genomic stability (see Mehdi, A., & Riazalhosseini, Y. (2017), Int J Mol Sci, 18(8)). These deficiencies could also be exploited for treatment with a PARP inhibitor by inducing excessive genome instability and catastrophic DNA damage. For example, it is recently found that ccRCC cells with PBRM1 deficiency are more sensitive to PARP inhibitor treatment (see Chabanon, R. M., et al. (2020), AACR). Thus, combination of HIF-2α inhibitor with PARP inhibitor may significantly improve clinical benefit by targeting different key oncogenic pathways in ccRCC.

HIF-2α overexpression has also been found in multiple tumor types, including renal cell carcinoma (RCC) beyond clear cell subtype such as papillary RCC tumor model, breast, brain, bladder, cartilage, cervix, colorectal, endometrial, head and neck, kidney, liver, lung, ovarian, pancreas, prostate, salivary glands, skin, soft tissues and stomach cancer (see Wong, S. C., et al. (2018), Mol Cancer Ther, 17(1), 140-149; Moreno Roig, E., et al. (2018), Front Oncol, 8, 224; and Luo, D., et al. (2019), Cancer Epidemiol Biomarkers Prev, 28(5), 857-866). It is widely accepted that in tumors, especially large and fast-growing tumor tissue, oxygen demand is surpassed by oxygen supply. Thus, there is a heterogeneous hypoxic microenvironment within the tumor tissue, with increasingly severe hypoxia correlating with the distance of tumor cells from existing vasculature, due to hampered oxygen diffusion. This phenomenon has been observed in almost all solid tumor types and drives the stabilization and accumulation of HIF-1α, and/or HIF-2α, which in turn to promote new blood vessels development to boost oxygen and nutrients supplies for tumor growth. Since inhibition of HIF-2α would aggravate the hypoxic condition that may subsequently both increase DNA damage and decrease DNA repair capacity, creating a vulnerability that can be exploited by combination treatment with an HIF-2α inhibitor and a PARP inhibitor in these cancers.

Despite the promise of PARP inhibitor in the clinic, many patients do not respond or develop resistance after initial response. Certain tumor cells are known to possess cancer stem cell (CSC)-like features, which mediate resistance to targeted therapeutics and traditional chemotherapy in many tumor types (see Phi, L. T. H., et al. (2018), Stem Cells Int, 2018, 5416923). HIF-2α has been found to modulate cancer stem cell features in multiple tumor types, including glioblastoma, acute lymphocytic leukemia, acute myeloid leukemia, chronic myeloid leukemia, and breast cancer (see Peng, G., & Liu, Y. (2015), Trends Pharmacol Sci, 36(6), 374-383). Indeed, HIF-2α silencing in glioblastoma decreases self-renewal, tumor cell proliferation in vitro, and tumor-initiating capacity in vivo (see Nusblat, L. M., et al. (2020), Cancer Drug Resist, 3(2), 199-208). Thus, HIF-2α activity may also play a role in mediating resistance to PARP inhibitors in patients by upregulating cancer stem cell-like properties. A combination of HIF-2α inhibitor and PARP inhibitor may be synergistic and may represent a new paradigm in treating cancer types, in which PARP inhibitors have been approved, or are currently undergoing clinical development.

Because of the roles of HIF-α proteins in regulating physiological response to the change of oxygen levels, they have been causally associated with many hypoxia-related pathological processes in addition to cancer. Inflammatory bowel disease (IBD) is a chronic relapsing inflammatory disease of the intestine. Normally, the intestines maintain a dynamic and rapid fluctuation in cellular oxygen tension, with the tips of the epithelial villi being hypoxic and the base of the epithelial villi better oxygenated. A dysregulated epithelial oxygen tension plays a role in intestinal inflammation and resolution in IBD (see Shah Y. M., Molecular and Cellular Pediatrics, 2016 December; 3(1):1). Even though HIF-1α and HIF-2α can bind to the same canonical hypoxia response elements (HREs), multiple studies have demonstrated that HIF-1α and HIF-2α regulate distinct subset of genes, leading to contrasting effect in symptoms of IBD. HIF-1α in intestinal epithelial cells is widely recognized as a major protective factor in IBD (see Karhausen J, et al. J Clin Invest. 2004; 114(8):1098-1106; Furuta G T, et al. J Exp Med. 2001; 193(9):1027-1034). However, HIF-2α activation contributes to IBD through multiple mechanisms, including directly regulating a number of pro-inflammatory cytokines such as tumor necrosis factor-α to drive inflammation, and indirectly disrupting intestine barrier integrity through increasing the turnover of tight junction protein occluding (see Xue X, et al. Gastroenterology. 2013; 145 (4):831-841; Glover L E, et al. Proc Natl Acad Sci USA. 2013; 110(49):19820-19825). Therefore, in IBD, a HIF-2α inhibitor holds promise of suppressing chronic activation of HIF-2α to revert the pro-inflammatory response and increase the intestinal barrier integrity.

With the growing epidemic of obesity and metabolic syndrome, NASH is becoming a common chronic liver disease and limited therapeutic options are available. A recent study has demonstrated a positive correlation between intestinal HIF-2α signaling with body-mass index and hepatic toxicity, with further animal model study supporting the causality of this correlation (see Xie C, et al. Nat Med. 2017 November; 23(11):1298-1308). Thus, targeting intestinal HIF-2α represents a novel therapeutic strategy for NASH.

PAH is a life-threatening disease with very poor prognosis. Progressive pulmonary vascular remodeling, characterized by concentric pulmonary arterial wall thickening and obliterative intimal lesions, is one of the major causes for the elevation of pulmonary vascular resistance (PVR) and pulmonary arterial pressure (PAP) in patients with PAH (see Aggarwal S, et al. Compr Physiol. 2013 July; 3(3):1011-34). Recently, HIF-2α is found to contribute to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31): 8801-8806, Tang H, et al. Am J Physiol Lung Cell Mol Physiol. 2018 Feb. 1; 314(2):L256-L275). These studies have offered new insight into the role of pulmonary endothelial HIF-2α in regulating the pulmonary vascular response to hypoxia, and offer a much-needed intervention therapeutic strategy by targeting HIF-2α.

Iron is an essential nutrient that is required for oxygen delivery and serves as a cofactor in many key enzymatic and redox reactions. HIF-2α regulates the expression of key genes that contribute to iron absorption, which, when disrupted, leads to iron load disorders. For example, an elegant study with mice lacking HIF-2α in the intestinal epithelium showed HIF-2α knockout results in a significant decrease in the duodenal levels of Dmt1, Dcytb and FPN mRNAs, all important genes in iron transport and absorption. More importantly, these effects were not compensated by HIF-1α (see Mastrogiannaki M, et al. J Clin Invest. 2009; 119(5): 1159-1166).

Thus, a small molecule that targets HIF-2 α holds potential of improving iron homeostasis in patients with iron disorders.

SUMMARY

In a first aspect, provided is a method of treating cancer in a patient, comprising administering to the patient a HIF-2α inhibitor of Formula (I):

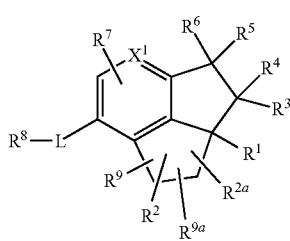

wherein:

$X^1$ is CH or N;

$R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, and $R^{15}$ and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;

$R^2$ is hydrogen, deuterium, alkyl, halo, haloalkyl, alkenyl, or alkynyl;

$R^{2a}$ is hydrogen, halo, or deuterium;

$R^3$ and $R^4$ are independently hydrogen, deuterium, alkyl, cycloalkyl, halo, haloalkyl, hydroxyalkyl, or alkoxyalkyl; or $R^3$ and $R^4$ together with the carbon to which they are attached form oxo, 3 to 6 membered cycloalkylene, or 4 to 6 membered optionally substituted heterocyclylene;

$R^5$ is hydrogen, deuterium, alkyl, halo, haloalkyl, hydroxy, or alkoxy;

$R^6$ is hydrogen, deuterium, alkyl, cycloalkyl, or halo; or $R^5$ and $R^6$ together with the carbon to which they are attached form oxo, alkyldienyl, 3 to 6 membered cycloalkylene, or 4 to 6 membered optionally substituted heterocyclylene; provided $R^5$ and $R^6$ and $R^3$ and $R^4$ together with the carbon to which they are attached do not form oxo, cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, SO$_2$, O, CO, or NR$^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl and $R^g$ and $R^h$ are independently selected from hydrogen, deuterium, and halo;

$R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or when $R^9$ and $R^2$ are attached to the same carbon atom, they can combine to form oxo, alkyldienyl, 3 to 6 membered cycloalkylene, or 4 to 6-membered heterocyclylene; and $R^{9a}$ is hydrogen, halo, or deuterium; or a pharmaceutically acceptable salt thereof;

in combination with a PARP inhibitor, or a pharmaceutically acceptable salt thereof.

In a second aspect, provided is a combination comprising a Hif-2α inhibitor of Formula (I), as described in the first aspect (and embodiments 1 to 52 hereinunder) or a pharmaceutically acceptable salt thereof, and a PARP inhibitor or a pharmaceutically acceptable salt thereof. In an embodiment of the second aspect, the combination of the second aspect is for use in the treatment of cancer in a patient.

In a third aspect, provided is use of a combination comprising a Hif-2α inhibitor of Formula (I), as described in the first aspect (and embodiments 1 to 52 hereinunder) or a pharmaceutically acceptable salt thereof, and a PARP inhibitor or a pharmaceutically acceptable salt thereof for the treatment of cancer in a patient.

In a fourth aspect, a pharmaceutical composition comprising a HIF-2α inhibitor of Formula (I), as described in the first aspect (and embodiments 1 to 52 hereinunder) or a pharmaceutically acceptable salt thereof, and a PARP inhibitor (or embodiments thereof disclosed hereinunder) or a pharmaceutically acceptable salt thereof and a pharmaceutically acceptable excipient. In an embodiment of the fourth aspect, the pharmaceutical combination of the fourth aspect is for the treatment of cancer in a patient.

In a first subembodiment of first, second, third, and fourth aspects, and subembodiments thereof, the HIF-2α inhibitor is 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile (Compound 5).

Compounds of Formula (I), including compound 5 and polymorph(s) thereof, are disclosed in PCT Application No. PCT/US20/28579, filed on Apr. 16, 2020.

In a fourth subembodiment of first, second, third, and fourth aspects and any of embodiments and subembodiments contained therein the cancer is selected from renal cancer, brain cancer, cartilage cancer, kidney cancer, salivary gland cancer, skin cancer, stomach cancer, glioblastoma, neuroblastoma, paraganglioma, pheochromocytoma, somatostatinomas, hemangioblastomas, gastrointestinal stromal tumors, pituitary tumors, leiomyomas, leiomyosarcomas, polycythaemia, retinal cancers, lung cancer, pancreatic cancer, liver cancer, ovarian cancer, breast cancer, prostate cancer, colorectal cancer, head and neck cancer, cervical cancer, endometrial cancer, bladder cancer, gastric cancer, esophageal cancer, lymphoma, melanoma, mesothelioma, sarcoma, neuroendocrine tumors, uveal melanoma, urothelial cancer, fallopian tube cancer, primary peritoneal cancer, cholangiocarcinoma, Ewing Sarcoma, uterine leiomyosarcoma, chronic lymphocytic leukemia, acute lymphocytic leukemia, T-cell-prolymphocytic leukemia, multiple myeloma, acute myeloid leukemia, chronic myelogenous leukemia, germ cell cancer, osteosarcoma, biliary tract cancer, soft-tissue sarcoma, rhabdomyosarcoma, mantle-cell lymphoma, and endocrine gland neoplasms.

In a fifth aspect provided is a compound of Formula (IA):

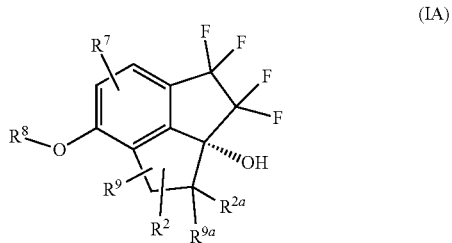

wherein:
$R^2$ is hydrogen or deuterium;
$R^9$ is fluoro;
$R^7$ is hydrogen;
$R^8$ is phenyl substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl and $R^g$ and $R^h$ are independently selected from hydrogen, deuterium, and halo;
$R^{2a}$ is hydrogen, deuterium, or fluoro; and
$R^{9a}$ is fluoro; or
a pharmaceutically acceptable salt thereof.

Compounds of Formula (IA) are a subset of compounds of Formula (I).

In a sixth aspect, provided is a method of treating a disease treatable by inhibition of HIF-2α in a patient, preferably the patient is in need of such treatment, which method comprises administering to the patient, preferably a patient in need of such treatment, a therapeutically effective amount of compound of Formula (IA) (or any of the embodiments thereof described herein) or a pharmaceutically acceptable salt thereof. The therapeutically effective amount of compound (IA) can be administered in a pharmaceutical composition comprising the compound of Formula (IA), or a pharmaceutically acceptable salt thereof, and a pharmaceutically acceptable excipient.

In one embodiment of the sixth aspect, the disease is cancer such as renal cancer, glioblastoma (see PNAS 2017, 114, E6137-E6146), renal cell carcinoma in particular clear cell renal cell carcinoma, small cell lung cancer, glioblastoma, ovarian cancer, liver cancer, neuroblastoma, pheochromocytomas and paragangliomas (see European Journal of Cancer 2017, 86, 1-4), somatostatinomas, hemangioblastomas, gastrointestinal stromal tumors (GIST), pituitary tumors, leiomyomas, leiomyosarcomas, polycythaemia or retinal tumors. In another embodiment, non-cancer diseases that could benefit from Hif-2α inhibition include VHL (von Hippel-Lindau) disease (see Oncotarget, 2015, 6, 23036-23037), pulmonary disease such as PAH (pulmonary artery hypertension) (see Mol. Cell. Biol. 2016, 36, 1584-1594), reflux esophagitis (see Current Opinion in Pharmacology 2017, 37: 93-99), hepatic steatosis (see Nature Medicine 2017, 23, 1298-1308), a liver disease such as NASH, inflammatory disease such as inflammatory bowel disease (see Nature Reviews gastroenterology & Hepatology 2017, 14, 596), autoimmune disease such as Graft-versus-Host-Disease (see Blood, 2015, 126, 1865), or iron overload.

In a seventh aspect, the disclosure is directed to a pharmaceutical composition comprising a compound of Formula (IA) (or any of the embodiments thereof described herein) or a pharmaceutically acceptable salt thereof; and a pharmaceutically acceptable excipient.

In an eighth aspect, provided is a compound of Formula (IA), (or any embodiments thereof described herein) or a pharmaceutically acceptable salt thereof for use as a medicament. In one embodiment, the compound Formula (IA) (and any embodiments thereof described herein) or a pharmaceutically acceptable salt, is useful for the treatment of one or more of diseases disclosed in the sixth aspect or embodiment of the sixth aspect above.

In a ninth aspect provided is the use of a compound of Formula (IA), or a pharmaceutically acceptable salt thereof (and any embodiments thereof disclosed herein) in the manufacture of a medicament for treating a disease in a patient in which the activity of HIF-2α contributes to the pathology and/or symptoms of the disease. In one embodiment the disease is one or more of diseases disclosed in the sixth aspect above or embodiment of the sixth aspect.

In a tenth aspect provided is a method of inhibiting HIF-2α which method comprises contacting HIF-2α with a compound of Formula (IA) (or any of the embodiments thereof described herein) or a pharmaceutically acceptable salt thereof; or contacting HIF-2α with a pharmaceutical composition comprising a compound of Formula (IA) (or any of the embodiments thereof described herein) or a pharmaceutically acceptable salt thereof; and a pharmaceutically acceptable excipient.

BRIEF DESCRIPTION OF THE DRAWINGS

FIG. 1 provides results of a co-immunoprecipitation assay for measuring inhibition of HIF-2α and ARNT dimerization in Primary Pulmonary Artery Smooth Muscle Cells (PASMC) and Human Pulmonary Artery Endothelial Cells (HPAEC).

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

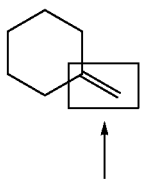

the alkyldienyl group is enclosed by the box which is indicated by the arrow.

"Haloalkyldienyl" is alkyldienyl that is substituted with one or two halo, each group as defined herein.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfoxide" means a —SOR radical where R is alkyl as defined above, e.g., methylsulfoxide, ethylsulfoxide, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Alkylcarbonyl" means a —C(O)R radical where R is alkyl as defined herein, e.g., methylcarbonyl, ethylcarbonyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above, e.g., benzyl, phenethyl, and the like.

"Bicyclic cycloalkyl" means a fused bicyclic saturated monovalent hydrocarbon radical of six to ten carbon atoms which is optionally substituted with one or two substituents independently selected from alkyl, halo, alkoxy, hydroxy, and cyano. Examples include, but are not limited to, decalin, octahydro-1H-indene, and the like.

"Cycloalkyl" means a monocyclic saturated monovalent hydrocarbon radical of three to ten carbon atoms optionally substituted with one or two substituents independently selected from alkyl, alkyldienyl, halo, alkoxy, hydroxy, cyano, haloalkyldienyl and cyanoalkyl. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. Cycloalkyl may include cycloalkylene as defined herein.

"Cycloalkylalkyl" means a -(alkylene)-R radical where R is cycloalkyl as defined above, e.g., cyclopropylmethyl, cyclohexylmethyl, and the like.

"Cycloalkylene" means a divalent cycloalkyl, as defined above, unless stated otherwise.

"Cycloalkenyl" means a monocyclic monovalent hydrocarbon radical of three to ten carbon atoms containing one or two double bond(s) optionally substituted with one or two substituents independently selected from alkyl, halo, alkoxy, hydroxy, cyano, and cyanoalkyl. Examples include, but are not limited to, cyclopropenyl, cyclobutenyl, cyclopentenyl, or cyclohexenyl, and the like.

"Oxocycloalkenyl" means a monocyclic monovalent hydrocarbon radical of three to ten carbon atoms containing one or two double bond(s) and an oxo group, and is optionally substituted with one or two substituents independently selected from alkyl, halo, alkoxy, hydroxy, cyano, and cyanoalkyl. Examples include, but are not limited to, 3-oxocyclohex-1-enyl, and the like.

"Cyanoalkyl" means a linear monovalent hydrocarbon radical of one to six carbon atoms or a branched monovalent hydrocarbon radical of three to six carbons substituted with cyano e.g., cyanomethyl, cyanoethyl, and the like.

"Carboxy" means —COOH.

"Dialkylamino" means a —NRR' radical where R and R' are alkyl as defined above, e.g., dimethylamino, methylethylamino, and the like.

"Disubstituted amino" means a —NRR' radical where R and R' are independently alkyl, haloalkyl, hydroxyalkyl, alkoxyalkyl, or alkylcarbonyl, each as defined herein, e.g., dimethylamino, ethylmethylamino, bis-hydroxyethylamino, bis-methoxyethylamino, diethylaminoethylamino, and the like.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C, unless stated otherwise. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocyclylene" means a divalent heterocyclyl, as defined above, unless stated otherwise. When heterocyclene contains 4, 5, or 6 rings atoms, it may be referred to herein as 4 to 6 membered heterocyclylene.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical as defined above.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

The phrase "R$^2$ and R$^9$ are attached to the ring carbon atom that is meta to the ring carbon attached to R$^1$" means the R$^2$ and R$^9$ are located as indicated below:

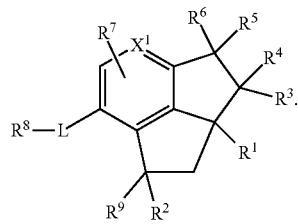

The term "oxo," as used herein, alone or in combination, refers to =(O).

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of Formula (I). For example, when compounds of Formula (I) contain groups such as hydroxy, carboxy, thiol or any group containing a nitrogen atom(s), these groups can be protected with suitable protecting groups. A comprehensive list of suitable protective groups can be found in T. W. Greene, *Protective Groups in Organic Synthesis*, 5th Ed., John Wiley & Sons, Inc. (2014), the disclosure of which is incorporated herein by reference in its entirety. The protected derivatives of compounds of the present disclosure can be prepared by methods well known in the art.

The present disclosure also includes polymorphic forms of compounds of Formula (I) or a pharmaceutically acceptable salt thereof. Polymorphs are different crystalline forms of a compound that differ in arrangements of the molecules of that compound in a crystal lattice. Therefore, a single compound may give rise to a variety of polymorphic forms. The polymorphs of a compound usually have different melting points, solubilities, densities and optical properties. Polymorphic forms of a compound can be distinguished by several techniques such as X-ray diffractometry, IR or Raman spectroscopy.

The term "prodrug" refers to a compound that is made more active in vivo. Certain compounds of Formula (I) may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds of Formula (I) are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound of Formula (I).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of Formula (I) may have asymmetric centers. Compounds of Formula (I) containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diastereomeric forms, and racemic forms are within the scope of this disclosure, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of Formula (I) are within the scope of this disclosure.

The compounds of Formula (I) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^2$H or $^3$H, or one or more carbon atoms are replaced by $^{13}$C- or $^{14}$C-enriched carbon. Positron emitting isotopes such as $^{15}$O, $^{13}$N, $^{11}$C, and $^{15}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

Certain structures provided herein are drawn with one or more floating substituents. Unless provided otherwise or otherwise clear from the context, the substituent(s) may be present on any atom of the ring to which it is attached, where chemically feasible and valency rules permitting. For example, in the structure:

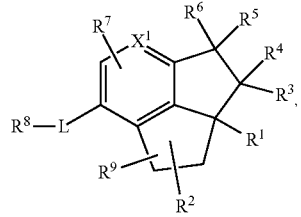

the $R^7$ substituent can replace any hydrogen on the benzo portion of the tricyclic ring, including the hydrogen of CH when $X^1$ is CH.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Optionally substituted heterocyclylene" is divalent optionally substituted heterocyclyl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1:1), and the like.

"Spiroheterocyclyl" means a saturated bicyclic ring having 6 to 10 ring atoms in which one, two, or three ring atoms are heteroatom selected from N, O, or $S(O)_n$, where n is an integer from 0 to 2, the remaining ring atoms being C and the rings are connected through only one atom, the connecting atom is also called the spiroatom, most often a quaternary carbon ("spiro carbon"). The spiroheterocyclyl ring is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano. Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The phrase "heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano" in the definition of $R^9$ in Formula (I) (and similar phrases used to define other groups in Formula (I)) is intended to cover heteroaryl that is unsubstituted and heteroaryl that is substituted with any one of $R^d$, $R^e$, and $R^f$.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" or "administering in combination with" means the administration of two or more therapeutic agents to treat a disease or disorder described in the present disclosure. Such administration encompasses co-administration of these therapeutic agents in a simultaneous manner, such as in a single capsule or tablet having a fixed ratio of active ingredients or in multiple, separate capsules or tablets for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "synergy" or "synergistic" are used to mean that the result of the combination of a HIF-2α inhibitor or a pharmaceutically acceptable salt thereof and a PARP inhibitor or a pharmaceutically acceptable salt thereof is greater than the sum of each compound individually. This improvement in the disease, condition or disorder being treated is a "synergistic" effect.

A "synergistic amount" is an amount of the combination of a HIF-2α inhibitor or a pharmaceutically acceptable salt thereof and a PARP inhibitor or a pharmaceutically acceptable salt thereof that results in a synergistic effect, as "synergistic" is defined herein.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of HIF-2α, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of HIF-2α activity compared to normal. Representative HIF-2α inhibitors of Formula (I) are disclosed in Compound Table I below:

TABLE I

| Compound # | Structure | Name |
|---|---|---|
| 1 | 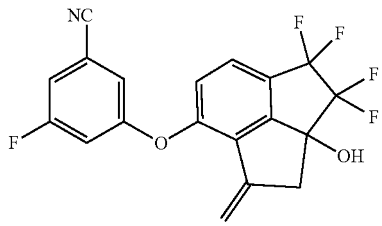 | 3-fluoro-5-((3,3,4,4-tetrafluoro-2a-hydroxy-1-methylene-2,2a,3,4-tetrahydro-1H-cyclopenta[cd]inden-7-yl)oxy)benzonitrile |
| 2 | 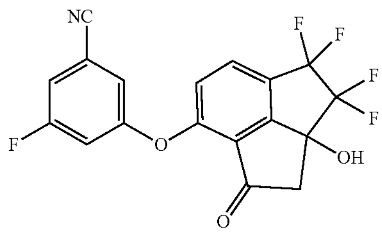 [SMILES: N#Cc1cc(F)cc(Oc2ccc3c4c2C(=O)CC4(O)C(F)(F)C3(F)F)c1] | 3-fluoro-5-((3,3,4,4-tetrafluoro-2a-hydroxy-1-oxo-2,2a,3,4-tetrahydro-1H-cyclopenta[cd]inden-7-yl)oxy)benzonitrile |
| 3 | 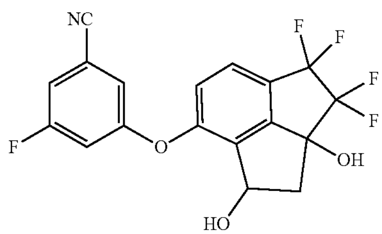 [SMILES: N#Cc1cc(F)cc(Oc2ccc3c4c2C(O)CC4(O)C(F)(F)C3(F)F)c1] | 3-fluoro-5-((3,3,4,4-tetrafluoro-1,2a-dihydroxy-2,2a,3,4-tetrahydro-1H-cyclopenta[cd]inden-7-yl)oxy)benzonitrile |
| 4 | 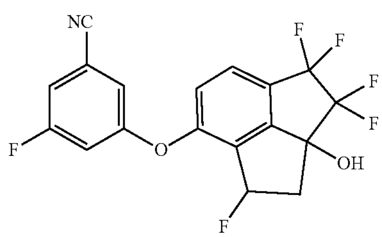 [SMILES: N#Cc1cc(F)cc(Oc2ccc3c4c2C(F)CC4(O)C(F)(F)C3(F)F)c1] | 3-fluoro-5-((1,3,3,4,4-pentafluoro-2a-hydroxy-2,2a,3,4-tetrahydro-1H-cyclopenta[cd]inden-7-yl)oxy)benzonitrile |
| 5 | 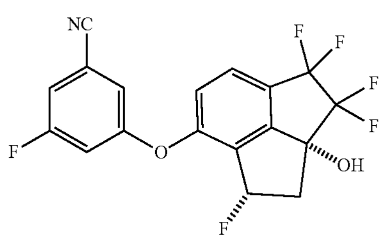 [SMILES: N#Cc1cc(F)cc(Oc2ccc3c4c2[C@@H](F)C[C@]4(O)C(F)(F)C3(F)F)c1] | 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile |
| 6 | 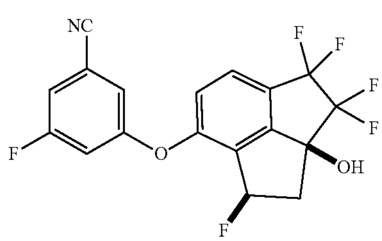 [SMILES: N#Cc1cc(F)cc(Oc2ccc3c4c2[C@H](F)C[C@@]4(O)C(F)(F)C3(F)F)c1] | 3-fluoro-5-(((1R,2aS)-1,3,3,4,4-pentafluoro-2a-hydroxy-2,2a,3,4-tetrahydro-1H-cyclopenta[cd]inden-7-yl)oxy)benzonitrile |

TABLE I-continued

| Compound # | Structure | Name |
|---|---|---|
| 7 | 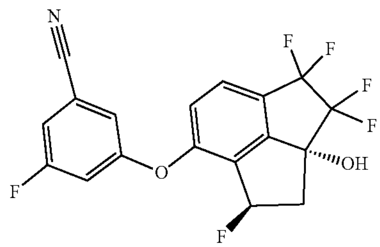 [SMILES: N#Cc1cc(F)cc(Oc2ccc3c4c2[C@H](F)C[C@]4(O)C(F)(F)C3(F)F)c1] | 3-fluoro-5-(((1R,2aR)-1,3,3,4,4-pentafluoro-2a-hydroxy-2,2a,3,4-tetrahydro-1H-cyclopenta[cd]inden-7-yl)oxy)benzonitrile |
| 8 | 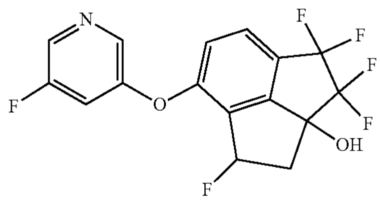 [SMILES: OC12CC(F)c3c(Oc4cncc(F)c4)ccc(c31)C(F)(F)C2(F)F] | 1,3,3,4,4-pentafluoro-7-((5-fluoropyridin-3-yl)oxy)-1,2,3,4-tetrahydro-2aH-cyclopenta[cd]inden-2a-ol |
| 9 | 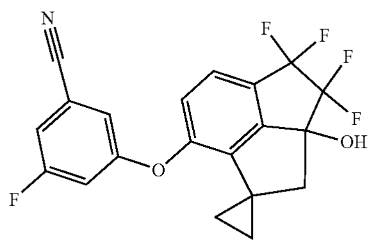 [SMILES: N#Cc1cc(F)cc(Oc2ccc3c4c2C2(CC2)CC4(O)C(F)(F)C3(F)F)c1] | 3-fluoro-5-((3,3,4,4-tetrafluoro-2a-hydroxy-2,2a,3,4-tetrahydrospiro[cyclopenta[cd]indene-1,1'-cyclopropan]-7-yl)oxy)benzonitrile |
| 10 | 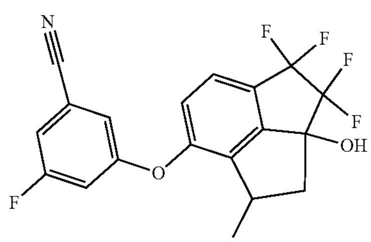 [SMILES: CC1CC2(O)c3c(ccc(Oc4cc(F)cc(C#N)c4)c31)C(F)(F)C2(F)F] | 3-fluoro-5-((3,3,4,4-tetrafluoro-2a-hydroxy-1-methyl-2,2a,3,4-tetrahydro-1H-cyclopenta[cd]inden-7-yl)oxy)benzonitrile |
| 11 | 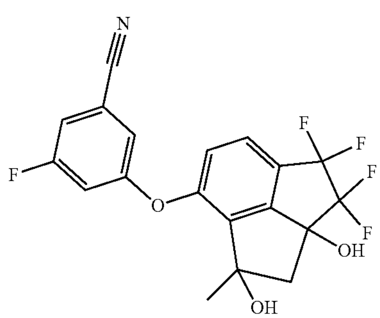 [SMILES: CC1(O)CC2(O)c3c(ccc(Oc4cc(F)cc(C#N)c4)c31)C(F)(F)C2(F)F] | 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile |
| 12 | 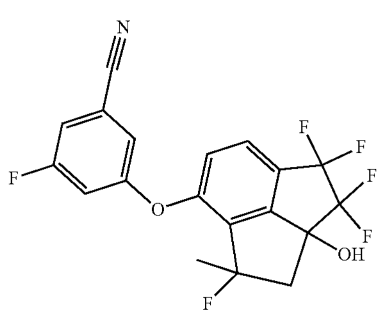 [SMILES: CC1(F)CC2(O)c3c(ccc(Oc4cc(F)cc(C#N)c4)c31)C(F)(F)C2(F)F] | 3-fluoro-5-((1,3,3,4,4-pentafluoro-2a-hydroxy-1-methyl-2,2a,3,4-tetrahydro-1H-cyclopenta[cd]inden-7-yl)oxy)benzonitrile |

TABLE I-continued

| Compound # | Structure | Name |
|---|---|---|
| 13 | 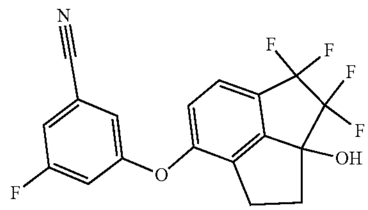 [SMILES: N#Cc1cc(F)cc(Oc2ccc3c4c2CCC4(O)C(F)(F)C3(F)F)c1] | 3-fluoro-5-((3,3,4,4-tetrafluoro-2a-hydroxy-2,2a,3,4-tetrahydro-1H-cyclopenta[cd]inden-7-yl)oxy)benzonitrile |
| 14 | 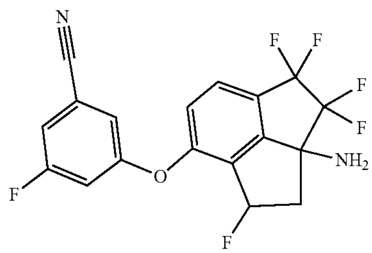 [SMILES: N#Cc1cc(F)cc(Oc2ccc3c4c2C(F)CC4(N)C(F)(F)C3(F)F)c1] | 3-((2a-amino-1,3,3,4,4-pentafluoro-2,2a,3,4-tetrahydro-1H-cyclopenta[cd]inden-7-yl)oxy)-5-fluorobenzonitrile |
| 15 | 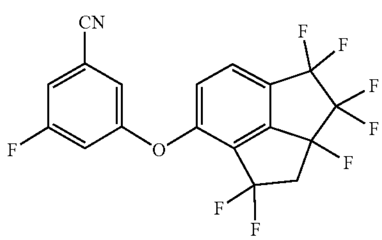 [SMILES: N#Cc1cc(F)cc(Oc2ccc3c4c2C(F)(F)CC4(F)C(F)(F)C3(F)F)c1] | 3-fluoro-5-((1,1,2a,3,3,4,4-heptafluoro-2,2a,3,4-tetrahydro-1H-cyclopenta[cd]inden-7-yl)oxy)benzonitrile |
| 16 | 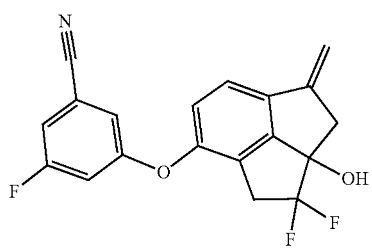 [SMILES: C=C1CC2(O)c3c1ccc(Oc1cc(F)cc(C#N)c1)c3CC2(F)F] | 3-((3,3-difluoro-2a-hydroxy-1-methylene-2,2a,3,4-tetrahydro-1H-cyclopenta[cd]inden-5-yl)oxy)-5-fluorobenzonitrile |
| 17 | 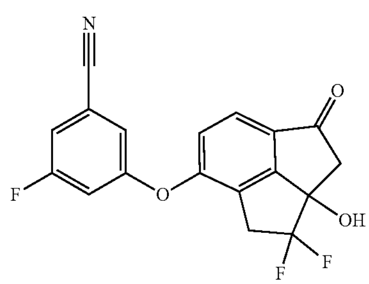 [SMILES: N#Cc1cc(F)cc(Oc2ccc3c4c2CC(F)(F)C4(O)CC3=O)c1] | 3-((3,3-difluoro-2a-hydroxy-1-oxo-2,2a,3,4-tetrahydro-1H-cyclopenta[cd]inden-5-yl)oxy)-5-fluorobenzonitrile |
| 18 | 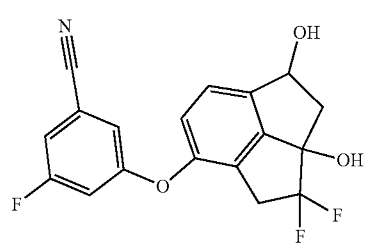 [SMILES: N#Cc1cc(F)cc(Oc2ccc3c4c2CC(F)(F)C4(O)CC3O)c1] | 3-((3,3-difluoro-1,2a-dihydroxy-2,2a,3,4-tetrahydro-1H-cyclopenta[cd]inden-5-yl)oxy)-5-fluorobenzonitrile |

TABLE I-continued

| Compound # | Structure | Name |
|---|---|---|
| 19 | 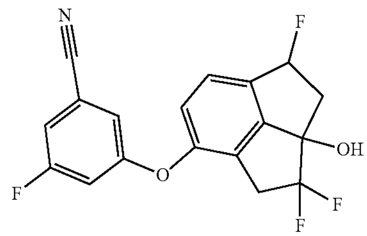 [SMILES: N#Cc1cc(F)cc(Oc2ccc3c4c2CC(F)(F)C4(O)CC3F)c1] | 3-fluoro-5-((1,3,3-trifluoro-2a-hydroxy-2,2a,3,4-tetrahydro-1H-cyclopenta[cd]inden-5-yl)oxy)benzonitrile |
| 20 | 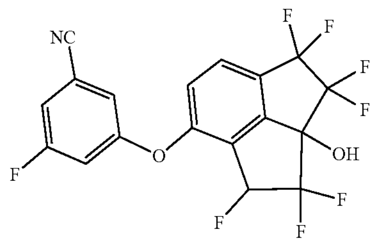 [SMILES: N#Cc1cc(F)cc(Oc2ccc3c4c2C(F)C(F)(F)C4(O)C(F)(F)C3(F)F)c1] | 3-fluoro-5-((1,2,2,3,3,4,4-heptafluoro-2a-hydroxy-2,2a,3,4-tetrahydro-1H-cyclopenta[cd]inden-7-yl)oxy)benzonitrile |
| 21 | 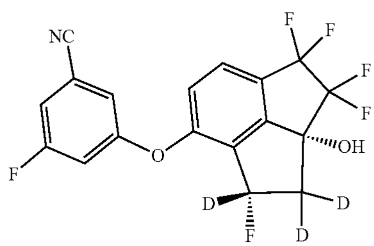 [SMILES: [2H]C1([2H])[C@@]2(O)c3c(ccc(Oc4cc(F)cc(C#N)c4)c3[C@@]1([2H])F)C(F)(F)C2(F)F] | 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile |
| 22 | 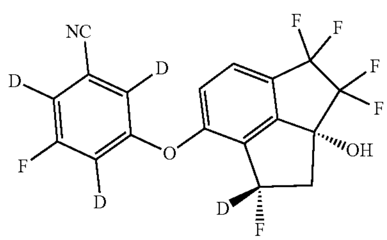 [SMILES: [2H]c1c(F)c([2H])c(Oc2ccc3c4c2[C@@]([2H])(F)C[C@]4(O)C(F)(F)C3(F)F)c([2H])c1C#N] | 3-fluoro-5-(((1S,2aR)-1,3,3,4,4-pentafluoro-2a-hydroxy-2,2a,3,4-tetrahydro-1H-cyclopenta[cd]inden-7-yl-1-d)oxy)benzonitrile-2,4,6-d3 |
| 23a | 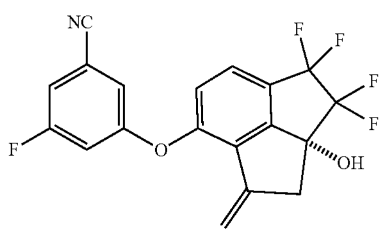 [SMILES: C=C1C[C@@]2(O)c3c(ccc(Oc4cc(F)cc(C#N)c4)c31)C(F)(F)C2(F)F] | (R)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile |
| 23b | 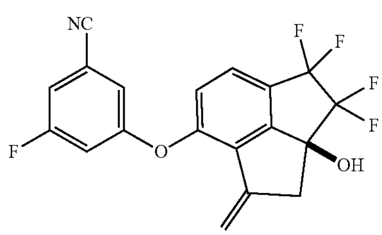 [SMILES: C=C1C[C@]2(O)c3c(ccc(Oc4cc(F)cc(C#N)c4)c31)C(F)(F)C2(F)F] | (S)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile |

TABLE I-continued

| Compound # | Structure | Name |
|---|---|---|
| 24a | 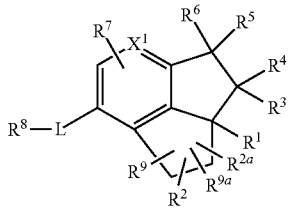<br>24a | 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile |
| 24b | 24b | 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)benzonitrile |

EMBODIMENTS

In further embodiments 1-52 below, the present disclosure includes:

1. In embodiment 1, provided is a method of treating cancer in a patient, comprising administering to the patient a HIF-2α inhibitor of Formula (I):

(I)

wherein:

$X^1$ is CH or N;

$R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, and $R^{15}$ and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;

$R^2$ is hydrogen, deuterium, alkyl, halo, haloalkyl, alkenyl, or alkynyl;

$R^{2a}$ is hydrogen or deuterium;

$R^3$ and $R^4$ are independently hydrogen, deuterium, alkyl, cycloalkyl, halo, haloalkyl, hydroxyalkyl, or alkoxyalkyl; or $R^3$ and $R^4$ together with the carbon to which they are attached form oxo, 3 to 6 membered cycloalkylene, or 4 to 6 membered optionally substituted heterocyclylene;

$R^5$ is hydrogen, deuterium, alkyl, halo, haloalkyl, hydroxy, or alkoxy;

$R^6$ is hydrogen, deuterium, alkyl, cycloalkyl, or halo; or $R^5$ and $R^6$ together with the carbon to which they are attached form oxo, alkyldienyl, 3 to 6 membered cycloalkylene, or 4 to 6 membered optionally substituted heterocyclylene; provided $R^5$ and $R^6$ and $R^3$ and $R^4$ together with the carbon to which they are attached do not form oxo, cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, SO$_2$, O, CO, or NR$^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, $R^c$, $R^g$ and/or $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl and $R^g$ and $R^h$ are independently selected from hydrogen, deuterium, and halo; and $R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or when $R^9$ and $R^2$ are attached to the same carbon atom, they can combine to form oxo, alkyldienyl, 3 to 6 membered cycloalkylene, or 4 to 6-membered heterocyclylene;

$R^{9a}$ is hydrogen or deuterium;
a pharmaceutically acceptable salt thereof
in combination with a PARP inhibitor or a pharmaceutically acceptable salt thereof.

2. In embodiment 2, provided is a method of treating cancer in a patient, comprising administering to the patient a therapeutically effective amount of a HIF-2α inhibitor of Formula (I):

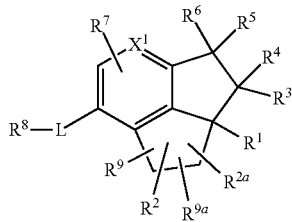

(I)

wherein:
$X^1$ is CH or N;
$R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, and $R^{15}$ and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;
$R^2$ is hydrogen, deuterium, alkyl, halo, haloalkyl, alkenyl, or alkynyl;
$R^{2a}$ is hydrogen, halo, or deuterium;
$R^3$ and $R^4$ are independently hydrogen, deuterium, alkyl, cycloalkyl, halo, haloalkyl, hydroxyalkyl, or alkoxyalkyl; or
$R^3$ and $R^4$ together with the carbon to which they are attached form oxo, 3 to 6 membered cycloalkylene, or 4 to 6 membered optionally substituted heterocyclylene;
$R^5$ is hydrogen, deuterium, alkyl, halo, haloalkyl, hydroxy, or alkoxy;
$R^6$ is hydrogen, deuterium, alkyl, cycloalkyl, or halo; or
$R^5$ and $R^6$ together with the carbon to which they are attached form oxo, alkyldienyl, 3 to 6 membered cycloalkylene, or 4 to 6 membered optionally substituted heterocyclylene; provided $R^5$ and $R^6$ and $R^3$ and $R^4$ together with the carbon to which they are attached do not form oxo, cycloalkylene or optionally substituted 4 to 6 membered heterocyclylene simultaneously;
$R^7$ is hydrogen, deuterium, alkyl, alkoxy, cyano, halo, haloalkyl, or haloalkoxy;
L is a bond, S, SO, SO$_2$, O, CO, or NR$^{16}$ where $R^{16}$ is hydrogen or alkyl;
$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl and $R^g$ and $R^h$ are independently selected from hydrogen, deuterium, and halo; and
$R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or
when $R^9$ and $R^2$ are attached to the same carbon atom, they can combine to form oxo, alkyldienyl, 3 to 6 membered cycloalkylene, or 4 to 6-membered heterocyclylene; $R^{9a}$ is hydrogen, halo, or deuterium; or
a pharmaceutically acceptable salt thereof;
in combination with a therapeutically effective amount of a PARP inhibitor or a pharmaceutically acceptable salt thereof.

3. In embodiment 3, the method of embodiment 1 or 2, is wherein the compound of Formula (I) or a pharmaceutically acceptable salt thereof, is wherein $R^3$ and $R^4$ are independently halo.

4. In embodiment 4, the method of embodiment 1 or 2, is wherein the compound of Formula (I) or a pharmaceutically acceptable salt thereof, is wherein $R^3$ is halo and $R^4$ is hydrogen.

5. In embodiment 5, the method of embodiment 1, 2, or 3, is wherein the compound of Formula (I) or a pharmaceutically acceptable salt thereof, is wherein $R^1$ is hydroxy.

6. In embodiment 6, the method of any one of embodiments 1 to 3, is wherein the compound of Formula (I) or a pharmaceutically acceptable salt thereof, wherein is $R^1$ is amino.

7. In embodiment 7, the method of any one of embodiments 1 to 6, is wherein the compound of Formula (I) or a pharmaceutically acceptable salt thereof, is wherein $R^6$ is halo.

8. In embodiment 8, the method of any one of embodiments 1 to 6, is wherein the compound of Formula (I) or a pharmaceutically acceptable salt thereof, is wherein $R^6$ is alkyl, preferably $R^6$ is methyl.

9. In embodiment 9, the method of any one of embodiments 1 to 6, is wherein the compound of Formula (I) or a pharmaceutically acceptable salt thereof, is wherein $R^6$ is hydrogen.

10. In embodiment 10, the method of any one of embodiments 1 to 6, is wherein the compound of Formula (I) or a pharmaceutically acceptable salt thereof, is wherein $R^6$ is cycloalkyl, preferably cyclopropyl, cyclobutyl, cyclopentyl or cyclohexyl.

11. In embodiment 11, the method of any one of embodiments 1 to 10, is wherein the compound of Formula (I) or a pharmaceutically acceptable salt thereof, is wherein $R^5$ is halo, preferably fluoro.

12. In embodiment 12, the method of any one of embodiments 1 to 10, is wherein the compound of Formula (I) or a pharmaceutically acceptable salt thereof, is wherein $R^5$ is haloalkyl, preferably $R^5$ is difluoromethyl or trifluoromethyl.

13. In embodiment 13, the method of any one of embodiments 1 to 10, is wherein the compound of Formula (I) or a pharmaceutically acceptable salt thereof, is wherein $R^5$ is alkyl, preferably $R^5$ is methyl or ethyl.

14. In embodiment 14, the method of any one of embodiments 1 to 10, is wherein the compound of Formula (I) or a pharmaceutically acceptable salt thereof, is wherein $R^5$ is hydrogen or alkoxy.

15. In embodiment 15, the method of any one of embodiments 1 to 6, is wherein the compound of Formula (I) or a pharmaceutically acceptable salt thereof, is wherein $R^5$ and $R^6$ together with the carbon to which they are attached form 3 to 6 membered cycloalkylene, preferably cyclopropylene, cyclobutylene or cyclopentylene optionally substituted with one or two fluoro.

16. In embodiment 16, the method of any one of embodiments 1 to 15, is wherein the compound of Formula (I) or a pharmaceutically acceptable salt thereof, is wherein $X^1$ is $CR^7$.

17. In embodiment 17, the method of embodiment 1, is wherein the compound of Formula (I) or a pharmaceutically acceptable salt thereof, has the structure of formula (IIa1) or (IIb1):

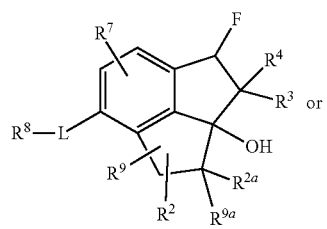
(IIa1)

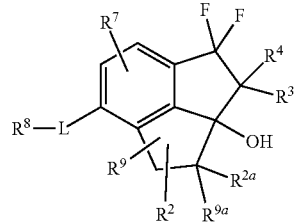
(IIb1)

18. In embodiment 18, the method of embodiment 1, is wherein the compound of Formula (I) or a pharmaceutically acceptable salt thereof, having the structure of formula (IIa1') or (IIb1'):

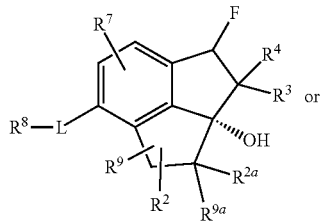
(IIa1')

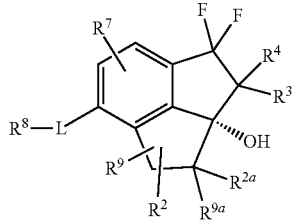
(IIb1')

19. In embodiment 19, the method of embodiment 1, is wherein the compound of Formula (I) or a pharmaceutically acceptable salt thereof, has the structure of formula (IIa) or (IIb):

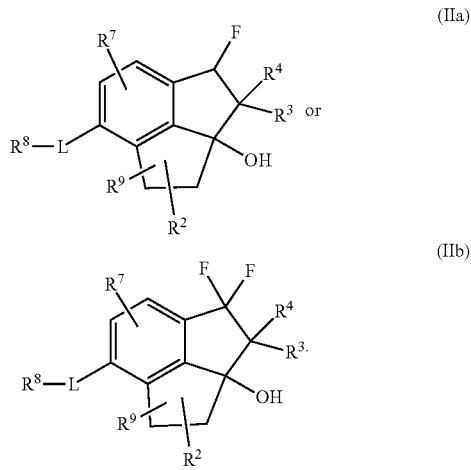
(IIa)

(IIb)

20. In embodiment 20, the method of embodiment 1, is wherein the compound of Formula (I) or a pharmaceutically acceptable salt thereof, has the structure of formula (IIa') or (IIb'):

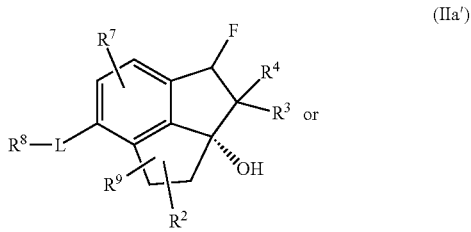
(IIa')

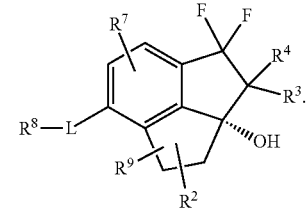
(IIb')

21. In embodiment 21, the method of embodiment 1, is wherein the compound of Formula (I) or a pharmaceutically acceptable salt thereof, has the structure of formula (IVa):

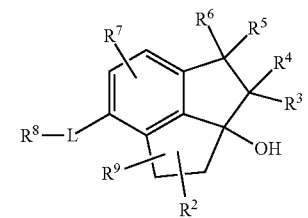
(IVa)

where $R^5$ and $R^6$ together with the carbon to which they are attached form 3 to 6 membered cycloalkylene, preferably cyclopropylene, cyclobutylene or cyclopentylene optionally substituted with one or two fluoro.

22. In embodiment 22, the method of any one of embodiments 17 to 21, is wherein the compound of Formulae (IIa1), (IIb1), (IIa1'), (IIb1'), (IIa), (IIb), (IIa'), (IIb'), and (IVa) or a pharmaceutically acceptable salt thereof, is wherein $R^3$ is fluoro.

23. In embodiment 23, the method of any one of embodiments 17 to 21, is wherein the compound of Formulae (IIa1), (IIb1), (IIa1'), (IIb1'), (IIa), (IIb), (IIa'), (IIb'), and (IVa) or a pharmaceutically acceptable salt thereof, is where $R^3$ and $R^4$ are fluoro.

24. In embodiment 24, the method of any one of embodiments 1 to 23, is wherein the compound of Formulae (I), (IIa1), (IIb1), (IIa1'), (IIb1'), (IIa), (IIb), (IIa'), (IIb'), and (IVa) or a pharmaceutically acceptable salt thereof, is wherein L is O, S, SO, $SO_2$, or NH.

25. In embodiment 25, the method of embodiment 24, is wherein the compound of Formulae (I), (IIa1), (IIb1), (IIa1'), (IIb1'), (IIa), (IIb), (IIa'), (IIb'), and (IVa) a pharmaceutically acceptable salt thereof, is wherein L is O.

26. In embodiment 26, the method of any one of embodiments 1 to 25, is wherein the compound of Formulae (I), (IIa1), (IIb1), (IIa1'), (IIb1'), (IIa), (IIb), (IIa'), (IIb'), and (IVa) is wherein $R^8$ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl.

27. In embodiment 27, the method of any one of embodiments 1 to 25, and subembodiments contained therein, is wherein the compound of Formulae (I), (IIa1), (IIb1), (IIa1'), (IIb1'), (IIa), (IIb), (IIa'), (IIb'), and (IVa) or a pharmaceutically acceptable salt thereof, is wherein $R^8$ is phenyl substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl and $R^g$ and $R^h$ are independently selected from hydrogen, and halo.

28. In embodiment 28, the method of embodiment 27 and subembodiments contained therein, or a pharmaceutically acceptable salt thereof, is wherein the compound of Formulae (I), (IIa1), (IIb1), (IIa1'), (IIb1'), (IIa), (IIb), (IIa'), (IIb') and (IVa) is wherein $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methyphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, 3-cyano-5-difluoromethylphenyl or 3-cyano-5-fluoro-2,4,6-trideuteriophenyl. In a first subembodiment of embodiment 28, $R^{10}$ is 3-cyano-5-fluorophenyl or 3-cyano-5-fluoro-2,4,6-trideuteriophenyl.

29. In embodiment 29, the method of any one of embodiments 1 to 25 and any subembodiments contained therein, is wherein the compound of Formulae (I), (IIa1), (IIb1), (IIa1'), (IIb1'), (IIa), (IIb), (IIa'), (IIb'), and (IVa) or a pharmaceutically acceptable salt thereof, is wherein $R^8$ is cycloalkyl or cycloalkylalkyl each optionally substituted with one or two substituents independently selected from alkyl, halo, alkoxy, cyano, and hydroxy.

30. In embodiment 30, the method of any one of embodiments 1 to 25 and any subembodiments contained therein, is wherein the compound of Formulae (I), (IIa1), (IIb1), (IIa1'), (IIb1'), (IIa), (IIb), (IIa'), (IIb'), and (IVa) or a pharmaceutically acceptable salt thereof, wherein $R^8$ is heteroaryl substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.

31. In embodiment 31, the method of any one of embodiments 1 to 25, is wherein the compound of Formulae (I), (IIa1), (IIb1), (IIa1'), (IIb1'), (IIa), (IIb), (IIa'), (IIb') and (IVa) or a pharmaceutically acceptable salt, thereof, is wherein $R^8$ is pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl, thien-3-yl, thiazol-4-yl, pyridin-4-yl, oxazol-2-yl, imidazol-2-yl, pyridin-2-yl, pyrazin-2-yl, or thiazol-2-yl, and is substituted with $R^a$, $R^b$, and $R^c$ wherein $R^a$ and $R^b$ are independently selected from hydrogen, methyl, methoxy, hydroxy, chloro, fluoro, difluoromethyl, trifluoromethyl, difluoromethoxy, and trifluoromethoxy and $R^c$ is selected from hydrogen, methyl, cyano, chloro, fluoro, difluoromethyl, trifluoromethyl, difluoromethoxy, and trifluoromethoxy.

32. In embodiment 32, the method of any one of embodiments 1 to 31, wherein the compound of Formulae (I), (IIa1), (IIb1), (IIa1'), (IIb1'), (IIa), (IIb), (IIa'), (IIb') and (IVa) or a pharmaceutically acceptable salt thereof, is wherein $R^7$ is hydrogen, methyl, ethyl, methoxy, fluoro, trifluoromethyl, or trifluoromethoxy, preferably $R^7$ is hydrogen.

33. In embodiment 33, the method of any one of embodiments 1 to 32, is wherein the compound of Formulae (I), (IIa1), (IIb1), (IIa1'), (IIb1'), (IIa), (IIb), (IIa'), (IIb') and (IVa) or a pharmaceutically acceptable salt thereof, is wherein $R^2$ is hydrogen, fluoro, methyl or ethyl.

34. In embodiment 34, the method of any one of embodiments 1 to 33, is wherein the compound of Formulae (I), (IIa1), (IIb1), (IIa1'), (IIb1'), (IIa), (IIb), (IIa'), (IIb') and (IVa) or a pharmaceutically acceptable salt thereof, is wherein $R^9$ is hydrogen, alkyl, halo, hydroxy, or alkoxy.

35. In embodiment 35, the method of any one of embodiments 1 to 33, is wherein the compound of Formulae (I), (IIa1), (IIb1), (IIa1'), (IIb1'), (IIa), (IIb), (IIa'), (IIb') and (IVa) or a pharmaceutically acceptable salt thereof, is wherein $R^9$ is hydrogen, methyl, methoxy, or fluoro.

36. In embodiment 36, the method of embodiment 1 to 35, is wherein the compound of Formulae (I), (IIa1), (IIb1), (IIa1'), (IIb1'), (IIa), (IIb), (IIa'), (IIb') and (IVa) or a pharmaceutically acceptable salt thereof, is wherein $R^2$ and $R^9$ are attached to the ring carbon atom that is meta to the ring carbon attached to $R^1$.

37. In embodiment 37, the method of any one of embodiments 28 or 31, is wherein the compound is a compound of Formula (I) or a pharmaceutically acceptable salt thereof and has the structure of formula (VIIIa1) or (VIIIb1):

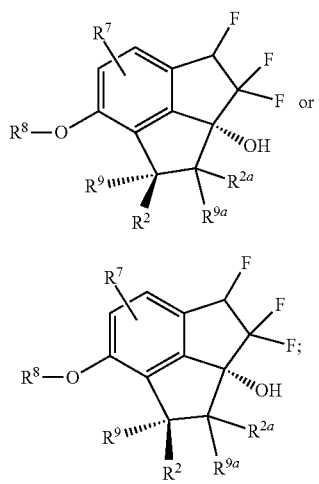

preferably the structure of formula (VIIIb).

38. In embodiment 38, the method of embodiment 37, is wherein the compound of Formula (I) or a pharmaceutically acceptable salt thereof, is wherein $R^2$ is hydrogen or deuterium, $R^9$ is hydrogen, fluoro, or methyl and $R^{2a}$ and $R^{9a}$ are independently hydrogen, deuterium or fluoro.

39. In embodiment 39, the method of embodiment 1, is wherein the compound of Formula (I) is selected from:
3-fluoro-5-((3,3,4,4-tetrafluoro-2a-hydroxy-1-methylene-2, 2a,3,4-tetrahydro-1H-cyclopenta[cd]inden-7-yl)oxy)benzonitrile;
3-fluoro-5-((3,3,4,4-tetrafluoro-2a-hydroxy-1-oxo-2,2a,3,4-tetrahydro-1H-cyclopenta[cd]inden-7-yl)oxy)benzonitrile;
3-fluoro-5-((3,3,4,4-tetrafluoro-1,2a-dihydroxy-2,2a,3,4-tetrahydro-1H-cyclopenta[cd]inden-7-yl)oxy)benzonitrile;
3-fluoro-5-((1,3,3,4,4-pentafluoro-2a-hydroxy-2,2a,3,4-tetrahydro-1H-cyclopenta[cd]inden-7-yl)oxy)benzonitrile;
3-fluoro-5-(((1S,2aR)-1,3,3,4,4-pentafluoro-2a-hydroxy-2, 2a,3,4-tetrahydro-1H-cyclopenta[cd]inden-7-yl)oxy)benzonitrile;
3-fluoro-5-(((1R,2aS)-1,3,3,4,4-pentafluoro-2a-hydroxy-2, 2a,3,4-tetrahydro-1H-cyclopenta[cd]inden-7-yl)oxy)benzonitrile;
3-fluoro-5-(((1R,2aR)-1,3,3,4,4-pentafluoro-2a-hydroxy-2, 2a,3,4-tetrahydro-1H-cyclopenta[cd]inden-7-yl)oxy)benzonitrile;
1,3,3,4,4-pentafluoro-7-((5-fluoropyridin-3-yl)oxy)-1,2,3,4-tetrahydro-2aH-cyclopenta[cd]inden-2a-ol;
3-fluoro-5-((3,3,4,4-tetrafluoro-2a-hydroxy-2,2a,3,4-tetrahydrospiro[cyclopenta[cd]-indene-1,1'-cyclopropan]-7-yl)oxy)benzonitrile;
3-fluoro-5-((3,3,4,4-tetrafluoro-2a-hydroxy-1-methyl-2,2a, 3,4-tetrahydro-1H-cyclopenta[cd]inden-7-yl)oxy)benzonitrile;
3-fluoro-5-((3,3,4,4-tetrafluoro-1,2a-dihydroxy-1-methyl-2, 2a,3,4-tetrahydro-1H-cyclopenta[cd]inden-7-yl)oxy)benzonitrile;
3-fluoro-5-((1,3,3,4,4-pentafluoro-2a-hydroxy-1-methyl-2, 2a,3,4-tetrahydro-1H-cyclopenta[cd]inden-7-yl)oxy)benzonitrile;
3-fluoro-5-((3,3,4,4-tetrafluoro-2a-hydroxy-2,2a,3,4-tetrahydro-1H-cyclopenta[cd]inden-7-yl)oxy)benzonitrile;
3-((2a-amino-1,3,3,4,4-pentafluoro-2,2a,3,4-tetrahydro-1H-cyclopenta[cd]inden-7-yl)oxy)-5-fluorobenzonitrile;
3-fluoro-5-((1,1,2a,3,3,4,4-heptafluoro-2,2a,3,4-tetrahydro-1H-cyclopenta[cd]inden-7-yl)oxy)benzonitrile;
3-((3,3-difluoro-2a-hydroxy-1-methylene-2,2a,3,4-tetrahydro-1H-cyclopenta[cd]inden-5-yl)oxy)-5-fluorobenzonitrile;
3-((3,3-difluoro-2a-hydroxy-1-oxo-2,2a,3,4-tetrahydro-1H-cyclopenta[cd]inden-5-yl)oxy)-5-fluorobenzonitrile;
3-((3,3-difluoro-1,2a-dihydroxy-2,2a,3,4-tetrahydro-1H-cyclopenta[cd]inden-5-yl)oxy)-5-fluorobenzonitrile;
3-fluoro-5-((1,3,3-trifluoro-2a-hydroxy-2,2a,3,4-tetrahydro-1H-cyclopenta[cd]inden-5-yl)oxy)benzonitrile;
3-fluoro-5-((1,2,2,3,3,4,4-heptafluoro-2a-hydroxy-2,2a,3,4-tetrahydro-1H-cyclopenta[cd]-inden-7-yl)oxy)benzonitrile;
3-fluoro-5-(((1S,2aR)-1,3,3,4,4-pentafluoro-2a-hydroxy-2, 2a,3,4-tetrahydro-1H-cyclo-penta[cd]inden-7-yl-1,2,2-d3)oxy)benzonitrile;
3-fluoro-5-(((1S,2aR)-1,3,3,4,4-pentafluoro-2a-hydroxy-2, 2a,3,4-tetrahydro-1H-cyclo-penta[cd]inden-7-yl-1-d) oxy)benzonitrile-2,4,6-d3;
(R)-3-fluoro-5-((3,3,4,4-tetrafluoro-2a-hydroxy-1-methylene-2,2a,3,4-tetrahydro-1H-cyclopenta[cd]inden-7-yl) oxy)benzonitrile;
(S)-3-fluoro-5-((3,3,4,4-tetrafluoro-2a-hydroxy-1-methylene-2,2a,3,4-tetrahydro-1H-cyclopenta[cd]inden-7-yl) oxy)benzonitrile;
3-fluoro-5-(((1R,2S,2aS)-1,2,3,3,4,4-hexafluoro-2a-hydroxy-2,2a,3,4-tetrahydro-1H-cyclopenta[cd] inden-7-yl) oxy)benzonitrile; and
3-fluoro-5-(((1R,2R,2aS)-1,2,3,3,4,4-hexafluoro-2a-hydroxy-2,2a,3,4-tetrahydro-1H-cyclopenta[cd] inden-7-yl) oxy)benzonitrile; or
a pharmaceutically acceptable salt thereof.

40. In embodiment 40, the method of embodiment 1, is wherein the compound of Formula (I) is selected from:
3-fluoro-5-((1,3,3,4,4-pentafluoro-2a-hydroxy-2,2a,3,4-tetrahydro-1H-cyclopenta-[cd]inden-7-yl)oxy)benzonitrile;
3-fluoro-5-(((1S,2aR)-1,3,3,4,4-pentafluoro-2a-hydroxy-2, 2a,3,4-tetrahydro-1H-cyclopenta[cd]inden-7-yl)oxy)benzonitrile; and
a pharmaceutically acceptable salt thereof.

41. In embodiment 41, the method of embodiment 1, is wherein the compound of Formula (I) is 3-fluoro-5-(((1S, 2aR)-1,3,3,4,4-pentafluoro-2a-hydroxy-2,2a,3,4-tetrahydro-1H-cyclopenta[cd]inden-7-yl)oxy)-benzonitrile.

42. In embodiment 42, the method of embodiment 1, is wherein the compound of Formula (I) is 3-fluoro-5-((1,3,3, 4,4-pentafluoro-2a-hydroxy-2,2a,3,4-tetrahydro-1H-cyclopenta[cd]inden-7-yl)oxy)-benzonitrile.

46. In embodiment 46, the method of any one embodiments 1 to 46, is wherein the PARP inhibitor is olaparib (4-[(3-[(4-cyclopropylcarbonyl)piperazin-1-yl]carbonyl)-4-fluorophenyl]methyl(2H)-phthalazin-1-one), rucaparib (8-fluoro-2-{4-[(methylamino)-methyl]phenyl}-1,3,4,5-tetrahydro-6H-azepino[5,4,3-cd]indol-6-one), niraparib (2-[4-[(3S)-3-piperidyl]phenyl]indazole-7-carboxamide), talazoparib ((8S,9R)-5-fluoro-8-(4-fluorophenyl)-9-(1-methyl-1H-1,2,4-triazol-5-yl)-2,7,8,9-tetrahydro-3H-pyrido[4,3,2-de]phthalazin-3-one), or pamiparib ((2R)-14-fluoro-2-methyl-6,9,10,19-tetrazapentacyclo[14.2.1.0$^{2,6}$.0$^{8,18}$.0$^{12,17}$] nonadeca-1(18),8,12(17),13,15-pentaen-11-one; trihydrate).

47. In embodiment 47, the method of any one of embodiments 1 to 46, is wherein the cancer is selected from renal cancer, glioblastoma, neuroblastoma, paraganglioma, pheochromocytoma, somatostatinomas, hemangioblastomas, gastrointestinal stromal tumors, pituitary tumors, leiomyomas, leiomyosarcomas, polycythaemia, retinal cancers, lung cancer, pancreatic cancer, liver cancer, ovarian cancer, breast cancer, prostate cancer, colorectal cancer, head and neck cancer, cervical cancer, endometrial cancer, bladder cancer, gastric cancer, esophageal cancer, lymphoma, melanoma, mesothelioma, sarcoma and neuroendocrine tumors.

48. In embodiment 48, the method of embodiment 47, wherein the cancer is clear cell renal cancer.

49. In embodiment 49, the method of any one of embodiments 1 to 46, is wherein the cancer is selected from ovarian cancer, breast cancer, prostate cancer, renal cancer, colorectal cancer, uveal melanoma, pancreatic cancer, urothelial cancer, endometrial cancer, lung cancer, lymphoma, head and neck cancer, fallopian tube cancer, primary peritoneal cancer, cervical cancer, melanoma, esophageal cancer, gastric cancer, mesothelioma, cholangiocarcinoma, glioblastoma, Ewing Sarcoma, uterine leiomyosarcoma, chronic lymphocytic leukemia, T-cell-prolymphocytic leukemia, multiple myeloma, acute myeloid leukemia, chronic myelogenous leukemia, germ cell cancer, bladder cancer, neuroendocrine tumors, osteosarcoma, biliary tract cancer, soft-tissue sarcoma, rhabdomyosarcoma, mantle-cell lymphoma, and endocrine gland neoplasms.

50. In embodiment 50, the method of any one of embodiments 1 to 49, is wherein the compound of Formula (I) and the PARP inhibitor are administered sequentially or simultaneously.

51. In embodiment 51, the method of any one of embodiments 1 to 50, is wherein the combination is a synergistic combination.

52. In embodiment 52, the method of any one of embodiments 1 to 51, is wherein the method further comprises administering one or more additional anti-cancer agents.

EMBODIMENTS A

A1. In embodiment A1, provided is a compound of Formula (IA), or a pharmaceutically acceptable salt thereof, as provided in the fifth aspect in the Summary of this Application.

A2. In embodiment A2, the compound of (IA), or a pharmaceutically acceptable salt thereof, has a structure according to Formula (IA'):

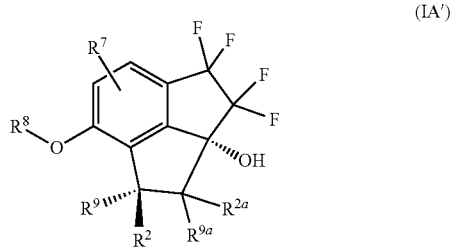

(IA')

A3. In embodiment A3, the compound of embodiment A1 or A2, or a pharmaceutically acceptable salt thereof, is wherein $R^a$, $R^b$, and $R^c$ are independently selected from hydrogen, deuterium, alkyl, alkoxy, hydroxy, halo, haloalkyl, haloalkoxy, and cyano.

A4. In embodiment A4, the compound of embodiment A1 or A2, or a pharmaceutically acceptable salt thereof, is wherein $R^a$, $R^b$, and $R^c$ are independently selected from hydrogen, deuterium, methyl, methoxy, hydroxy, chloro, fluoro, cyano, difluoromethyl, trifluoromethyl, difluoromethoxy, and trifluoromethoxy and $R^g$ and $R^h$ are independently hydrogen or deuterium.

A5. In embodiment A5, the compound of embodiment A1 or A2, or a pharmaceutically acceptable salt thereof, is wherein $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, 3-cyano-5-difluoromethylphenyl or 3-cyano-5-fluoro-2,4,6-trideuteriophenyl.

A6. In embodiment A6, the compound of embodiment A1 or A2, or a pharmaceutically acceptable salt thereof, is wherein $R^8$ is 3-cyano-5-fluorophenyl or 3-cyano-5-fluoro-2,4,6-trideuteriophenyl.

A7. In embodiment A7, the compound of embodiment A1 or A2 is selected from:
3-fluoro-5-(((1R,2S,2aS)-1,2,3,3,4,4-hexafluoro-2a-hydroxy-2,2a,3,4-tetrahydro-1H-cyclopenta[cd] inden-7-yl) oxy)benzonitrile; and
3-fluoro-5-(((1R,2R,2aS)-1,2,3,3,4,4-hexafluoro-2a-hydroxy-2,2a,3,4-tetrahydro-1H-cyclopenta[cd] inden-7-yl) oxy)benzonitrile; or
a pharmaceutically acceptable salt thereof.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where $X^1$ is CH, $R^1$ is hydroxyl, $R^3$, $R^4$, $R^5$, $R^6$, $R^7$, and $R^8$ are as defined in the Summary (or any embodiments thereof), and $R^9$ and $R^2$ are combined to form alkyldienyl, can be prepared as illustrated and described in Scheme 1 below.

Scheme 1

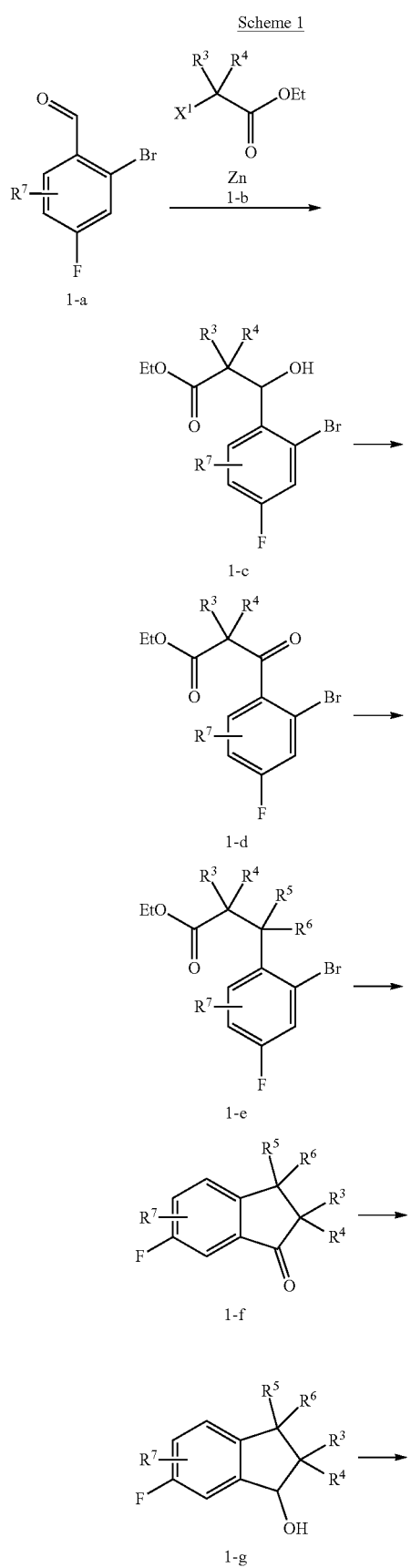

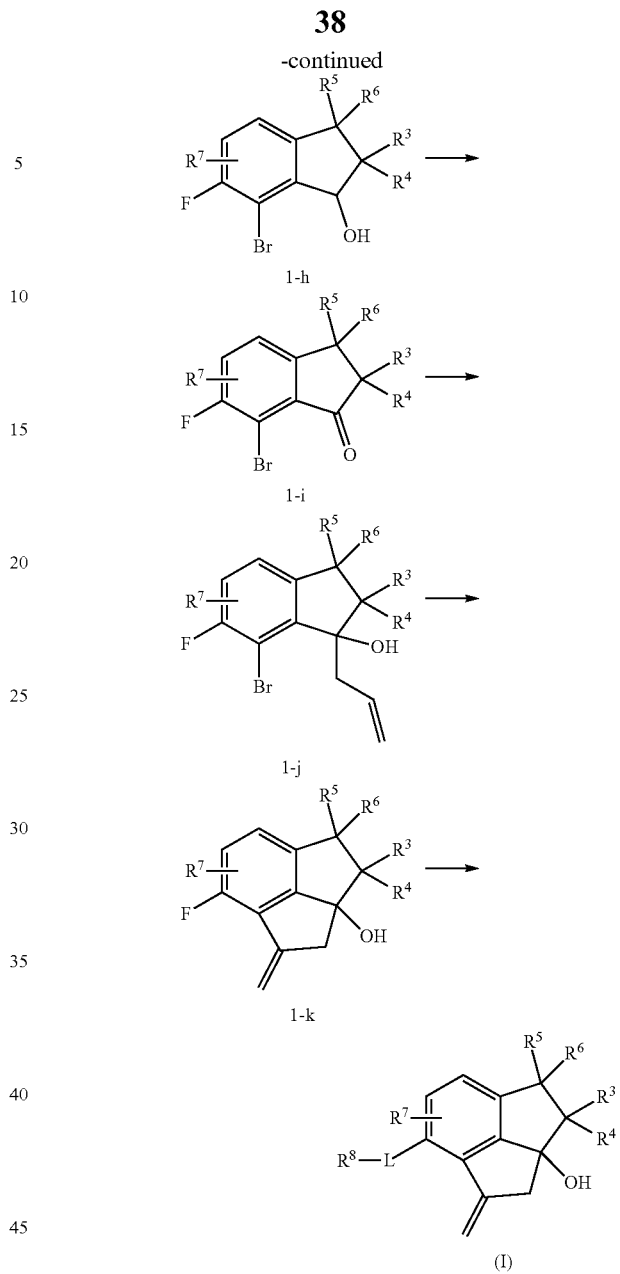

Reformastky reaction between an aldehyde of formula 1-a where R⁷ is as described in the Summary or a precursor group thereof and a compound of formula 1-b where $X^1$ is halide and $R^3$ is as defined, e.g., independently hydrogen, deuterium, alkyl, halo, haloalkyl, hydroxyalkyl, or alkoxyalkyl, mediated by zinc metal provides a compound of formula 1-c. Compounds of formula 1-a and 1-b are commercially available or they can be prepared by methods well known in the art. For example, 2-bromo-4-fluorobenzaldehyde, ethyl 2-bromo-2,2-difluoroacetate, ethyl 2-bromo-2-methylpropanoate, ethyl 2-bromopropanoate, ethyl 2-bromoacetate are commercially available. The hydroxyl group in 1-c can be oxidized under oxidative conditions such as 2-iodoxybenzoic acid (IBX) or TPAP, NMO to give a ketone of formula 1-d. The keto group in compound of formula 1-d can be functionalized to provide compound of formula 1-e where $R^5$ and $R^6$ are as described in the Summary by methods well known in the art. For example, a compound of formula 1-e where $R^5$ and $R^6$ are fluoro can be synthesized from 1-d by treatment with a fluorinating agent such as DAST or $SF_4$ under conditions well known in the art. Cyclization of 1-e can be achieved by treating it with alkyl lithium reagent such n-BuLi to give ketone 1-f. The carbonyl group in 1-f can be reduced with reducing reagents such as $NaBH_4$ to provide alcohol 1-g.

Compounds of formula 1-g can be converted to compounds of formula 1-h by lithiation of 1-g, followed by treating the lithio intermediate with $CBr_4$. Oxidation of 1-h with oxidative reagents such as IBX provides ketone of formula 1-i. Addition of allyl metal reagent such as allyl magnesium bromide to compounds of formula 1-i provides compounds of formula 1-j.

Alternatively, compound of formula 1-j can be prepared from 1-f by addition of allyl metal reagent such as allyl magnesium bromide to compounds of formula 1-f illustrated below:

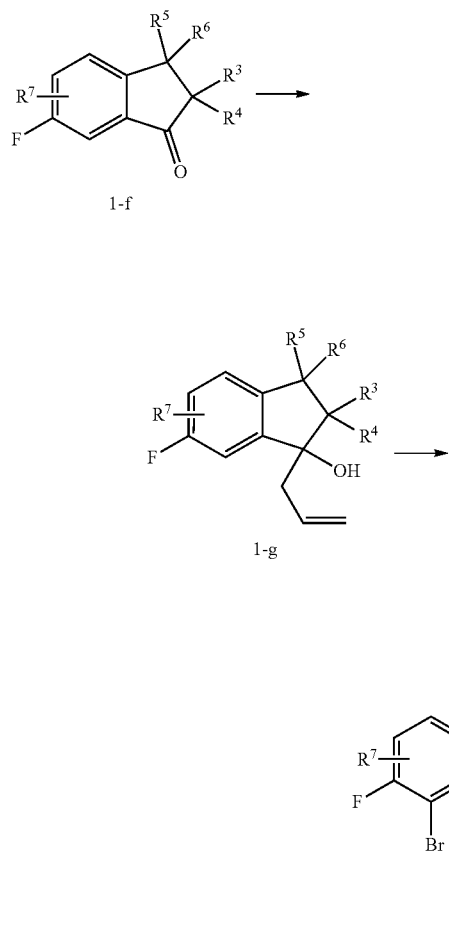

Lithiation of 1-g with bases such LDA followed by treating the lithio intermediate with bromination reagent such as $CBr_4$ or 1,2-dibromotetrafluoroethane provides compound of formula 1-j. If desired, enantioselective synthesis of compounds of formula 1-g can be achieved by addition of 2-allyl-4,4,5,5-tetramethyl-1,3,2-dioxaborolane to compounds of formula 1-f in the presence of a ligand such as 1-m and a suitable base such as tBuONa in organic solvents such as MeOH, toluene as depicted below:

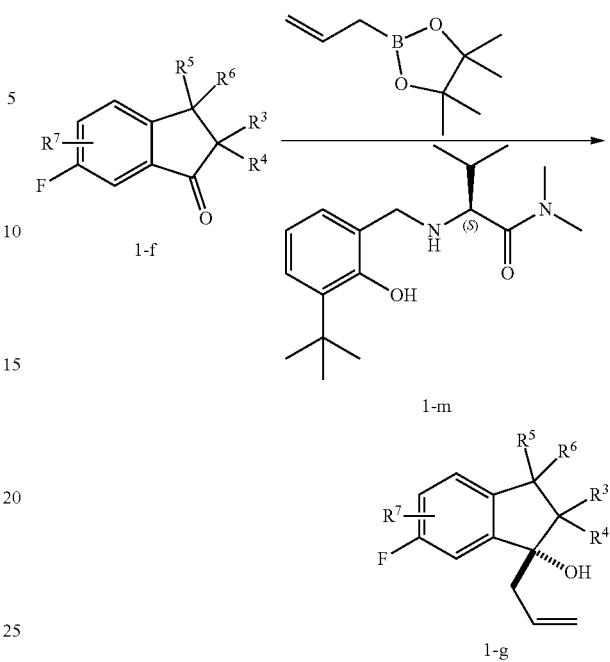

Compounds of formula 1-j can undergo cyclization in the presence of Pd catalyst with suitable ligands such as $Pd(dppf)Cl_2 \cdot CH_2Cl_2$ or $Pd(PPh_3)_2Cl_2$ to provide compounds of formula 1-k. The fluoro group in compounds of formula 1-k can be converted to a group of formula-L-$R^8$ where L and $R^8$ are as described in the Summary by treating compound 1-k with a compound of formula $R^8$-LH where L is N, O, or S and $R^8$ is a defined in the Summary by method well known in the art. Compounds of formula $R^8$-LH are commercially available or they can be prepared by methods well known in the art. For example, 3-fluoro-5-hydroxybenzonitrile, 3,5-difluorophenol, 3-chloro-5-fluorophenol, 3-chloro-5-hydroxy-benzonitrile, 5-fluoropyridin-3-ol, 5-chloropyridin-3-ol, 5-hydroxynicotinonitrile, 3-fluoro-5-mercaptobenzonitrile, 3-amino-5-fluorobenzonitrile, 3,3-difluorocyclobutan-1-ol, 3-amino-5-fluorobenzonitrile, 3-fluoro-5-mercaptobenzonitrile, 3-chloro-5-mercaptobenzonitrile, 3-amino-5-chlorobenzonitrile are commercially available.

Compounds of Formula (I) where $R^1$ is hydroxyl, $R^3$, $R^4$, $R^5$, $R^6$, $R^7$, and $R^8$ are as defined in the Summary (or any embodiments thereof), and $R^9$ and $R^2$ are combined to form oxo can be prepared as illustrated and described in Scheme 2 below.

Scheme 2

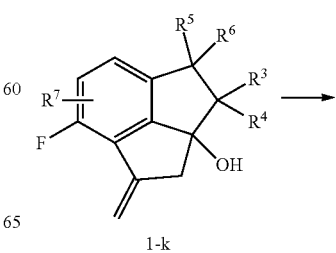

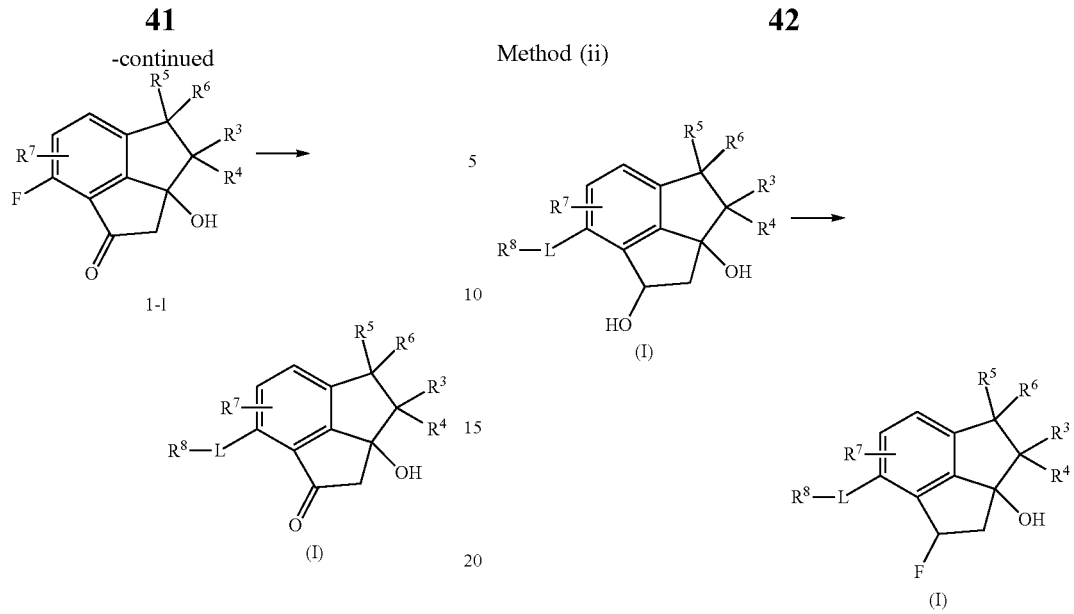

Compounds of Formula 1-k can be converted to compounds of Formula 1-l by treating it with an oxidative cleavage reagent such as NaIO$_4$ and RuCl$_3$ hydrate under conditions well known in the art. The fluoro group in compounds of Formula 1-l can be converted to a group of formula-L-R$^8$ where L and R$^8$ are as described in the Summary by treating compound 1-l with a compound of formula R$^8$-LH.

Compounds of Formula (I) can be converted to other compounds of Formula (I) by methods well known in the art. For example, compounds of Formula (I) where with R$^1$ is hydroxyl, R$^2$ is hydrogen and R$^9$ is hydroxy or fluoro can be synthesized from the compounds of Formula (I) where R$^9$ and R$^2$ are combined to form oxo by further functionalizing the carbonyl group as illustrated and described in Methods (i) and (ii) below.

Method (i)

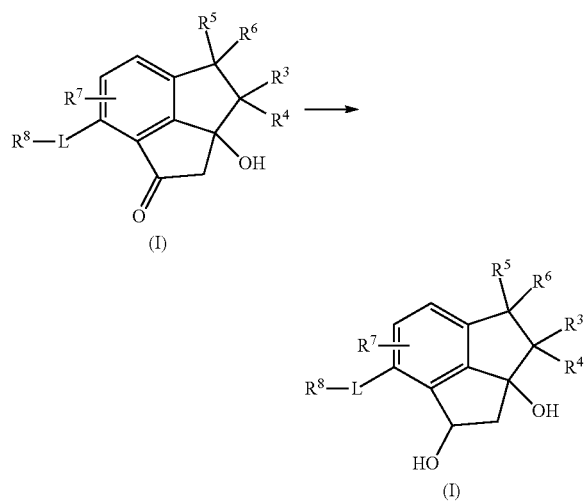

A compound of Formula (I) where R$^1$ is hydroxy, R$^9$ and R$^2$ are combined to form oxo can be converted to a compound of Formula (I) where R$^1$ is hydroxy, R$^9$ is hydroxy by treating it with reducing reagent such as sodium borohydride under conditions well known in the art.

Method (ii)

A compound of Formula (I) where R$^1$ is hydroxy, R$^9$ is hydroxy can be converted to a compound of Formula (I) where R$^1$ is hydroxy, R$^9$ is fluoro by treating it with fluorination reagent such as DAST under conditions well known in the art.

Utility

HIF-2α plays an important role in the initiation and progression of many human cancers. Many extensive studies have demonstrated the critical role of increased HIF-2α activity in driving clear cell renal cell carcinoma (ccRCC) (see review by Shen and Kaelin, Seminars in Cancer Biology 23: 18-25, 2013). Abnormal HIF-2α activity is largely due to loss of function of a tumor suppressor, VHL. It is known that over eighty percent of ccRCC have defective VHL either through deletion, mutation or disturbed post-translational modification. Defective VHL leads to constitutively active HIF-α proteins regardless of oxygen level. Various studies employing gain-of-function and loss-of-function approaches in mouse models have demonstrated that HIF-2α is the key oncogenic substrate of VHL (see Kondo, et al. Cancer Cell 1: 237-246, 2002; Kondo, et al. PLoS Biology 1: 439-444, 2002; Maranchi, et al. Cancer Cell 1: 247-255, 2002; Zimmer, et al. Mol. Cancer Res 2: 89-95, 2004). For example, knockdown of HIF-2α in VHL-null tumors inhibited tumor formation, while reintroduction of VHL and overexpression of HIF-2α overcame the tumor suppressive role of VHL. Moreover, single nucleotide polymorphism in HIF-2α, is associated with resistant to PHD-mediated degradation, has been linked to an increased risk of developing RCC. In addition to serving as an archetypical tumor-initiating event in ccRCC, the VHL-HIF-2α axis has also been implicated in ccRCC tumor metastasis through its downstream CXCR4 and CYTIP (see Vanharanta et al. Nature Medicine 19: 50-59, 2013; Peter Staller et al. Nature. 2003 Sep. 18; 425(6955):307-11). Taken together, these studies strongly support the potential therapeutic utility of HIF-2α targeted agents for the treatment of ccRCC.

Defective VHL not only predisposes patients to kidney cancer (with a 70% lifetime risk), but also to hemangioblastomas, pheochromocytoma, endolymphatic sac tumors and pancreatic neuroendocrine tumors. Tumors derived from defective VHL are frequently driven by the constitutively active downstream HIF-α proteins, with the majority of these dependent on HIF-2α activity (see Maher, et al. Eur. J.

Hum. Genet. 19: 617-623, 2011). Both genetic and epigenetic mechanisms can lead to the loss of function in VHL. Epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (see reviewed in Nguyen, et al. Arch. Phann. Res 36: 252-263, 2013). HIF-2α has also been linked to cancers of the retina, adrenal gland and pancreas through both loss of function in VHL and activating mutations in HIF-2α. Recently, gain-of-function HIF-2α mutations have been identified in erythrocytosis and paraganglioma with polycythemia (see Zhuang, et al. NEJM 367: 922-930, 2012; Percy, et al. NEJM 358: 162-168, 2008; and Percy, et al. Am. J. Hematol. 87: 439-442, 2012). Notably, many of the known HIF-2α target gene products (e.g., VEGF, PDGF, and cyclin Dl) have been demonstrated to play pivotal roles in cancers derived from kidney, liver, colon, lung, and brain. Thus, a HIF-2α targeted therapy could be beneficial for the above cancers when driven by these signaling events downstream of abnormal HIF-2α pathway activation. In addition to loss of function in VHL and activating mutation of HIF-2α, HIF-α proteins are also frequently upregulated in the intratumor environment of rapidly growing tumors, due to the hypoxic condition resulting from poor vascularization in large tumors. The activated HIF-α pathways, in turn, further promotes tumor cell survival and proliferation by transcriptionally upregulating various essential factors.

A large body of studies have demonstrated a correlation between HIF-2α overexpression and poor prognosis in various cancers including cancers of astrocytoma, breast, cervical, colorectal, glioblastoma, glioma, head and neck, liver, non-small cell lung, melanoma, neuroblastoma, ovarian, and prostate, thereby supporting the pursuit of HIF-2α as a therapeutic target in treating these cancers (see reviewed in Keith, et al. Nature Rev. Cancer 12: 9-22, 2012). HIF-2α has been demonstrated to augment the growth of APC mutant colorectal cancer through its regulation of genes involved in proliferation, iron utilization and inflammation (see Xue, et al. Cancer Res 72: 2285-2293, 2012; and Xue and Shah, Carcinogenesis 32: 163-169, 2013). In hepatocellular carcinoma (HCC), knock-down of HIF-2α in preclinical models led to the inhibition of cell proliferation in vitro and tumor growth in vivo through the downregulation of VEGF and cyclin D 1 (see He, et al. Cancer Sci. 103: 528-534, 2012). In NSCLC, around 50% of patients exhibited overexpression of HIF-2α protein, which strongly correlates with higher VEGF expression and more importantly, reduced overall survival. Interestingly, HIF-1α does not correlate with reduced overall survival in lung cancer patients even though its expression is also often increased (see Giatromanolaki, et al. Br. J. Cancer 85: 881-890, 2001). Extensive studies in mice engineered with both non-degradable HIF-2α and mutant KRAS tumors have demonstrated an increased tumor burden and a decreased survival when compared to mice with only mutant KRAS expression (see Kim, et al. J. Clin. Invest. 119: 2160-2170, 2009). These studies demonstrate that HIF-2α promotes tumor growth and progression in lung cancer, and also negatively correlates with clinical prognosis.

HIF-2α activity has also been demonstrated to be important in cancers of the central nervous system (see Holmquist-Mengelbier, et al. Cancer Cell 10: 413-423, 2006 and Li, et al. Cancer Cell 15: 501-513, 2009). HIF-2α knockdown reduced tumor growth in preclinical animal models of neuroblastoma, Conversely, increased level of HIF-2α correlated with advanced disease, poor prognosis and higher VEGF levels, which likely contribute to the poor clinical outcome. Similarly, higher HIF-2α expression has been correlated with a poor survival in glioma. Experimentally, inhibition of HIF-2α in glioma stem cells reduced cell proliferation and survival in vitro and tumor initiation in vivo. While HIF-1α is expressed in both neural progenitors and brain tumor stem cells, HIF-2α is found exclusively in the latter. Moreover, survival of glioma patients correlates to with HIF-2α, but not HIF-1α level.

Somatostatinomas are somatostatin-producing neuroendocrine tumors that are rare, but often malignant. It has been found that HIF-2α mutations lead to the disruption of the prolyl hydroxylation domain (PHD) of HIF-2α, thus abolish the modification by PHDs, and subsequently reduce HIF-2α degradation mediated by VHL (see Yang, et al. Blood. 121: 2563-2566, 2013). The stabilized HIF-2α can then translocate to the nucleus, driving increased expression of hypoxia-related genes to contribute to somatostatinoma. Thus, a HIF-2α inhibitor will provide an alternative approach in treating somatostatinoma.

Pheochromocytomas and paragangliomas (PPGLs) are rare neuroendocrine tumors that often develop on a background of predisposing genetic mutations, including loss of function in VHL or PHD2 or activating mutations of HIF-2α, all of which result in highly expressed HIF-2α protein and subsequently downstream genes to promote oncogenic progression (see Dahia, Nat Rev Cancer. 14:108-19, 2014). Furthermore, germline heterozygous mutations in genes encoding succinate dehydrogenase (SDH) subunits and the SDH complex assembly factor 2 protein (SDHAF2) have been described in patients with hereditary phaeochromocytoma and paraganglioma (PPGL). These mutations can lead to the accumulation of succinate, which in turn causes an inhibition of prolyl-hydroxylases that is essential in mediating ubiquitination/degradation of HIF proteins by VHL complex. Pituitary adenoma has been frequently found to be co-existing with PPGLs. Thus, inhibiting HIF-2α should be useful for treating both PPGLs and pituitary tumors. Succinate dehydrogenase subunits mutations have also been associated with gastrointestinal stromal tumors (GIST), thus supporting exploration of HIF-2α inhibitor for the treatment of GIST (see Janeway, et al. Proc. Natl Acad. Sci. USA 108: 314-318, 2011).

Loss-of-function mutations of fumarate hydratase (FH) predispose patients to the autosomal dominant syndrome of both cutaneous and uterine leiomyomatosis. It has been suggested that activation of HIF proteins contributes to FH-associated tumor development by activation of hypoxia pathways. (see O'Flaherty, et al. Hum Mol Genet. 19: 3844-3851, 2010 and Wei, et al. J Med Genet. 43:18-27, 2006). Furthermore, high expression of HIF-2α is found in leiomyosarcomas, a rare neoplasm of smooth-muscle origin (see Mayer, et al. Cancer Res. 68: 4719, 2008). Thus, inhibition of HIF-2α could be beneficial in treating both leiomyomas and leiomyosarcomas.

Retinal capillary hemangioblastomas can be the ocular manifestations of VHL diseases, which are caused by loss of tumor suppressor VHL. Upregulation of HIF-2α upon loss of VHL has been detected in retinal hemangioblastoma patients and is indicated to contribute to the aggressive course of retinal hemangioblastomas, resulting in the resistance to multiple anti-VEGF and radiation therapies (see Wang, et al. Graefes Arch. Clin. Exp. Ophthalmol. 252: 1319-1327, 2014).

In addition to a direct role in promoting the initiation, progression and metastasis of tumor cells (e.g. ccRCC), HIF-2α also indirectly contributes to tumorigenesis through augmenting the immunosuppressive effect of hypoxia within the tumor microenvironment. Expression of HIF-2α has been detected in cells of the myeloid lineage (see Talks K L, et dal. Am J Pathol. 2000; 157(2):411-421). For example, HIF-2α is shown to favor the polarization of macrophages to the immunosuppressive M2 phenotype and enhances migration and invasion of tumor-associated macrophages (see Imtiyaz H Z et al. J Clin Invest. 2010; 120(8):2699-2714). Thus, increased level of HIF-2α in tumor-associated macrophages (TAMs) is associated with high-grade human tumors and correlates with poor prognosis. Furthermore, HIF-2α can indirectly promote additional immunosuppressive pathways (e.g. adenosine and arginase etc.) by modulating the expression of key signaling regulators such as adenosine A2B/A2A receptors and arginase. These data support that HIF-2α is a potential therapeutic target for treating a broader range of inflammatory disorders and cancer either as a single agent or in combination with other therapeutic agents e.g., immunotherapies.

In addition, the HIF-2α compounds can be used as single agents for the treatment of cartilage cancer(s), skin cancer (s), salivary gland cancer, gastric cancer, stomach cancer, liver cancer, endometrial cancer, bladder cancer, mesothelioma, sarcoma, esophageal cancer, lymphoma, uveal melanoma, urothelial cancer, fallopian tube cancer, primary peritoneal cancer, cholangiocarcinoma, Ewing Sarcoma, uterine leiomyosarcoma, chronic lymphocytic leukemia, acute lymphocytic leukemia, T-cell-prolymphocytic leukemia, chronic myelogenous leukemia, germ cell cancer, osteosarcoma, biliary tract cancer, soft-tissue sarcoma, rhabdomyosarcoma, mantle-cell lymphoma, and endocrine gland neoplasms.

In addition, HIF-2α inhibitors, for example, compound 24a or 24b disclosed herein, can be used in the treatment of non-oncology indications such as pulmonary arterial hypertension (PAH), NASH, inflammatory bowel disease (IBD), or iron overload.

Testing

The HIF-2α inhibitory activity of the compounds of the present disclosure can be tested using the in vitro assay described in Biological Example 1 below. The ability of the HIF-2α compounds of this disclosure to inhibit heterodimerization of HIF-2α to HIF-1beta (ARNT) can be tested using the in vitro assay described in Example 2 below. The ability of the HIF-2α compounds of this disclosure to prevent or treat PAH can be determined using the hypoxia induced PAH in vivo models described in Examples 36 and 37 of PCT application publication No. WO2016145032. The anti-proliferative effect of a HIF-2α inhibitor in combination with a PARP inhibitor in ccRCC cancer can be evaluated using the in vitro assay described in Biological Example 3 below.

Pharmaceutical Compositions

In general, the HIF-2α of this disclosure and the PARP inhibitors will be administered in a therapeutically effective amount by any of the accepted modes of administration for agents that serve similar utilities. As single agent, the therapeutically effective amounts of HIF-2α inhibitors disclosed herein may range from about 5 mg to about 500 mg/per day, preferably 10 mg to 200 mg/day, which can be administered in single or multiple doses. For oral administration, the compositions can be provided in the form of tablets or capsules containing about 5.0 to about 500 milligrams, preferably about 5, 10, 20, 50, 75, 100, 150, 200, 250, 300, 400, or 500 milligrams of the of a HIF-2α inhibitor.

For combination therapy, the therapeutically effective amount of a HIF-2α inhibitor may range from about 0.01 to about 100 mg per kg patient body weight per day, which can be administered in single or multiple doses. A suitable dosage level for the HIF-2α inhibitor may be from about 0.1 to about 50 mg/kg per day; about 0.5 to about 15 mg/kg per day. For oral administration, the compositions can be provided in the form of tablets containing about 20 to about 800 milligrams of the HIF-2α inhibitor active ingredient, particularly about 50, 75, 100, 150, 200, 250, 300, 400, 500, 600, 750, 800, 900, and 1000 milligrams of the active ingredient. Therapeutically effective amount a PARP inhibitor for use in the combination therapy may range from about 0.001 to about 100 mg per kg patient body weight per day, which can be administered in single or multiple doses. A suitable dosage level of the PARP inhibitor may be from about 0.001 to about 50 mg/kg per day; 0.003 to about 50 mg/kg per day; about 0.001 to about 20 mg/kg per day; or about 0.001 to about 15 mg/kg per day. For oral administration, the compositions can be provided in the form of tablets containing about 0.25 to about 800 milligrams of the PARP inhibitor active ingredient, particularly about 0.25, 0.5, 1, 50, 75, 100, 150, 200, 250, 300, 400, 500, 600, 750, 800, 900, and 1000 milligrams of the PARP inhibitor active ingredient. In one embodiment, the PARP inhibitor is pamiparib and may be dosed at 20 mg BID, 40 mg BID, or 60 mg BID, or at about 0.5 to about 2 mg/kg/day. In another embodiment, the PARP inhibitor is rucaparib may be dosed at 600 mg PO BID (doses reduced if adverse reactions), or at about 10 to about 20 mg/kg/day. In another embodiment, the PARP inhibitor is olaparib and may be dosed at 300 mg PO BID (doses reduced if adverse reactions), or at about 2.5 to about 10 mg/kg/day. In another embodiment, the PARP inhibitor is niraparib and may be dosed at 300 mg PO Qday (doses reduced if adverse reactions), or at about 1 to about 6 mg/kg/day. In another embodiment, the PARP inhibitor is Talazoparib and may be dosed at 1 mg PO daily (doses reduced if adverse reactions), or at about 0.003 to about 0.14 mg/kg/day.

The actual amount of HIF-2α and/or PARP inhibitors, i.e., the active ingredients, will depend upon numerous factors such as the severity of the disease to be treated, the age and relative health of the patient, the potency of the compound being utilized, the route and form of administration, and other factors.

In general, the HIF-2α and PARP inhibitors of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a HIF-2α and/or PARP inhibitors of this disclosure in combination with at least one pharmaceutically acceptable excipient. Acceptable excipients are non-toxic, aid administration, and do not adversely affect the therapeutic benefit of the HIF-2α and PARP inhibitors. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

The level of the compound in a formulation can vary within the full range employed by those skilled in the art. Typically, the formulation will contain, on a weight percent (wt. %) basis, from about 0.01-99.99 wt. % of a HIF-2α and/or PARP inhibitor(s) based on the total formulation, with the balance being one or more suitable pharmaceutical excipients. For example, the HIF-2α and/or PARP inhibitor(s) is present at a level of about 1-80 wt. %.

The HIF-2α inhibitors disclosed herein can be administered either alone or in combination with a PARP inhibitor with one or more other anti-cancer drugs that are useful in the treatment of cancers for which compounds of this disclosure have utility. Such other drug(s) may be administered, by a route and in an amount commonly used therefore, simultaneously or sequentially with the HIF-2α inhibitor and/or PARP inhibitor(s). It is also contemplated that when used in combination with such one or more other active ingredients, the HIF-2α inhibitor and/or PARP inhibitor and the other active ingredients may be used in lower doses than when each is used singly.

Accordingly, the pharmaceutical compositions of the present disclosure also include those that contain one or more other drugs, in addition to HIF-2α inhibitor(s) and/or PARP inhibitor(s). The weight ratio of the compounds of this disclosure to the such other active ingredient may be varied and will depend upon the effective dose of each ingredient. Generally, an effective dose of each will be used.

Examples of such other anti-cancer agents include, but are not limited to, gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™.

Other anti-cancer agents include inhibitors of kinases associated cell proliferative disorder. These kinases include, but not limited to, Aurora-A, BTK, CDK1, CDK2, CDK3, CDK4, CDK6, CDK5, CDK7, CDK8, CDK9, ephrin receptor kinases, CHK1, CHK2, SRC, Yes, Fyn, Lck, Fer, Fes, Syk, Itk, Bmx, GSK3, JNK, MEK, PAK1, PAK2, PAK3, PAK4, PDK1, PKA, PKC, RAF, Rsk and SGK. In particular, inhibitors of CDK4/6, including abemaciclib (Verzenio), palbociclib (Ibrance) and ribociclib (Kisqali), have the potential to be synergistic with HIF-2α inhibitors and reverse the resistance to HIF-2α inhibition; mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946, BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; CSF1R inhibitors (PLX3397, LY3022855, etc.) and CSF1R antibodies (IMC-054, RG7155, etc); TGF beta receptor kinase inhibitor such as LY2157299; BTK inhibitor such as ibrutinib.

Other anti-cancer agents include proteasome inhibitor such as carfilzomib, MLN9708, delanzomib, or bortezomib; BET inhibitors such as INCB054329, OTX015, CPI-0610; LSD1 inhibitors such as GSK2979552, INCB059872; HDAC inhibitors such as panobinostat, vorinostat; DNA methyl transferase inhibitors such as azacytidine, decitabine, and other epigenetic modulator; SHP-2 inhibitor such as TNO155; Bcl2 inhibitor ABT-199, and other Bcl-2 family protein inhibitors; HIF-2α inhibitors such as PT2977 and PT2385; Beta catenin pathway inhibitors, notch pathway inhibitors and hedgehog pathway inhibitors; Antibodies or other therapeutic proteins against VEGF include bevacizumab and aflibercept.

Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors.

Other anti-cancer agents that can be employed in combination with the compounds of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with the compounds of the disclosure include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with the compounds of present disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with the compounds of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with the compounds of this disclosure include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to, folic acid analog (e.g., methotrexate), or pyrimidine analogs (e.g., fluorouracil, floxuridine, cytarabine), purine analogs (e.g., mercaptopurine, thioguanine, pentostatin).

Examples of hormones and antagonists useful in combination the compounds of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other anti-cancer agents that can be employed in combination with the compounds of the disclosure include: anticancer agents which act by arresting cells in the G2-M phases due to stabilized microtubules and include Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

One or more additional immune checkpoint inhibitors can be used in combination with the compounds of this disclosure. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM, arginase, CD137 (also known as 4-1BB), ICOS, A2AR, A2BR, SHP-2, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from MR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-1 monoclonal antibody. In some embodiments, the anti-PD-1 monoclonal antibody is BMS-935559, MEDI4736, MPDL3280A (also known as RG7446), or MSB0010718C. In some embodiments, the anti-PD-1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

In addition, the combination therapy disclosed herein can be administered along with radiation.

EXAMPLES

The following preparations of compounds of Formula (I) are given to enable those skilled in the art to more clearly understand and to practice the present disclosure. They should not be considered as limiting the scope of the disclosure, but merely as being illustrative and representative thereof.

Example 1

Synthesis of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile

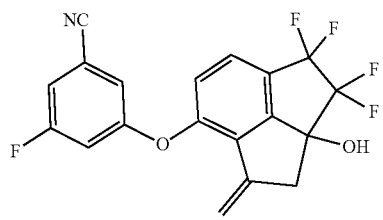 [SMILES: C=C1CC2(O)c3c(ccc(Oc4cc(F)cc(C#N)c4)c31)C(F)(F)C2(F)F]

Step 1: ethyl 3-(2-bromo-4-fluorophenyl)-2,2-difluoro-3-hydroxypropanoate

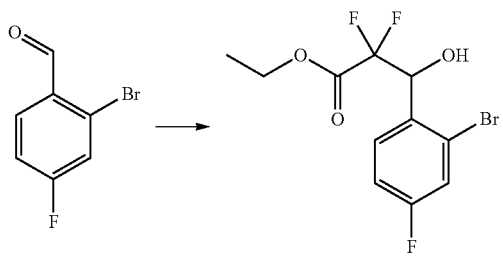 [SMILES: O=Cc1ccc(F)cc1Br ; CCOC(=O)C(F)(F)C(O)c1ccc(F)cc1Br]

To a stirred mixture of zinc (6.97 g, 106.56 mmol, 1.03 equiv.), 1,2-dibromoethane (388.71 mg, 2.069 mmol, 0.02 equiv.) and chlorotrimethylsilane (1.12 g, 10.31 mmol, 0.10 equiv.) in THF (200 mL) was added a solution of ethyl 2-bromo-2,2-difluoroacetate (21.0 g, 103.45 mmol, 1.0 equiv.) and 2-bromo-4-fluorobenzaldehyde (21.0 g, 103.45 mmol, 1.0 equiv.) in THF (100 mL) dropwise at room temperature under nitrogen atmosphere. The resulting mixture was stirred for 16 h at 75° C. under nitrogen atmosphere. The reaction was cooled and quenched with ice/water. The organic solvent was removed under vacuum and the resulting mixture was extracted with EtOAc. The combined organic layer was washed with water, dried over anhydrous Na$_2$SO$_4$ and concentrated under reduced pressure. The residue was purified by silica gel column chromatography, eluted with PE/EtOAc (5:1), to afford the title compound (18 g, 53.2%) as a yellow oil.

Step 2: ethyl 3-(2-bromo-4-fluorophenyl)-2,2-difluoro-3-oxopropanoate

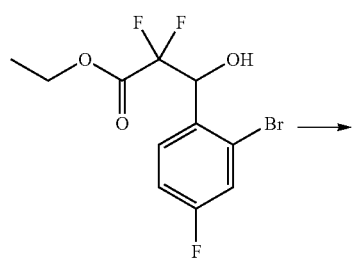

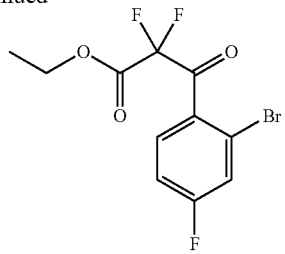

To a stirred solution of ethyl 3-(2-bromo-4-fluorophenyl)-2,2-difluoro-3-hydroxypropanoate (16 g, 48.9 mmol, 1.0 equiv.) in CH$_3$CN (200 mL) was added 2-iodoxybenzoic acid (27.4 g, 97.83 mmol, 2.0 equiv.) at room temperature and the resulting mixture was stirred for 3 h at 80° C. The reaction solution was then cooled to room temperature, filtered and the filter cake was washed with EtOAc. The filtrate was concentrated under reduced pressure. The residue was purified by silica gel column chromatography, eluted with PE/EtOAc (10:1), to afford the title compound (10.3 g, 64.8%) as a yellow oil.

Step 3: ethyl 3-(2-bromo-4-fluorophenyl)-2,2,3,3-tetrafluoropropanoate

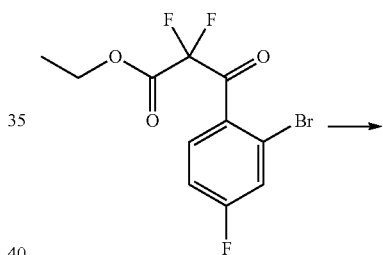

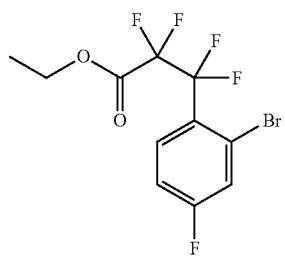

To a stirred solution of ethyl 3-(2-bromo-4-fluorophenyl)-2,2-difluoro-3-oxopropanoate (6.1 g, 18.8 mmol, 1.0 equiv.) in CHCl$_3$ (6 mL) was added DAST (30.25 g, 187.6 mmol, 10.0 equiv.) dropwise at room temperature and the resulting mixture was stirred for 16 h at 70° C. under nitrogen atmosphere. The reaction solution was allowed to cool to room temperature and quenched with ice/water. The mixture was extracted with DCM. The organic layer was dried over anhydrous Na$_2$SO$_4$ and concentrated. The residue was purified by silica gel column chromatography, eluted with PE/EtOAc (10:1), to afford the title compound (2.4 g, 36.8%) as yellow oil.

Step 4:
2,2,3,3,6-pentafluoro-2,3-dihydro-1H-inden-1-one

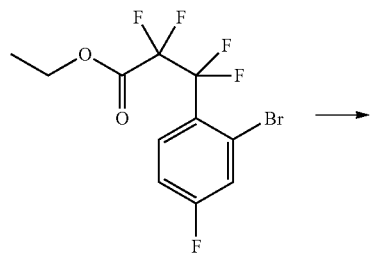

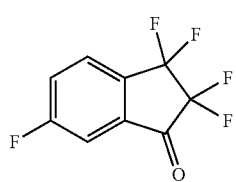

To a stirred solution of ethyl 3-(2-bromo-4-fluorophenyl)-2,2,3,3-tetrafluoropropanoate (4.20 g, 12.10 mmol, 1.0 equiv.) in THF (50 mL) was added n-BuLi (2.5 M, 7.26 mL, 18.15 mmol, 1.5 equiv.) dropwise at −78° C. under nitrogen atmosphere and the resulting mixture was stirred for 2 h between −70° C. and −80° C. under nitrogen atmosphere. The reaction was quenched with saturated NH$_4$Cl (aq.) and extracted with EtOAc. The organic layer was dried over anhydrous Na$_2$SO$_4$ and concentrated under reduced pressure. The residue was purified by silica gel column chromatography, eluted with PE/EtOAc (20:1), to afford the title compound (2.25 g, 83.7%).

Step 5:
2,2,3,3,6-pentafluoro-2,3-dihydro-1H-inden-1-ol

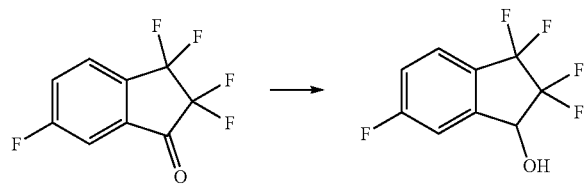 [SMILES: O=C1c2cc(F)ccc2C(F)(F)C1(F)F ; OC1c2cc(F)ccc2C(F)(F)C1(F)F]

To a stirred solution of 2,2,3,3,6-pentafluoro-2,3-dihydro-1H-inden-1-one (300 mg, 1.35 mmol, 1.0 equiv.) and triethylamine (273.35 mg, 2.70 mmol, 2.0 equiv.) in DCM (3 mL) was added formic acid (186.49 mg, 4.05 mmol, 3.0 equiv.) dropwise at 0° C., followed by the addition of RuCl(P-cymene)[(S,S)-Ts-DPEN] (8.59 mg, 0.014 mmol, 0.01 equiv). The resulting mixture was stirred for 3 h at room temperature under nitrogen atmosphere then washed with water. The organic layer was dried over anhydrous Na$_2$SO$_4$ and concentrated under reduced pressure. The residue was purified by silica gel column chromatography, eluted with PE/EtOAc (5:1), to afford the title compound (300 mg, 99.1%).

Step 6: 7-bromo-2,2,3,3,6-pentafluoro-2,3-dihydro-1H-inden-1-ol

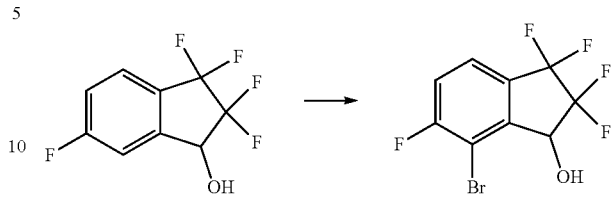

To a stirred solution of 2,2,3,3,6-pentafluoro-2,3-dihydro-1H-inden-1-ol (2500 mg, 11.154 mmol, 1.00 equiv.) in tetrahydrofuran (60 mL) was added LDA (2.0 M, 16.73 mL, 33.463 mmol, 3.00 equiv.) dropwise at −78° C. under nitrogen atmosphere. The resulting mixture was warmed to −30° C. over 30 min and stirred for additional 30 min at −30° C. To the above mixture was added a solution of carbon tetrabromide (3699.05 mg, 11.154 mmol, 1.00 equiv.) in THF dropwise at −78° C. The resulting mixture was allowed warm to −30° C. over 30 min and stirred for additional 30 min at −30° C. The reaction was quenched with saturated NH$_4$Cl (aq.) at −30° C. The resulting mixture was extracted with EtOAc and the organic layer was washed with brine, dried over anhydrous Na$_2$SO$_4$. After filtration, the filtrate was concentrated under reduced pressure. The residue was purified by silica gel column chromatography, eluted with PE/EtOAc (10:1), to afford the title compound (2600 mg, 76.9%) as a light yellow oil. MS (ES, m/z): [M−H]$^-$=300.9, 302.9.

Step 7: 7-bromo-2,2,3,3,6-pentafluoro-2,3-dihydro-1H-inden-1-one

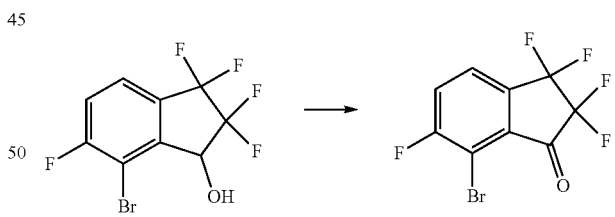

To a stirred mixture of 7-bromo-2,2,3,3,6-pentafluoro-2,3-dihydro-1H-inden-1-ol (2.63 g, 8.679 mmol, 1.00 equiv.) in CH$_3$CN (45 mL) was added IBX (4.86 g, 17.356 mmol, 2.00 equiv) at room temperature. The resulting mixture was stirred for 3 h at 80° C., then cooled and filtered. The filter cake was washed with EtOAc. The combined filtrate was concentrated under reduced pressure. The residue was purified by silica gel column chromatography, eluted with PE/EtOAc (10:1), to afford the title compound (1.8 g, 68.9%) as an off-white solid.

Step 8: 1-allyl-7-bromo-2,2,3,3,6-pentafluoro-2,3-dihydro-1H-inden-1-ol

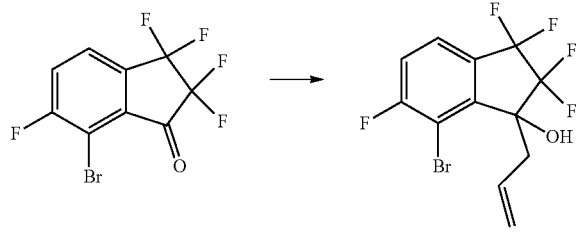 [SMILES: O=C1c2c(ccc(F)c2Br)C(F)(F)C1(F)F ; C=CCC1(O)c2c(ccc(F)c2Br)C(F)(F)C1(F)F]

To a stirred solution of 7-bromo-2,2,3,3,6-pentafluoro-2,3-dihydro-1H-inden-1-one (100 mg, 0.332 mmol, 1.00 equiv.) in THF (3 mL) was added allylmagnesium bromide (1.0 M, 0.50 mL, 0.50 mmol, 1.50 equiv.) dropwise at −78° C. under nitrogen atmosphere. The resulting mixture was stirred for 1 h at −78° C. under nitrogen atmosphere. The reaction was quenched with saturated NH$_4$Cl (aq.). The resulting mixture was extracted with EtOAc and the organic layer was dried over anhydrous Na$_2$SO$_4$. After filtration, the filtrate was concentrated under reduced pressure. The residue was purified by silica gel column chromatography, eluted with PE/EtOAc (5:1), to afford the title compound (90 mg, 79.0%) as a yellow oil. MS (ES, m/z): [M−H]$^-$=340.9, 342.9.

Step 9: 3,3,4,4,7-pentafluoro-1-methylene-1,2,3,4-tetrahydro-2aH-cyclopenta[cd]inden-2a-ol

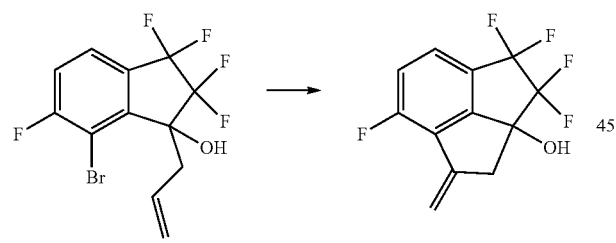

To a stirred mixture of 1-allyl-7-bromo-2,2,3,3,6-pentafluoro-2,3-dihydro-1H-inden-1-ol (1050 mg, 3.060 mmol, 1.00 equiv.) in DMF (25 mL) were added AcONa (753.17 mg, 9.181 mmol, 3.00 equiv.) and Pd(dppf)Cl$_2$.CH$_2$Cl$_2$ (249.93 mg, 0.306 mmol, 0.10 equiv.) at room temperature. The resulting mixture was stirred for 3 h at 100° C. under nitrogen atmosphere. The resulting mixture was diluted with water and extracted with EtOAc. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (5:1), to afford the title compound (370 mg, 46.1%) as a light yellow oil.

Step 10: 3-fluoro-5-((3,3,4,4-tetrafluoro-2a-hydroxy-1-methylene-2,2a,3,4-tetrahydro-1H-cyclopenta[cd]inden-7-yl)oxy)benzonitrile

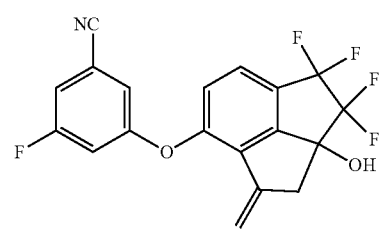

To a stirred mixture of 3,3,4,4,7-pentafluoro-1-methylene-1,2,3,4-tetrahydro-2aH-cyclopenta[cd]inden-2a-ol (40 mg, 0.15 mmol, 1.00 equiv.) and 3-fluoro-5-hydroxybenzonitrile (20.92 mg, 0.153 mmol, 1.00 equiv.) in DMF (1 mL) was added Cs$_2$CO$_3$ (49.71 mg, 0.15 mmol, 1.00 equiv.) at room temperature. The resulting mixture was stirred for 24 h at 100° C. The resulting mixture was filtered and the filtrate was purified by Prep-HPLC to afford (16.77 mg, 29.0%). MS (ES, m/z): [M−H]$^-$=378.1.

Example 2

Synthesis of 3-fluoro-5-((3,3,4,4-tetrafluoro-2a-hydroxy-1-oxo-2,2a,3,4-tetrahydro-1H-cyclopenta[cd]inden-7-yl)oxy)benzonitrile

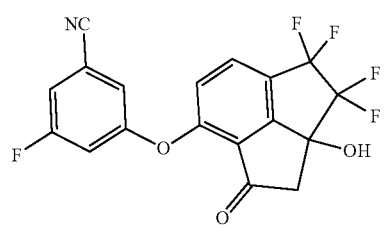 [SMILES: N#Cc1cc(F)cc(Oc2ccc3c4c2C(=O)CC4(O)C(F)(F)C3(F)F)c1]

Step 1: 3,3,4,4,7-pentafluoro-2a-hydroxy-2,2a,3,4-tetrahydro-1H-cyclopenta[cd]inden-1-one

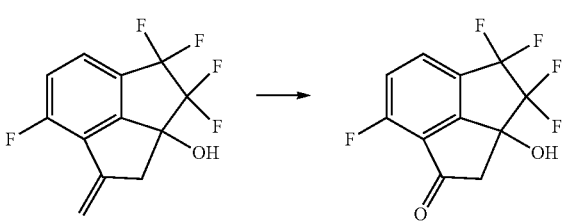 [SMILES: C=C1CC2(O)c3c(ccc(F)c31)C(F)(F)C2(F)F ; O=C1CC2(O)c3c(ccc(F)c31)C(F)(F)C2(F)F]

To a stirred mixture of 3,3,4,4,7-pentafluoro-1-methylene-1,2,3,4-tetrahydro-2aH-cyclopenta[cd]inden-2a-ol (320 mg, 1.22 mmol, 1.00 equiv.) in a mixed solvent (DCM/CH$_3$CN/H$_2$O=3 mL/3 mL/4.50 mL) were added NaIO$_4$ (1044.25 mg, 4.882 mmol, 4.00 equiv.) and RuCl$_3$.H$_2$O (13.76 mg, 0.061 mmol, 0.05 equiv.) at room temperature. The resulting mixture was stirred for 6 h at room temperature. The resulting mixture was diluted with water and extracted with DCM. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (3:1), to afford the title compound (250 mg, 77.5%) as a white solid. MS (ES, m/z): [M−H]$^-$=263.0.

Step 2: 3-fluoro-5-((3,3,4,4-tetrafluoro-2a-hydroxy-1-oxo-2,2a,3,4-tetrahydro-1H-cyclopenta[cd]inden-7-yl)oxy)benzonitrile

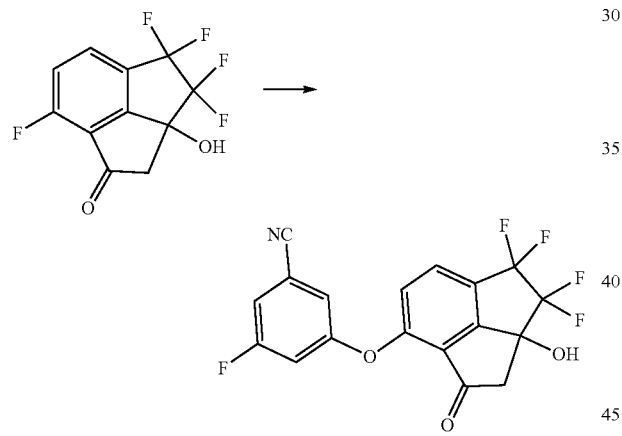

To a stirred mixture of 3,3,4,4,7-pentafluoro-2a-hydroxy-2,2a,3,4-tetrahydro-1H-cyclopenta[cd]inden-1-one (200 mg, 0.757 mmol, 1.00 equiv.) and 3-fluoro-5-hydroxybenzonitrile (103.81 mg, 0.757 mmol, 1.0 equiv.) in DMF (3 mL) was added Cs$_2$CO$_3$ (246.69 mg, 0.76 mmol, 1.0 equiv.) at room temperature. The resulting mixture was stirred for 16 h at room temperature. The resulting mixture was diluted with water and extracted with EtOAc. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (3:1), to afford the title compound (200 mg, 69.3%) as a white semi-solid. MS (ES, m/z): [M−H]$^-$=380.0.

Example 3

Synthesis of 3-fluoro-5-((3,3,4,4-tetrafluoro-1,2a-dihydroxy-2,2a,3,4-tetrahydro-1H-cyclopenta[cd]inden-7-yl)oxy)benzonitrile

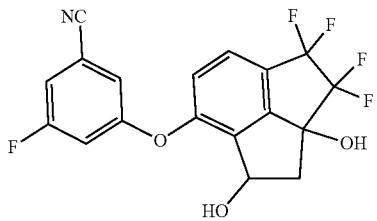 [SMILES: N#Cc1cc(F)cc(Oc2ccc3c4c2C(O)CC4(O)C(F)(F)C3(F)F)c1]

To a solution of 3-fluoro-5-((3,3,4,4-tetrafluoro-2a-hydroxy-1-oxo-2,2a,3,4-tetrahydro-1H-cyclopenta[cd]inden-7-yl)oxy)benzonitrile (40 mg, 0.105 mmol, 1.00 equiv.) in MeOH (1 mL) was added NaBH$_4$ (7.94 mg, 0.210 mmol, 2.0 equiv.) at room temperature. The resulting mixture was stirred for 3 h at room temperature. The reaction was quenched with aq. HCl (2.0 M) at room temperature to pH=7. The resulting mixture was concentrated under vacuum. The residue was diluted with water and extracted with EtOAc. The combined organic layers were washed with water, dried over anhydrous Na$_2$SO$_4$. After filtration, the filtrate was concentrated under reduced pressure. The residue was purified by prep-TLC, eluted with PE/EtOAc (3:1), to afford the title compound (40 mg, 99.5%) as a colorless oil. MS (ES, m/z): [M−H]$^-$=382.0.

Example 4

Synthesis of 3-fluoro-5-((1,3,3,4,4-pentafluoro-2a-hydroxy-2,2a,3,4-tetrahydro-1H-cyclopenta[cd]inden-7-yl)oxy)benzonitrile [4]

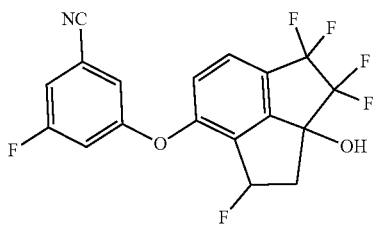 [SMILES: N#Cc1cc(F)cc(Oc2ccc3c4c2C(F)CC4(O)C(F)(F)C3(F)F)c1]

To a stirred solution of 3-fluoro-5-((3,3,4,4-tetrafluoro-1,2a-dihydroxy-2,2a,3,4-tetrahydro-1H-cyclopenta[cd]inden-7-yl)oxy)benzonitrile (20 mg, 0.05 mmol, 1.00 equiv.) in DCM (0.5 mL) was added DAST (6.73 mg, 0.04 mmol, 0.80 equiv.) dropwise at −50° C. The resulting mixture was stirred for 30 min at −50° C.−−40° C. The reaction mixture was quenched with NaHCO$_3$ (aq.) and extracted with DCM. The organic layer was dried over anhydrous Na$_2$SO$_4$. After filtration, the filtrate was concentrated under reduced pressure. The residue was purified by Prep-HPLC to afford the title compound (4.3 mg, 21.3%) as a white solid. MS (ES, m/z): [M−H]$^-$=384.1.

Example 5

Synthesis of 1,3,3,4,4-pentafluoro-7-((5-fluoropyridin-3-yl)oxy)-1,2,3,4-tetrahydro-2aH-cyclopenta[cd]inden-2a-ol

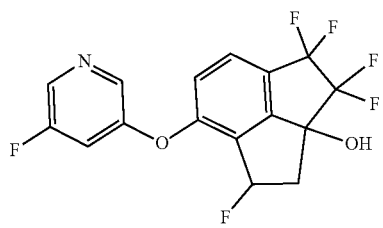 [SMILES: OC12CC(F)c3c(Oc4cncc(F)c4)ccc(c31)C(F)(F)C2(F)F]

Step 1: 3,3,4,4-tetrafluoro-7-((5-fluoropyridin-3-yl)oxy)-2a-hydroxy-2,2a,3,4-tetrahydro-1H-cyclopenta[cd]inden-1-one

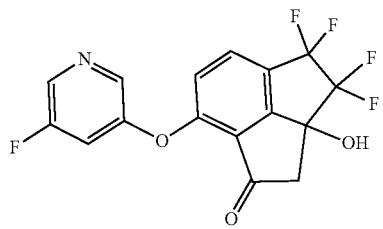 [SMILES: O=C1CC2(O)c3c(ccc(Oc4cncc(F)c4)c31)C(F)(F)C2(F)F]

To a stirred mixture of 3,3,4,4,7-pentafluoro-2a-hydroxy-2,2a,3,4-tetrahydro-1H-cyclopenta[cd]inden-1-one (95 mg, 0.36 mmol, 1.00 equiv.) and 5-fluoropyridin-3-ol (41 mg, 0.36 mmol, 1.00 equiv.) in DMF (2.00 mL) was added $Cs_2CO_3$ (128.90 mg, 0.40 mmol, 1.10 equiv.) at room temperature under nitrogen atmosphere. After stirring for 4 h at room temperature, the reaction mixture was quenched with water at 0° C. The resulting mixture was extracted with EtOAc. The combined organic layers were washed with brine and dried over anhydrous $Na_2SO_4$. After filtration, the filtrate was concentrated under reduced pressure. The residue was purified by Prep-TLC (PE/EtOAc=3/1) to afford the title compound (85 mg, 66%) as a white solid. MS (ES, m/z): $[M+1]^+=358.1$.

Step 2: 3,3,4,4-tetrafluoro-7-((5-fluoropyridin-3-yl)oxy)-1,2,3,4-tetrahydro-2aH-cyclopenta-[cd]indene-1,2a-diol

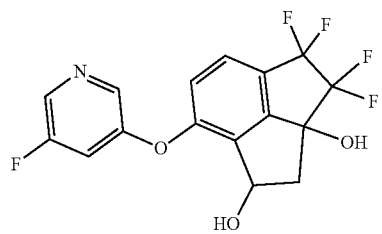 [SMILES: OC1CC2(O)c3c(ccc(Oc4cncc(F)c4)c31)C(F)(F)C2(F)F]

To a stirred solution of 3,3,4,4-tetrafluoro-7-((5-fluoropyridin-3-yl)oxy)-2a-hydroxy-2,2a,3,4-tetrahydro-1H-cyclopenta[cd]inden-1-one (85 mg, 0.24 mmol, 1.00 equiv.) in MeOH (1.50 mL) was added $NaBH_4$ (18 mg, 0.48 mmol, 2.00 equiv.) at room temperature. After stirring for 1 h at room temperature, the reaction mixture was quenched with saturated $NH_4Cl$ (aq.) at 0° C. The resulting mixture was extracted with EtOAc and the combined organic layers were washed with brine and dried over anhydrous $Na_2SO_4$. After filtration, the filtrate was concentrated under reduced pressure. The residue was purified by silica gel column chromatography, eluted with EtOAc/PE (0-60%), to afford the title compound (80 mg, 93.7%) as a light yellow solid. MS (ES, m/z): $[M+1]^+=360.1$.

Step 3: 1,3,3,4,4-pentafluoro-7-((5-fluoropyridin-3-yl)oxy)-1,2,3,4-tetrahydro-2aH-cyclopenta[cd]inden-2a-ol

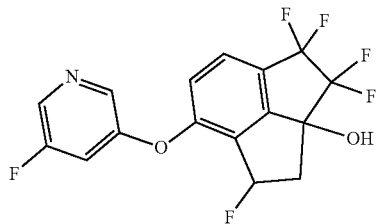 [SMILES: OC12CC(F)c3c(Oc4cncc(F)c4)ccc(c31)C(F)(F)C2(F)F]

To a stirred solution of 3,3,4,4-tetrafluoro-7-((5-fluoropyridin-3-yl)oxy)-1,2,3,4-tetrahydro-2aH-cyclopenta[cd]indene-1,2a-diol (30 mg, 0.08 mmol, 1.00 equiv.) in THF (1.00 mL) was added DAST (20 mg, 0.12 mmol, 1.50 equiv.) at −50° C. under nitrogen atmosphere. After stirring for 2 h at −50-−30° C., the reaction mixture was quenched with saturated $NaHCO_3$ (aq.) at 0° C. The resulting mixture was extracted with EtOAc and the combined organic layers were washed with brine and dried over anhydrous $Na_2SO_4$. After filtration, the filtrate was concentrated under reduced pressure. The crude product was purified by Prep-HPLC to afford the title compound (3 mg, 10%) as a white solid. MS (ES, m/z): $[M+1]^+=362.1$.

Example 6

Synthesis of 3-fluoro-5-((3,3,4,4-tetrafluoro-2a-hydroxy-2,2a,3,4-tetrahydrospiro-[cyclopenta[cd]indene-1,1'-cyclopropan]-7-yl)oxy)benzonitrile

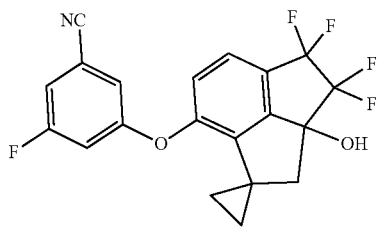 [SMILES: N#Cc1cc(F)cc(Oc2ccc3c4c2C2(CC2)CC4(O)C(F)(F)C3(F)F)c1]

To a stirred mixture of diethylzinc (0.53 mL, 0.53 mmol, 1.0 M in hexane) in DCM (3 mL) was added TFA (60 mg, 0.526 mmol, 4.00 equiv.) dropwise at 0° C. under nitrogen atmosphere. The resulting mixture was stirred for 10 min at 0° C. To the above mixture was added $CH_2I_2$ (141 mg, 0.53 mmol, 4.0 equiv.) dropwise at 0° C. The resulting mixture was stirred for additional 10 min at 0° C., followed by the addition of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile (50 mg, 0.132 mmol, 1.00 equiv.). The reaction mixture was stirred for 10 min at 0° C., then stirred for additional 1 h at room temperature. The reaction mixture was quenched with water and extracted with CH$_2$Cl$_2$. The combined organic layers were dried over anhydrous Na$_2$SO$_4$. After filtration, the filtrate was concentrated under reduced pressure and the crude product was purified by Prep-HPLC to afford the title compound (5.6 mg, 10.8%) as a white solid. MS (ES, m/z): [M−H]$^−$=392.1.

Example 7

Synthesis of 3-fluoro-5-((3,3,4,4-tetrafluoro-2a-hydroxy-1-methyl-2,2a,3,4-tetrahydro-1H-cyclopenta[cd]inden-7-yl)oxy)benzonitrile

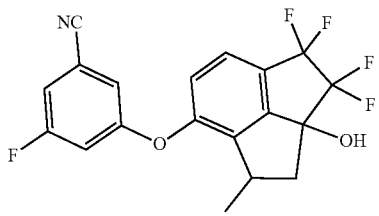 [SMILES: CC1CC2(O)c3c(ccc(Oc4cc(F)cc(C#N)c4)c31)C(F)(F)C2(F)F]

To a stirred mixture of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile (30 mg, 0.08 mmol, 1.00 equiv.) and phenyl sulfide (1.47 mg, 0.008 mmol, 0.10 equiv.) in ethyl acetate (3 mL) and CH$_3$OH (3 mL) was added 10% Pd/C (20 mg) at room temperature. The resulting mixture was stirred for 48 h at room temperature under hydrogen atmosphere then filtered. The filtrate was concentrated under reduced pressure and the crude product was purified by Prep-HPLC to afford the title compound (9 mg, 30%) as a white solid. MS (ES, m/z): [M−H]$^−$=380.1.

Example 8

Synthesis of 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile

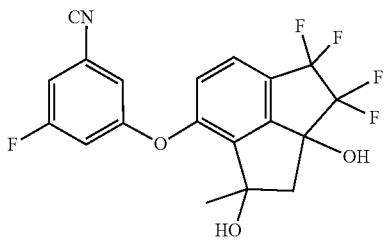

To a stirred solution of 3-fluoro-5-((3,3,4,4-tetrafluoro-2a-hydroxy-1-oxo-2,2a,3,4-tetrahydro-1H-cyclo-penta[cd]inden-7-yl)oxy)benzonitrile (20 mg, 0.05 mmol, 1.00 equiv.) in THF (0.60 mL) was added bromo(methyl)magnesium (1.0 M, 0.16 mL, 0.16 mmol, 3.05 equiv.) dropwise at −78° C. under nitrogen atmosphere. The resulting mixture was stirred for 1 h at −78° C. under nitrogen atmosphere, then quenched with saturated NH$_4$Cl (aq.) (2 mL) at −78° C. The resulting mixture was extracted with EtOAc. The combined organic layers were washed with brine, dried over anhydrous Na$_2$SO$_4$. After filtration, the filtrate was concentrated under reduced pressure. The residue was purified by Prep-HPLC to afford the title compound (10 mg, 48.0%) as a white solid. MS (ES, m/z): [M−H]$^−$=396.2.

Example 9

Synthesis of 3-fluoro-5-((1,3,3,4,4-pentafluoro-2a-hydroxy-1-methyl-2,2a,3,4-tetrahydro-1H-cyclopenta[cd]inden-7-yl)oxy)benzonitrile

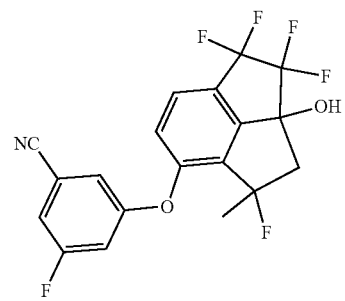 [SMILES: CC1(F)CC2(O)c3c(ccc(Oc4cc(F)cc(C#N)c4)c31)C(F)(F)C2(F)F]

To a stirred mixture of 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile (30 mg, 0.07 mmol, 1.00 equiv.) in DCM (1.5 mL) was added DAST (12 mg, 0.07 mmol, 1.00 equiv.) dropwise at −50° C. under nitrogen atmosphere. The resulting mixture was stirred for 1.5 h at −50–−40° C. under nitrogen atmosphere then quenched with saturated NaHCO$_3$ (aq.) at 0° C. The resulting mixture was extracted with DCM and the combined organic layers were washed with water and dried over anhydrous Na$_2$SO$_4$. After filtration, the filtrate was concentrated under reduced pressure and the crude was purified by Prep-HPLC to afford the title compound (4.3 mg, 14.3%) as a white solid. MS (ES, m/z): [M−H]$^−$=398.1.

Example 10

Synthesis of 3-fluoro-5-((3,3,4,4-tetrafluoro-2a-hydroxy-2,2a,3,4-tetrahydro-1H-cyclopenta[ed]inden-7-yl)oxy)benzonitrile

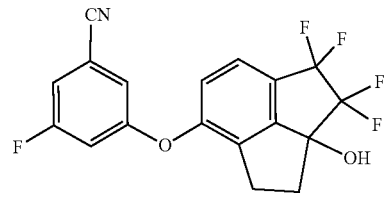 [SMILES: N#Cc1cc(F)cc(Oc2ccc3c4c2CCC4(O)C(F)(F)C3(F)F)c1]

Step 1: O-(7-(3-cyano-5-fluorophenoxy)-3,3,4,4-tetrafluoro-2a-hydroxy-2,2a,3,4-tetrahydro-1H-cyclopenta[cd]inden-1-yl) 1H-imidazole-1-carbothioate

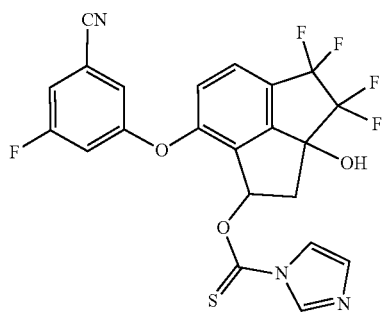 [SMILES: N#Cc1cc(F)cc(Oc2ccc3c4c2C(OC(=S)n2ccnc2)CC4(O)C(F)(F)C3(F)F)c1]

To a stirred solution of 3-fluoro-5-((3,3,4,4-tetrafluoro-1,2a-dihydroxy-2,2a,3,4-tetrahydro-1H-cyclopenta[cd]inden-7-yl)oxy)benzonitrile (100 mg, 0.26 mmol, 1.00 equiv.) and DMAP (6 mg, 0.05 mmol, 0.20 equiv.) in DCE (2.0 mL) was added di(1H-imidazol-1-yl)methanethione (56 mg, 0.31 mmol, 1.20 equiv.) at room temperature under nitrogen atmosphere. The resulting mixture was stirred for 3 h at room temperature. The reaction mixture was concentrated and the residue was purified by Prep-TLC (PE/EtOAc 2:1) to afford the title compound (80 mg, 62%). MS (ES, m/z): [M+H]$^+$=494.1.

Step 2: 3-fluoro-5-((3,3,4,4-tetrafluoro-2a-hydroxy-2,2a,3,4-tetrahydro-1H-cyclopenta[cd]inden-7-yl)oxy)benzonitrile

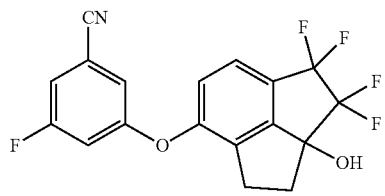 [SMILES: N#Cc1cc(F)cc(Oc2ccc3c4c2CCC4(O)C(F)(F)C3(F)F)c1]

To a stirred solution of O-(7-(3-cyano-5-fluorophenoxy)-3,3,4,4-tetrafluoro-2a-hydroxy-2,2a,3,4-tetrahydro-1H-cyclopenta[cd]inden-1-yl) 1H-imidazole-1-carbothioate (65 mg, 0.13 mmol, 1.00 equiv.) and Bu$_3$SnH (115 mg, 0.40 mmol, 3.00 equiv.) in toluene (2.0 mL) was added AIBN (65 mg, 0.40 mmol, 3.00 equiv.) at room temperature under nitrogen atmosphere. The resulting mixture was stirred for 16 h at 50° C., cooled and diluted with water, and extracted with EtOAc. The combined organic layers were washed with water and brine, dried over anhydrous Na$_2$SO$_4$ and concentrated. The residue was purified by Prep-TLC (PE/EtOAc=2/1) and Perp-HPLC to afford the title compound (12 mg, 25%) as a white solid. MS (ES, m/z): [M–H]$^-$=366.2.

Example 11

Synthesis of 3-((2a-amino-1,3,3,4,4-pentafluoro-2,2a,3,4-tetrahydro-1H-cyclopenta[cd]inden-7-yl)oxy)-5-fluorobenzonitrile

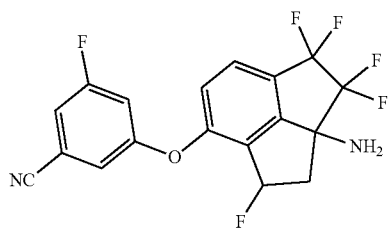 [SMILES: N#Cc1cc(F)cc(Oc2ccc3c4c2C(F)CC4(N)C(F)(F)C3(F)F)c1]

Step 1: N-(7-bromo-2,2,3,3,6-pentafluoro-2,3-dihydro-1H-inden-1-ylidene)-2-methylpropane-2-sulfinamide

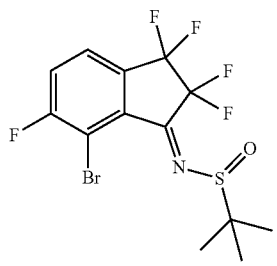 [SMILES: CC(C)(C)S(=O)/N=C1/c2c(ccc(F)c2Br)C(F)(F)C1(F)F]

To a stirred mixture of 7-bromo-2,2,3,3,6-pentafluoro-2,3-dihydro-1H-inden-1-one (1.00 g, 3.32 mmol, 1.00 equiv.) and 2-methylpropane-2-sulfinamide (0.81 g, 6.64 mmol, 2.00 equiv.) in THF (20.0 mL) was added Ti(OEt)$_4$ (3.03 g, 13.29 mmol, 4.00 equiv.) at room temperature. After stirring for 4 h at 75° C., the reaction mixture was cooled and concentrated under reduced pressure. The residue was purified by silica gel column chromatography, eluted with EtOAc/PE (0-60%), to afford the title compound (900 mg, 67.0%) as a brown oil. MS (ES, m/z): [M+1]$^+$=404.0.

Step 2: N-(1-allyl-7-bromo-2,2,3,3,6-pentafluoro-2,3-dihydro-1H-inden-1-yl)-2-methylpropane-2-sulfinamide

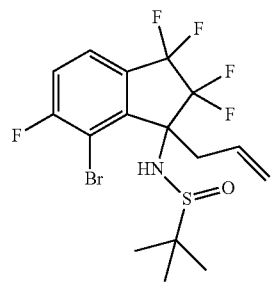 [SMILES: C=CCC1(NS(=O)C(C)(C)C)c2c(ccc(F)c2Br)C(F)(F)C1(F)F]

To a stirred solution of N-(7-bromo-2,2,3,3,6-pentafluoro-2,3-dihydro-1H-inden-1-ylidene)-2-methylpropane-2-sulfinamide (900 mg, 2.23 mmol, 1.00 equiv.) in THF (15.0 mL) was added allylmagnesium bromide (2.0 M, 1.34 mL, 2.70 mmol, 1.20 equiv.) at 0° C. After stirring for 1.5 h at 0° C., the reaction mixture was quenched with saturated NH$_4$Cl (aq.) at 0° C. then extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-50%), to afford the title compound (750 mg, 75.5%) as a light yellow oil. MS (ES, m/z): [M+1]$^+$=446.1.

Step 3: 2-methyl-N-(3,3,4,4,7-pentafluoro-1-methylene-1,2,3,4-tetrahydro-2aH-cyclopenta[cd]-inden-2a-yl)propane-2-sulfinamide

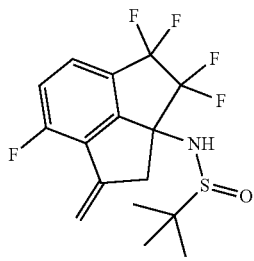 [SMILES: C=C1CC2(NS(=O)C(C)(C)C)c3c(ccc(F)c31)C(F)(F)C2(F)F]

To a stirred mixture of N-(1-allyl-7-bromo-2,2,3,3,6-pentafluoro-2,3-dihydro-1H-inden-1-yl)-2-methylpropane-2-sulfinamide (750 mg, 1.68 mmol, 1.00 equiv.) and Pd(dppf)Cl$_2$.CH$_2$Cl$_2$ (137 mg, 0.17 mmol, 0.10 equiv.) in DMF (15.0 mL) was added NaOAc (414 mg, 5.05 mmol, 3.00 equiv.) at room temperature under nitrogen atmosphere. After stirring for 1.5 h at 100° C., the reaction mixture was cooled to room temperature, quenched with water and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (10%-40%), to afford the title compound (450 mg, 73.3%) as a light yellow solid. MS (ES, m/z): [M+1]$^+$=366.1.

Step 4: 3,3,4,4,7-pentafluoro-1-methylene-1,2,3,4-tetrahydro-2aH-cyclopenta[cd]inden-2a-amine

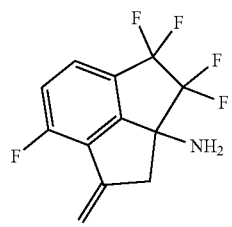

To a stirred solution of 2-methyl-N-(3,3,4,4,7-pentafluoro-1-methylene-1,2,3,4-tetrahydro-2aH-cyclopenta[cd]inden-2a-yl)propane-2-sulfinamide (150 mg, 0.41 mmol, 1.00 equiv.) in 1,4-dioxane (1.0 mL) was added a solution of HCl in 1,4-dioxane (4.0 M, 1.00 mL, 4.0 mmol, 9.74 equiv.) at room temperature. After stirring for 5 h at room temperature, the reaction mixture was quenched with NaHCO$_3$ (aq.) at room temperature and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-60%), to afford the title compound (85 mg, 79.3%) as a light yellow oil. MS (ES, m/z): [M+1]$^+$=262.1.

Step 5: 2a-amino-3,3,4,4,7-pentafluoro-2,2a,3,4-tetrahydro-1H-cyclopenta[cd]inden-1-one

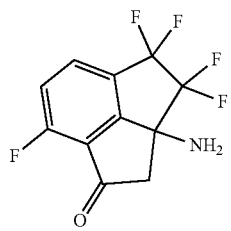 [SMILES: NC12CC(=O)c3c(F)ccc(c31)C(F)(F)C2(F)F]

To a stirred mixture of 3,3,4,4,7-pentafluoro-1-methylene-1,2,3,4-tetrahydro-2aH-cyclopenta[cd]inden-2a-amine (85 mg, 0.325 mmol, 1.00 equiv.) and NaIO$_4$ (278 mg, 1.30 mmol, 4.00 equiv.) in CH$_3$CN (0.50 mL) and DCM (0.50 mL) were added water (0.75 mL) and RuCl$_3$.H$_2$O (7.34 mg, 0.03 mmol, 0.10 equiv.) at room temperature. After stirring for 1 h at room temperature, the resulting mixture was diluted with DCM. The organic layer was washed with brine and dried over anhydrous Na$_2$SO$_4$. After filtration, the filtrate was concentrated under reduced pressure and the residue was purified by Prep-TLC (PE/EtOAc=3/1) to afford the title compound (45 mg, 52.5%) as a light yellow oil. MS (ES, m/z): [M−1]$^-$=261.9.

Step 6: 3-((2a-amino-3,3,4,4-tetrafluoro-1-oxo-2,2a,3,4-tetrahydro-1H-cyclopenta[cd]inden-7-yl)oxy)-5-fluorobenzonitrile

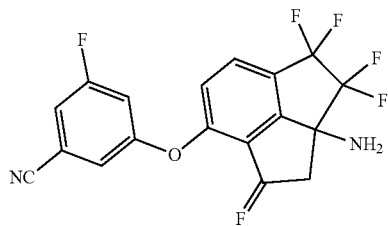

To a stirred mixture of 2a-amino-3,3,4,4,7-pentafluoro-2,2a,3,4-tetrahydro-1H-cyclopenta[cd]inden-1-one (40 mg, 0.15 mmol, 1.00 equiv.) and 3-fluoro-5-hydroxybenzonitrile (21 mg, 0.15 mmol, 1.00 equiv.) in DMF (1.00 mL) was added Cs$_2$CO$_3$ (50 mg, 0.15 mmol, 1.00 equiv.) at room temperature. After stirring for 1.5 h at room temperature, the reaction was quenched with water and extracted with EtOAc. The combined organic layers were washed with brine and dried over anhydrous Na$_2$SO$_4$. After filtration, the filtrate was concentrated under reduced pressure. The residue was purified by Prep-TLC (PE/EtOAc=3/1) to afford the title compound (35 mg, 60.3%) as a white solid. MS (ES, m/z): [M+1]$^+$=381.1.

Step 7: 3-((2a-amino-3,3,4,4-tetrafluoro-1-hydroxy-2,2a,3,4-tetrahydro-1H-cyclopenta[cd]inden-7-yl)oxy)-5-fluorobenzonitrile

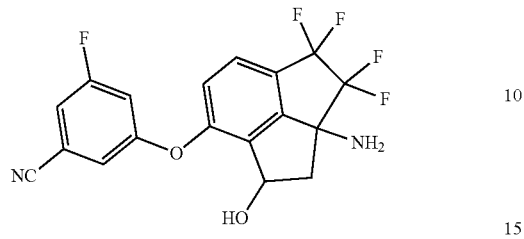

To a stirred solution of 3-((2a-amino-3,3,4,4-tetrafluoro-1-oxo-2,2a,3,4-tetrahydro-1H-cyclopenta[cd]inden-7-yl)oxy)-5-fluorobenzonitrile (35 mg, 0.09 mmol, 1.00 equiv.) in MeOH (0.50 mL) was added NaBH$_4$ (5 mg, 0.13 mmol, 1.4 equiv.) at room temperature. After stirring for 0.5 h at room temperature, the reaction mixture was quenched with saturated NH$_4$Cl (aq.) at 0° C. and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-60%), to afford the title compound (30 mg, 85.3%) as a light yellow oil. MS (ES, m/z): [M+1]$^+$=383.1.

Step 8: 3-((2a-amino-1,3,3,4,4-pentafluoro-2,2a,3,4-tetrahydro-1H-cyclopenta[cd]inden-7-yl)oxy)-5-fluorobenzonitrile

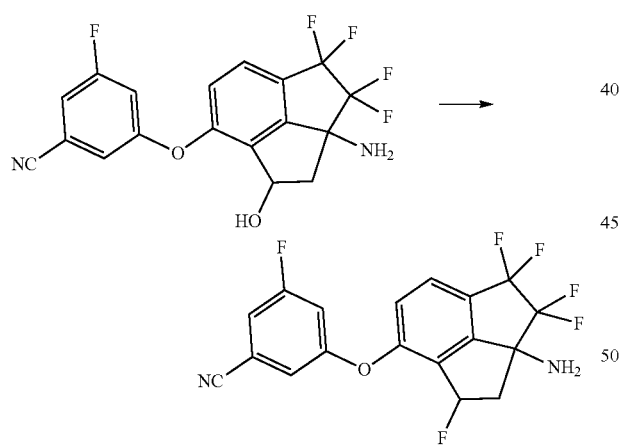

To a stirred solution of 3-((2a-amino-3,3,4,4-tetrafluoro-1-hydroxy-2,2a,3,4-tetrahydro-1H-cyclopenta[cd]inden-7-yl)oxy)-5-fluorobenzonitrile (25 mg, 0.07 mmol, 1.00 equiv.) in DCM (1.0 mL) was added DAST (16 mg, 0.10 mmol, 1.5 equiv.) at room temperature. After stirring for 2 h at room temperature, the reaction mixture was quenched with saturated NaHCO$_3$ (aq.) at 0° C. and extracted with DCM. The combined organic layers were washed with brine and dried over anhydrous Na$_2$SO$_4$. After filtration, the filtrate was concentrated and purified by Prep-HPLC to afford the title compound (6 mg, 24%) as a white solid. MS (ES, m/z): [M+1]$^+$=385.1.

Example 12

Synthesis of 3-fluoro-5-((1,1,2a,3,3,4,4-heptafluoro-2,2a,3,4-tetrahydro-1H-cyclopenta[cd]inden-7-yl)oxy)benzonitrile

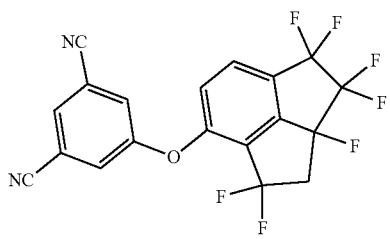 [SMILES: N#Cc1cc(C#N)cc(Oc2ccc3c4c2C(F)(F)CC4(F)C(F)(F)C3(F)F)c1]

To a stirred mixture of 3-fluoro-5-((3,3,4,4-tetrafluoro-2a-hydroxy-1-oxo-2,2a,3,4-tetrahydro-1H-cyclo-penta[cd]inden-7-yl)oxy)benzonitrile (30 mg, 0.08 mmol, 1.00 equiv.) in DCM (1.0 mL) were added 4-tert-butyl-2,6-dimethylphenylsulfur trifluoride (59 mg, 0.24 mmol, 3.00 equiv.) and pyridine hydrofluoride (0.05 mL, 65%-70%) at room temperature. The resulting mixture was stirred for 24 h at room temperature under nitrogen atmosphere then diluted with water and extracted with DCM. The combined organic layers were washed with water and dried over anhydrous Na$_2$SO$_4$. After filtration, the filtrate was concentrated and purified by Prep-HPLC to afford the title compound (9.9 mg, 31.1%) as a white solid. MS (ES, m/z): [M−H]$^-$=404.1.

Example 13

Synthesis of 3-((3,3-difluoro-2a-hydroxy-1-methylene-2,2a,3,4-tetrahydro-1H-cyclopenta[cd]inden-5-yl)oxy)-5-fluorobenzonitrile

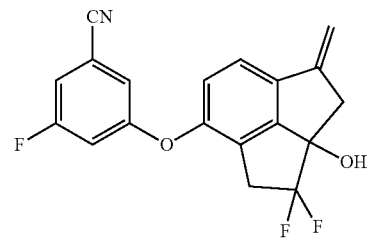 [SMILES: C=C1CC2(O)c3c1ccc(Oc1cc(F)cc(C#N)c1)c3CC2(F)F]

Step 1: 3-fluoro-5-((7-iodo-1-oxo-2,3-dihydro-1H-inden-4-yl)oxy)benzonitrile

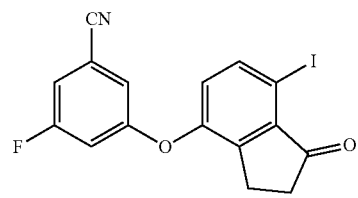 [SMILES: N#Cc1cc(F)cc(Oc2ccc(I)c3c2CCC3=O)c1]

Into a 2 L round-bottom flask were added 3-fluoro-5-((1-oxo-2,3-dihydro-1H-inden-4-yl)oxy)benzonitrile (28 g, 104.77 mmol, 1.00 equiv.), F-TEDA-BF$_4$ (33 g, 93.15 mmol, 0.89 equiv.) and CH$_3$CN (840 mL). To this stirred solution was added a solution of I₂ (24 g, 94.56 mmol, 0.90 equiv.) in CH₃CN (560 mL) dropwise at 60° C. The resulting mixture was stirred for 3 h at 60° C. The mixture was cooled to room temperature then concentrated under vacuum. To the residue was added ethyl acetate (250 mL) and the resulting mixture was stirred for 1 h at 80° C. The mixture was cooled to room temperature and the precipitated solids were collected by filtration and washed with Et₂O to afford the tittle compound (16.8 g, 40.8%) as an off-white solid. MS (ES, m/z): [M+H]⁺=394.0.

Step 2: 3-((2,2-difluoro-7-iodo-1-oxo-2,3-dihydro-1H-inden-4-yl)oxy)-5-fluorobenzonitrile

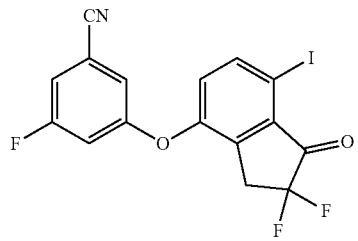 [SMILES: N#Cc1cc(F)cc(Oc2ccc(I)c3c2CC(F)(F)C3=O)c1]

To a stirred mixture of 3-fluoro-5-((7-iodo-1-oxo-2,3-dihydro-1H-inden-4-yl)oxy)-benzonitrile (3.600 g, 9.15 mmol, 1.00 equiv.) and butan-1-amine (6.7 g, 91.57 mmol, 10.00 equiv.) in toluene (90 mL) was added TFA (209 mg, 1.83 mmol, 0.20 equiv.) dropwise at room temperature. The resulting mixture was stirred for 16 h at 100° C. under nitrogen atmosphere then concentrated under vacuum. The residue was dissolved in CH₃CN (90 mL), followed by the addition of Na₂SO₄ (5.2 g, 36.62 mmol, 4.00 equiv.) and F-TEDA-BF₄ (6.5 g, 18.31 mmol, 2.00 equiv.) at room temperature. The resulting mixture was stirred for 2 h at 80° C., diluted with water and extracted with EtOAc. The combined organic layers were washed with water, brine, and dried over anhydrous Na₂SO₄. After filtration, the filtrate was concentrated under reduced pressure. The residue was purified by silica gel column chromatography, eluted with PE/EtOAc (10:1), to afford (1.60 g, 40.7%) of the title compound as a yellow solid.

Step 3: 3-((1-allyl-2,2-difluoro-1-hydroxy-7-iodo-2,3-dihydro-1H-inden-4-yl)oxy)-5-fluorobenzonitrile

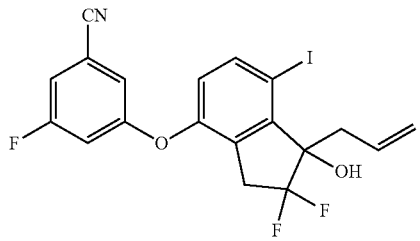 [SMILES: C=CCC1(O)c2c(I)ccc(Oc3cc(F)cc(C#N)c3)c2CC1(F)F]

To a stirred mixture of 3-((2,2-difluoro-7-iodo-1-oxo-2,3-dihydro-1H-inden-4-yl)oxy)-5-fluorobenzonitrile (449 mg, 1.05 mmol, 1.00 equiv.) and allylbromide (253.15 mg, 2.093 mmol, 2.00 equiv.) in THF (10 mL) were added pyridine (165.52 mg, 2.09 mmol, 2.00 equiv.) and (1S,2R)-2-amino-1,2-diphenylethanol (446.30 mg, 2.09 mmol, 2.00 equiv.) at room temperature. Indium powder (240.26 mg, 2.09 mmol, 2.00 equiv.) was then added into the solution and the resulting mixture was stirred for 8 h at room temperature under nitrogen atmosphere. The resulting mixture was filtered and the filter cake was washed with EtOAc. The filtrate was concentrated and purified by silica gel column chromatography, eluted with PE/EtOAc (9:1), to afford the title compound (430 mg, 87.2%) as a yellow oil. MS (ES, m/z): [M−H]⁻=470.0.

Step 4: 3-((3,3-difluoro-2a-hydroxy-1-methylene-2,2a,3,4-tetrahydro-1H-cyclopenta[cd]inden-5-yl)oxy)-5-fluorobenzonitrile

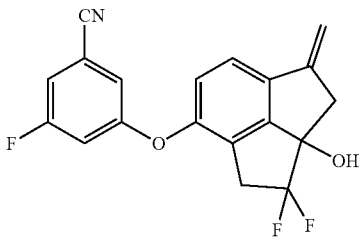 [SMILES: C=C1CC2(O)c3c1ccc(Oc1cc(F)cc(C#N)c1)c3CC2(F)F]

To a stirred solution of 3-((1-allyl-2,2-difluoro-1-hydroxy-7-iodo-2,3-dihydro-1H-inden-4-yl)oxy)-5-fluorobenzonitrile (430 mg, 0.91 mmol, 1.00 equiv.) and NaOAc (225 mg, 2.74 mmol, 3.00 equiv.) in DMF (10 mL) was added Pd(dppf)Cl₂·CH₂Cl₂ (75 mg, 0.09 mmol, 0.10 equiv.) at room temperature under nitrogen atmosphere. The resulting mixture was stirred for 3 h at 100° C. under nitrogen atmosphere then filtered. The filter cake was washed with EtOAc and the filtrate was washed with H₂O, dried over anhydrous Na₂SO₄ and concentrated. The residue was purified by silica gel column chromatography, eluted with PE/EtOAc (5:1), to afford the title compound (223 mg, 71.2%) as a yellow oil.

Example 14

Synthesis of 3-((3,3-difluoro-2a-hydroxy-1-oxo-2,2a,3,4-tetrahydro-1H-cyclopenta[cd]inden-5-yl)oxy)-5-fluorobenzonitrile

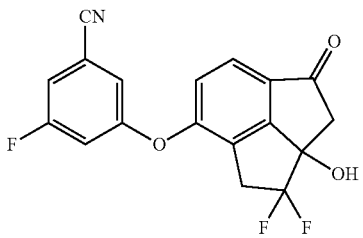 [SMILES: N#Cc1cc(F)cc(Oc2ccc3c4c2CC(F)(F)C4(O)CC3=O)c1]

Into a 25 mL 2-necked round-bottom flask were added 3-((3,3-difluoro-2a-hydroxy-1-methylene-2,2a,3,4-tetrahydro-1H-cyclopenta[cd]inden-5-yl)oxy)-5-fluorobenzonitrile (210 mg, 0.61 mmol, 1.00 equiv.), DCM (2.0 mL), MeCN (2.0 mL) and H₂O (3.0 mL) at room temperature. RuCl₃·H₂O (7 mg, 0.03 mmol, 0.05 equiv.) was then added into the solution. To the above mixture was added NaIO₄ (523 mg, 2.45 mmol, 4.00 equiv.) in portions over 2 min at room temperature and the resulting mixture was stirred for 3 h at room temperature. The resulting mixture was extracted with DCM and the combined organic layers were washed with Na$_2$S$_2$O$_3$ (aq.), H$_2$O and brine, and dried over anhydrous Na$_2$SO$_4$. After filtration, the filtrate was concentrated under reduced pressure. The residue was purified by silica gel column chromatography, eluted with PE/EtOAc (5:1), to afford the title compound (107 mg, 50.7%) as a yellow oil. MS (ES, m/z): =689.1.

Example 15

Synthesis of 3-((3,3-difluoro-1,2a-dihydroxy-2,2a,3,4-tetrahydro-1H-cyclopenta[cd]inden-5-yl)oxy)-5-fluorobenzonitrile

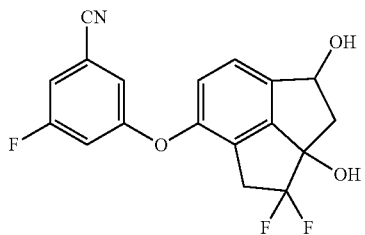

Into an 8 mL sealed tube were added 3-((3,3-difluoro-2a-hydroxy-1-oxo-2,2a,3,4-tetrahydro-1H-cyclopenta[cd]inden-5-yl)oxy)-5-fluorobenzonitrile (100 mg, 0.29 mmol, 1.00 equiv.) and MeOH (2.00 mL) at room temperature. To the above mixture was added NaBH$_4$ (22 mg, 0.58 mmol, 2.0 equiv.) in portions at 0° C. and the resulting mixture was stirred for 1 h at room temperature. The reaction was quenched with water at 0° C. and neutralized to pH=7 with aqueous HCl (1.0 M). The resulting mixture was extracted with DCM and the combined organic layers were dried over anhydrous Na$_2$SO$_4$. After filtration, the filtrate was concentrated and purified by Prep-TLC (PE/EtOAc=5/1) to afford the title compound (78 mg, 77.6%) as a white solid.

Example 16

Synthesis of 3-fluoro-5-((1,3,3-trifluoro-2a-hydroxy-2,2a,3,4-tetrahydro-1H-cyclopenta[cd]inden-5-yl)oxy)benzonitrile

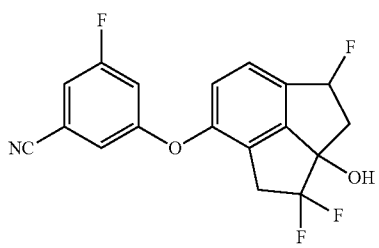 [SMILES: N#Cc1cc(F)cc(Oc2ccc3c4c2CC(F)(F)C4(O)CC3F)c1]

To a stirred solution of 3-((3,3-difluoro-1,2a-dihydroxy-2,2a,3,4-tetrahydro-1H-cyclopenta[cd]inden-5-yl)oxy)-5-fluorobenzonitrile (20 mg, 0.06 mmol, 1.00 equiv.) in THF (0.50 mL) was added a solution of DAST (9.35 mg, 0.06 mmol, 1.00 equiv.) in DCM (0.2 mL) dropwise at −50° C. under nitrogen atmosphere. The resulting mixture was stirred for 1 h at −50° C. under nitrogen atmosphere then quenched with water at −40° C. The mixture was neutralized to pH=7 with saturated NaHCO$_3$ (aq.) then extracted with EtOAc. The combined organic layers were washed with brine and dried over anhydrous Na$_2$SO$_4$. After filtration, the filtrate was concentrated and purified by Prep-HPLC to afford the title compound (5.7 mg, 28.3%) as a white solid. MS (ES, m/z): [2M−H]$^-$=697.2.

Example 17

Synthesis of 3-fluoro-5-((1,1,2,2,3,3,4-heptafluoro-2a-hydroxy-2,2a,3,4-tetrahydro-1H-cyclopenta[cd]inden-5-yl)oxy)benzonitrile

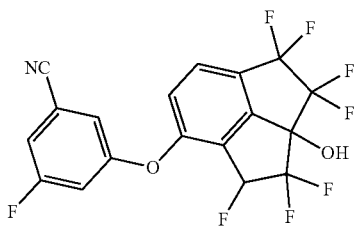 [SMILES: N#Cc1cc(F)cc(Oc2ccc3c4c2C(F)C(F)(F)C4(O)C(F)(F)C3(F)F)c1]

Step 1: ethyl 2,2-difluoro-2-(2,2,3,3,6-pentafluoro-1-hydroxy-2,3-dihydro-1H-inden-1-yl)acetate

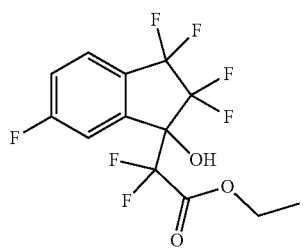 [SMILES: CCOC(=O)C(F)(F)C1(O)c2cc(F)ccc2C(F)(F)C1(F)F]

A mixture of 2,2,3,3,6-pentafluoro-2,3-dihydro-1H-inden-1-one (10.0 g, 45.02 mmol, 1.00 equiv.), In (7.7 g, 67.06 mmol, 1.5 equiv.) and ethyl 2-bromo-2,2-difluoroacetate (13.7 g, 67.5 mmol, 1.50 equiv.) in THF (150 mL) was stirred for 16 h at 60° C. under N$_2$ atmosphere. The reaction was quenched with aqueous HCl (2.0 M, 50 mL) at room temperature and the resulting mixture was extracted with ethyl acetate. The combined organic layers were dried over anhydrous Na$_2$SO$_4$. After filtration, the filtrate was concentrated under reduced pressure. The residue was purified by silica gel column chromatography, eluted with PE/EA (5/1), to afford the title compound (8.0 g, 51.3%) as a light-yellow oil. MS (ES, m/z): [M−1]$^-$=345.0

Step 2: 1,1,2,2,3,3,5-heptafluoro-2a-hydroxy-1,2,2a,
3-tetrahydro-4H-cyclopenta[cd]inden-4-one

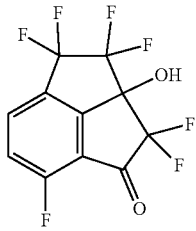 [SMILES: O=C1c2c(F)ccc3c2C(O)(C1(F)F)C(F)(F)C3(F)F]

To a stirred solution of ethyl 2,2-difluoro-2-(2,2,3,3,6-pentafluoro-1-hydroxy-2,3-dihydro-1H-inden-1-yl)acetate (500 mg, 1.44 mmol, 1.00 equiv.) in THF (10 mL) was added LDA (2.2 mL, 4.40 mmol, 2.0 M, 3.06 equiv.) dropwise at −78° C. under N₂ atmosphere. The resulting mixture was stirred for 1 h at −78° C. and then quenched with saturated aqueous NH₄Cl (10 mL) at −78° C. The resulting mixture was extracted with ethyl acetate and the combined organic layers were dried over anhydrous Na₂SO₄. After filtration, the filtrate was concentrated and purified by silica gel column chromatography, eluted with PE/EA (3/1), to afford crude product. The crude product was purified by Prep-HPLC to afford the title product (34 mg, 7.8%) as a light-yellow oil. MS (ES, m/z): [M−1]⁻=298.9

Step 3: 3-fluoro-5-((1,1,2,2,3,3-hexafluoro-2a-hydroxy-4-oxo-2,2a,3,4-tetrahydro-1H-cyclopenta[cd]inden-5-yl)oxy)benzonitrile

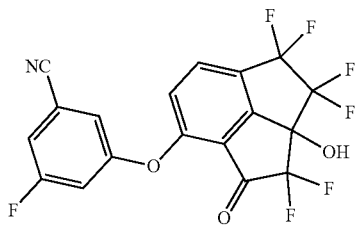 [SMILES: N#Cc1cc(F)cc(Oc2ccc3c4c2C(=O)C(F)(F)C4(O)C(F)(F)C3(F)F)c1]

A mixture of 1,1,2,2,3,3,5-heptafluoro-2a-hydroxy-1,2,2a,3-tetrahydro-4H-cyclopenta-[cd]inden-4-one (100 mg, 0.33 mmol, 1.00 equiv.), Cs₂CO₃ (217 mg, 0.67 mmol, 2.00 equiv.) and 3-fluoro-5-hydroxybenzonitrile (50 mg, 0.36 mmol, 1.10 equiv.) in DMF (2 mL) was stirred for 1 h at −10° C. under N₂ atmosphere. The crude reaction mixture was used for next step directly without further purification. MS (ES, m/z): [M−1]⁻=416.0.

Step 4: 3-fluoro-5-((1,1,2,2,3,3-hexafluoro-2a,4-dihydroxy-2,2a,3,4-tetrahydro-1H-cyclopenta[cd]inden-5-yl)oxy)benzonitrile To a stirred solution of crude 3-fluoro-5-((1,1,2,2,3,3-hexafluoro-2a-hydroxy-4-oxo-2,2a,3,4-tetrahydro-1H-cyclopenta[cd]inden-5-yl)oxy)benzonitrile (0.33 mmol, 1.00 equiv.) in MeOH (2 mL) was added NaBH₄ (25 mg, 0.66 mmol, 2.00 equiv.) in portions at −10° C. under N₂ atmosphere. The resulting mixture was stirred for 1 h at −10° C. and then quenched with saturated aqueous NH₄Cl solution. The resulting mixture was extracted with ethyl acetate and the combined organic layers were washed with brine, and dried over anhydrous Na₂SO₄. After filtration, the filtrate was concentrated under reduced pressure. The residue was purified by silica gel column chromatography, eluted with PE/EA (3/1), to afford the title compound (90 mg, 63.6%) for two steps as a light-yellow oil. MS (ES, m/z): [M−1]⁻=418.0.

Step 5: 3-fluoro-5-((1,1,2,2,3,3,4-heptafluoro-2a-hydroxy-2,2a,3,4-tetrahydro-1H-cyclopenta[cd]inden-5-yl)oxy)benzonitrile To a stirred solution of 3-fluoro-5-((1,1,2,2,3,3-hexafluoro-2a,4-dihydroxy-2,2a,3,4-tetrahydro-1H-cyclopenta[cd]inden-5-yl)oxy)benzonitrile (50 mg, 0.12 mmol, 1.00 equiv.) in DCM (1.0 mL) was added DAST (38 mg, 0.24 mmol, 2.00 equiv.) dropwise at −20° C. under N₂ atmosphere. The resulting mixture was stirred for 2 h at room temperature, quenched with saturated aqueous NaHCO₃ solution. The resulting mixture was extracted with DCM and the combined organic layers were dried over anhydrous Na₂SO₄. After filtration, the filtrate was concentrated under reduced pressure and the crude product was purified by Prep-HPLC to afford the title compound (14 mg, 27.5%) as a light yellow solid. MS (ES, m/z): [M−1]⁻=420.0.

Example 18

Synthesis of 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile

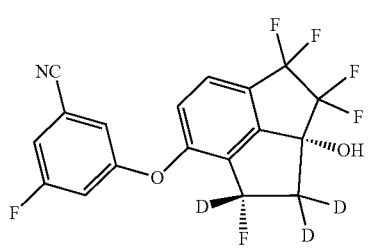 [SMILES: [2H]C1([2H])[C@@]2(O)c3c(ccc(Oc4cc(F)cc(C#N)c4)c3[C@@]1([2H])F)C(F)(F)C2(F)F]

Step 1: (R)-1-allyl-2,2,3,3,6-pentafluoro-2,3-dihydro-1H-inden-1-ol

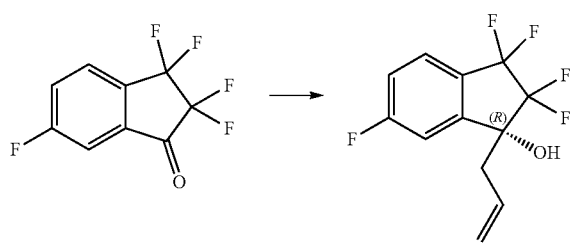

To a stirred solution of t-BuONa (21.6 mg, 0.225 mmol, 0.10 equiv.) in toluene (3.0 mL) were added a solution of (S)-2-((3-(tert-butyl)-2-hydroxybenzyl)amino)-N,N,3-trimethylbutanamide (275.8 mg, 0.90 mmol, 0.40 equiv.) in toluene (0.5 mL), then a solution of MeOH (90.2 mg, 2.8 mmol, 1.25 equiv.) in toluene (0.5 mL), followed by a solution of 2,2,3,3,6-pentafluoro-2,3-dihydro-1H-inden-1-one (0.50 g, 2.25 mmol, 1.00 equiv.) in toluene (0.5 mL). After stirring for 15 min at room temperature, a solution of 4,4,5,5-tetramethyl-2-(prop-2-en-1-yl)-1,3,2-dioxaborolane (416.1 mg, 2.48 mmol, 1.10 equiv.) in toluene (0.5 mL) was added slowly. The resulting mixture was stirred for 6.5 h at 60° C., cooled and diluted with ethyl acetate. After separation, the organic layer was washed with water and brine, dried over Na$_2$SO$_4$. After filtration, the filtrate was concentrated and purified by silica gel column chromatography, eluted with DCM/PE (0-40%), to afford the title compound (0.52 g, 87.4%) as a light yellow oil. MS (ES, m/z): [M−1]$^-$=263.0.

Step 2: (1R)-7-bromo-2,2,3,3,6-pentafluoro-1-(prop-2-en-1-yl)inden-1-ol

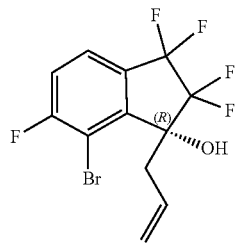

To a stirred solution of (R)-1-allyl-2,2,3,3,6-pentafluoro-2,3-dihydro-1H-inden-1-ol (5.0 g, 18.93 mmol, 1.00 equiv.) in tetrahydrofuran (60 mL) was added 2.0 M LDA (28.4 mL, 56.8 mmol, 3.0 equiv.) dropwise at −40° C. under nitrogen atmosphere. After stirring for 1 h at −40° C., a solution of carbon tetrabromide (7.53 g, 22.71 mmol, 1.20 equiv.) in THF was added dropwise at −40° C. The resulting mixture was stirred for additional 10 min at −40° C., then quenched with 1.0 M HCl(aq.) (100 mL) at −40° C. The resulting mixture was extracted with MTBE. The organic layer was washed with water and brine, dried over anhydrous Na$_2$SO$_4$. After filtration, the filtrate was concentrated and purified by silica gel column chromatography, eluted with EtOAc/PE (0-30%), to afford the crude product as light yellow oil. This crude product was further purified by reversed-phase C18 silica gel column (mobile phase, ACN in water, 50% to 95% gradient in 12 min) to afford the title compound (3.5 g, 53.9%) as a light yellow oil. MS (ES, m/z): [M−1]$^-$=340.9.

Step 3: (R)-3,3,4,4,7-pentafluoro-1-methylene-1,2,3,4-tetrahydro-2aH-cyclopenta[cd]inden-2a-ol

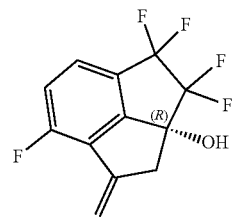

To a stirred mixture of (R)-1-allyl-7-bromo-2,2,3,3,6-pentafluoro-2,3-dihydro-1H-inden-1-ol (3.50 g, 10.20 mmol, 1.00 equiv.) in DMF (5.0 mL) were added AcONa (2.51 g, 30.60 mmol, 3.00 equiv.) and Pd(dppf)Cl$_2$.CH$_2$Cl$_2$ (0.83 g, 1.02 mmol, 0.10 equiv.) at room temperature under nitrogen atmosphere. The resulting mixture was stirred for 3 h at 100° C. under nitrogen atmosphere, cooled and diluted with water, then extracted with ethyl acetate. The organic layer was washed with water and brine, dried over anhydrous Na$_2$SO$_4$. After filtration, the filtrate was concentrated and purified by silica gel column chromatography, eluted with EtOAc/PE (0-40%), to afford the title compound (2.0 g, 74.8%) as a light yellow solid. MS (ES, m/z): [M−1]$^-$=260.9.

Step 4: (R)-3,3,4,4,7-pentafluoro-2a-hydroxy-2,2a,3,4-tetrahydro-1H-cyclopenta[cd]inden-1-one

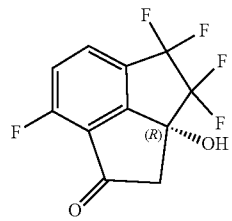

To a stirred mixture of (R)-3,3,4,4,7-pentafluoro-1-methylene-1,2,3,4-tetrahydro-2aH-cyclopenta[cd] inden-2a-ol (2.00 g, 7.63 mmol, 1.00 equiv.) in a mixed solvents (DCM/MeCN/H$_2$O=1/1/1.5, 70.0 mL) was added RuCl$_3$.H$_2$O (86.0 mg, 0.38 mmol, 0.05 equiv.) at room temperature. To the resulting mixture was added NaIO$_4$ (6.53 g, 30.53 mmol, 4.0 equiv.) in portions at room temperature. After stirring for 1 h at room temperature, the reaction mixture was diluted with water, then extracted with DCM. The organic layer was washed with saturated Na$_2$S$_2$O$_3$ (aq.), water and brine, dried over anhydrous Na$_2$SO$_4$. After filtration, the filtrate was concentrated to afford crude title compound (1.85 g, 91.8%) as a light yellow solid, which was used for next step without further purification. MS (ES, m/z): [M−1]$^-$=262.9.

Step 5: (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile

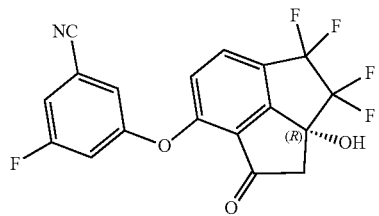

To a stirred solution of (R)-3,3,4,4,7-pentafluoro-2a-hydroxy-2,2a,3,4-tetrahydro-1H-cyclopenta[cd] inden-1-one (1.85 g, 7.0 mmol, 1.00 equiv.) and 3-fluoro-5-hydroxybenzonitrile (0.86 g, 6.30 mmol, 0.90 equiv.) in DMF (20.0 mL) was added Cs$_2$CO$_3$ (2.28 g, 7.00 mmol, 1.00 equiv.) at room temperature. After stirring for 16 h at room temperature, the reaction mixture was quenched with water at 0° C., then extracted with EtOAc. The organic layer was washed with water and brine, dried over anhydrous Na$_2$SO$_4$. After filtration, the filtrate was concentrated and purified by silica gel column chromatography, eluted with EtOAc/PE (0-40%), to afford the title compound (1.95 g, 73.0%) as a white solid. MS (ES, m/z): [M−1]$^-$=380.1.

Step 6: (R)-3-fluoro-5-((3,3,4,4-tetrafluoro-2a-hydroxy-1-oxo-2,2a,3,4-tetrahydro-1H-cyclopenta[cd]inden-7-yl-2,2-d2)oxy)benzonitrile

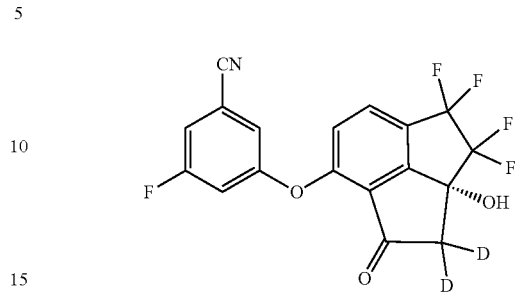

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile (3.0 g, 7.87 mmol, 1.00 equiv.) in THF (60 mL) was added a solution of NaOD (645 mg, 15.737 mmol, 2.00 equiv.) in D$_2$O (24 mL) dropwise at room temperature. The resulting mixture was stirred for 4 h at room temperature then diluted with D$_2$O and extracted with MTBE. The combined organic layers were dried over anhydrous Na$_2$SO$_4$. After filtration, the filtrate was concentrated under reduced pressure and the residue was purified by silica gel column chromatography, eluted with PE/EA (3:1), to afford the title compound (2.3 g, 76.3%) as a white solid. MS (ES, m/z): [M−H]$^-$=382.1.

Step 7: 3-fluoro-5-(((1R,2aR)-3,3,4,4-tetrafluoro-1,2a-dihydroxy-2,2a,3,4-tetrahydro-1H-cyclopenta[cd]inden-7-yl-1,2,2-d3)oxy)benzonitrile

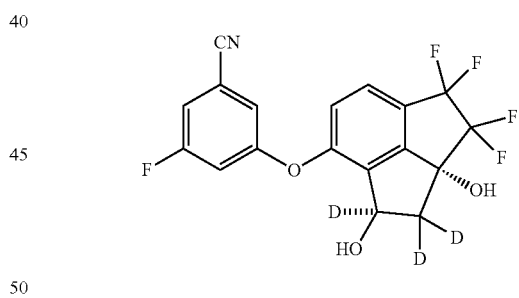

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl-2,2-d2)oxy)benzonitrile (1.5 g, 3.883 mmol, 1.00 equiv.) in CD$_3$OD (15 mL) was added NaBD$_4$ (329 mg, 7.827 mmol, 2.00 equiv.) at 5° C. The resulting mixture was stirred for 2 h at room temperature then quenched with D$_2$O at room temperature. The resulting mixture was extracted with MTBE and the combined organic layers were dried over anhydrous Na$_2$SO$_4$. After filtration, the filtrate was concentrated under reduced pressure and the residue was purified by silica gel column chromatography, eluted with PE/EA (3:1), to afford the title compound (1.5 g, 99.2%) as a light yellow solid. MS (ES, m/z): [M−H]$^-$=385.1.

Step 8: 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile

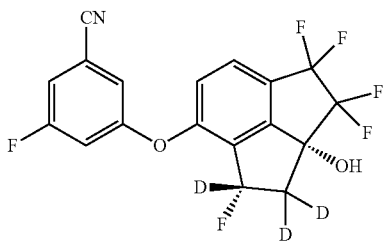 [SMILES: [2H]C1([2H])[C@@]2(O)c3c(ccc(Oc4cc(F)cc(C#N)c4)c3[C@@]1([2H])F)C(F)(F)C2(F)F]

To a stirred mixture of 3-fluoro-5-(((1R,2aR)-3,3,4,4-tetrafluoro-1,2a-dihydroxy-2,2a,3,4-tetrahydro-1H-cyclopenta[cd]inden-7-yl-1,2,2-d3)oxy)benzonitrile (1.5 g, 3.88 mmol, 1.00 equiv.) in THF (21 mL) were added DBU (1.18 g, 7.77 mmol, 2.00 equiv.) and pyridine-2-sulfonyl fluoride (814 mg, 5.05 mmol, 1.30 equiv.) in THF (2 mL) dropwise at room temperature under nitrogen atmosphere. The resulting mixture was stirred for 16 h at room temperature under nitrogen atmosphere then concentrated under reduced pressure. The residue was purified by silica gel column chromatography with PE/EA (4:1). The resulting product was further purified by chiral Prep-HPLC to afford the optical pure title compound (740 mg, 49.1%) as a white solid. MS (ES, m/z): [M−H]⁻=387.1.

Example 19

Synthesis of 3-fluoro-5-(((1S,2aR)-1,3,3,4,4-pentafluoro-2a-hydroxy-2,2a,3,4-tetrahydro-1H-cyclopenta [cd]inden-7-yl-1-d)oxy)benzonitrile-2,4,6-d₃

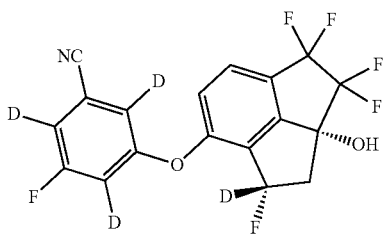 [SMILES: [2H]c1c(F)c([2H])c(Oc2ccc3c4c2[C@@]([2H])(F)C[C@]4(O)C(F)(F)C3(F)F)c([2H])c1C#N]

Step 1: 3-bromo-5-fluorophen-2,4,6-d₃-ol

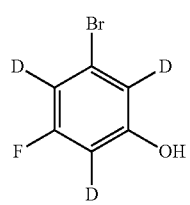 [SMILES: [2H]c1c(O)c([2H])c(Br)c([2H])c1F]

Into a 40 mL sealed tube were added 3-bromo-5-fluorophenol (5.00 g, 26.18 mmol, 1.00 equiv.) and 60% D₂SO₄ (13.09 g, 78.53 mmol, 3.00 equiv.) in D₂O at room temperature. The resulting mixture was stirred for 18 h at 75° C. then poured slowly onto ice. The resulting mixture was extracted with EtOAc and the combined organic layers were washed with water, brine and dried over anhydrous Na₂SO₄. After filtration, the filtrate was concentrated under reduced pressure to give the product. The product was added in 60% D₂SO₄ in D₂O, and the above procedure was repeated for additional 4 times to give the tittle compound (4.20 g, 82.7% yield) as yellow oil. MS (ES, m/z): [M−H]⁻=191.9.

Step 2: 3-fluoro-5-hydroxybenzonitrile-2,4,6-d₃

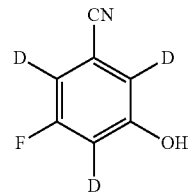

To a stirred solution of 3-bromo-5-fluorophen-2,4,6-d₃-ol (100 mg, 0.515 mmol, 1.00 equiv.) and Zn(CN)₂ (121 mg, 1.03 mmol, 2.0 equiv.) in DMF (2.0 mL) was added Pd(PPh₃)₄ (60 mg, 0.05 mmol, 0.10 equiv.) at room temperature under nitrogen atmosphere. The resulting mixture was stirred for 3 h at 100° C. under nitrogen atmosphere and then quenched with water at room temperature. The resulting mixture was extracted with EtOAc and the combined organic layers were washed with water, brine, and dried over anhydrous Na₂SO₄. After filtration, the filtrate was concentrated under reduced pressure. The residue was purified by silica gel column chromatography, eluted with PE/EtOAc (1:1), to afford the title compound (37 mg, 51.2%) as a white solid. MS (ES, m/z): [M−H]⁻=139.0.

Step 3: (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile-2,4,6-d₃

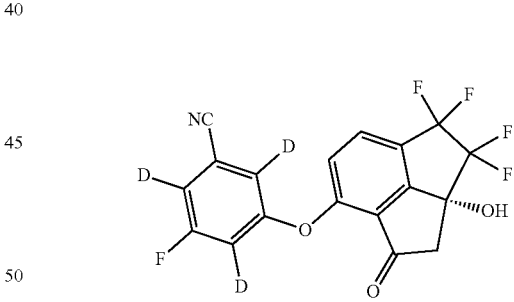

To a stirred mixture of (R)-3,3,4,4,7-pentafluoro-2a-hydroxy-2,2a,3,4-tetrahydro-1H-cyclopenta[cd]inden-1-one (179 mg, 0.68 mmol, 1.00 equiv.) and 3-fluoro-5-hydroxybenzonitrile-2,4,6-d₃ (95 mg, 0.68 mmol, 1.00 equiv.) in DMF (3.5 mL) was added Cs₂CO₃ (221 mg, 0.68 mmol, 1.00 equiv.) at room temperature. After stirring for 16 h at room temperature, the reaction mixture was quenched with water at 0° C. The resulting mixture was extracted with EtOAc and the combined organic layers were washed with H₂O, brine and dried over anhydrous Na₂SO₄. After filtration, the filtrate was concentrated under reduced pressure. The residue was purified by silica gel column chromatography, eluted with EtOAc/PE (0-40%), to afford the tittle compound (170 mg, 65.3%) as a white solid. MS (ES, m/z): [M−H]⁻=383.0.

Step 4: 3-fluoro-5-(((1R,2aR)-3,3,4,4-tetrafluoro-1,
2a-dihydroxy-2,2a,3,4-tetrahydro-1H-cyclopenta[cd]
inden-7-yl-1-d)oxy)benzonitrile-2,4,6-d₃

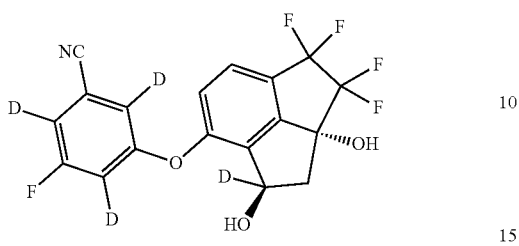

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile-2,4,6-d₃ (170 mg, 0.442 mmol, 1.00 equiv.) in CD₃OD (3.5 mL) was added NaBD₄ (37 mg, 0.885 mmol, 2.00 equiv.) in portions at room temperature. The resulting mixture was stirred for 3 h at room temperature, diluted with D₂O (3.0 mL) and extracted with EtOAc. The combined organic layers were dried over anhydrous Na₂SO₄, and filtered. The filtrate was concentrated and the residue was purified by silica gel column chromatography, eluted with EtOAc/PE (0-40%), to afford the tittle compound (120 mg, 70.0%) as a white solid. MS (ES, m/z): [2M−H]⁻=773.1.

Step 5: 3-fluoro-5-(((1S,2aR)-1,3,3,4,4-pentafluoro-
2a-hydroxy-2,2a,3,4-tetrahydro-1H-cyclopenta[cd]
inden-7-yl-1-d)oxy)benzonitrile-2,4,6-d₃

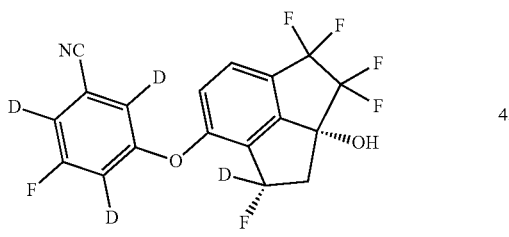

To a stirred mixture of 3-fluoro-5-(((1R,2aR)-3,3,4,4-tetrafluoro-1,2a-dihydroxy-2,2a,3,4-tetrahydro-1H-cyclopenta[cd]inden-7-yl-1-d)oxy)benzonitrile-2,4,6-d₃ (125 mg, 0.32 mmol, 1.00 equiv.) in THF (1.6 mL) were added DBU (98 mg, 0.65 mmol, 2.00 equiv.) and pyridine-2-sulfonyl fluoride (68 mg, 0.42 mmol, 1.30 equiv.) in THF (0.4 mL) dropwise at room temperature under nitrogen atmosphere. The resulting mixture was stirred for 16 h at room temperature under nitrogen atmosphere. The reaction solution was purified by silica gel column chromatography, eluted with PE/EtOAc (4:1), followed by purification with prep-HPLC to afford the tittle compound (10 mg, 8.0%) as a white solid. MS (ES, m/z): [M−H]⁻=388.1.

Example 20

Synthesis of (R)-3-fluoro-5-((3,3,4,4-tetrafluoro-2a-
hydroxy-1-methylene-2,2a,3,4-tetrahydro-1H-cyclo-
penta [cd]inden-7-yl)oxy)benzonitrile [23a] and
(S)-3-fluoro-5-((3,3,4,4-tetrafluoro-2a-hydroxy-1-
methylene-2,2a,3,4-tetrahydro-1H-cyclopenta[cd]
inden-7-yl)oxy)benzonitrile [23b]

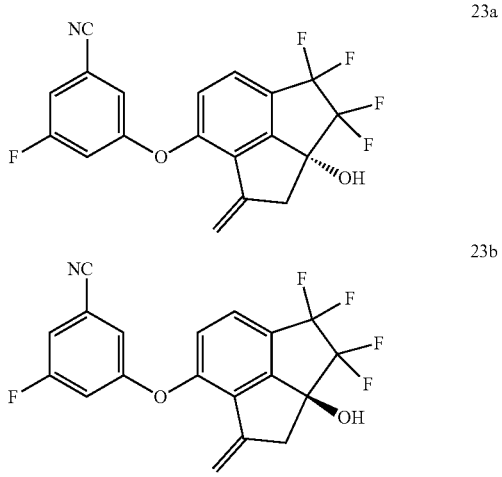

To a stirred mixture of (R)-3,3,4,4,7-pentafluoro-1-methylene-1,2,3,4-tetrahydro-2aH-cyclopenta[cd]inden-2a-ol (400 mg, 1.53 mmol, 1.0 equiv, ~80% ee) and 3-fluoro-5-hydroxybenzonitrile (209 mg, 1.53 mmol, 1.0 equiv) in DMF (10 mL) was added Cs₂CO₃ (497 mg, 1.53 mmol, 1.0 equiv) at room temperature and the resulting mixture was stirred for 24 h at 100° C. After cooling the reaction mixture to room temperature, it was filtered. The filtrate was purified by Prep-HPLC to afford 131 mg of product as a mixture of enantiomers. The enantiomers were separated by Chiral pre-HPLC [Column: CHIRALPAK OD-3, 50*4.6 mm, 3 um OD30CC-QE001, flow rate: 1.0 mL/min; oven temperature: 25° C.; Mobile Phase A: n-hexanes; Mobile Phase B: ethanol; conc. of Phase B: 10%) to afford 23a (65 mg, 11.2%) MS (ES, m/z): [M−H]⁻=378.0. tR: 1.34 min and 23b (6 mg, 1.0%); MS (ES, m/z): [M−H]⁻=378.0. tR: 1.77 min.

Example 21

Synthesis of 3-fluoro-5-(((1R,2S,2aS)-1,2,3,3,4,4-
hexafluoro-2a-hydroxy-2,2a,3,4-tetrahydro-1H-cy-
clopenta[cd] inden-7-yl)oxy)benzonitrile [24a] and
3-fluoro-5-(((1R,2R,2aS)-1,2,3,3,4,4-hexafluoro-2a-
hydroxy-2,2a,3,4-tetrahydro-1H-cyclopenta[cd]
inden-7-yl)oxy)benzonitrile [24b]

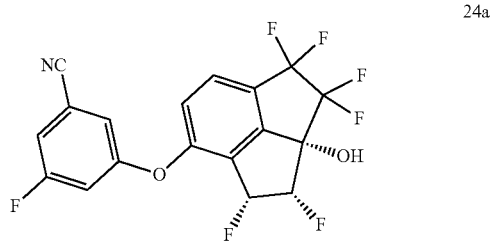

-continued

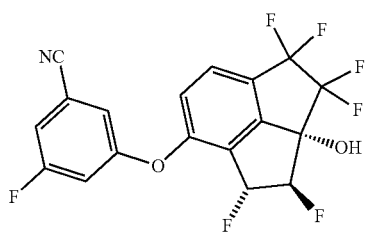

24b

Step 1: (R)-3-((4-(butylimino)-1,1,2,2-tetrafluoro-2a-hydroxy-2,2a,3,4-tetrahydro-1H-cyclopenta[cd]inden-5-yl)oxy)-5-fluorobenzonitrile

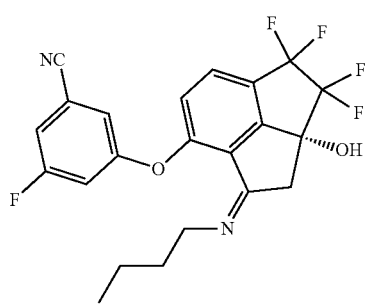 [SMILES: CCCC/N=C1/C[C@@]2(O)c3c(ccc(Oc4cc(F)cc(C#N)c4)c31)C(F)(F)C2(F)F]

A solution of (R)-3-fluoro-5-((1,1,2,2-tetrafluoro-2a-hydroxy-4-oxo-2,2a,3,4-tetrahydro-1H-cyclopenta[cd] inden-5-yl)oxy)benzonitrile (700 mg, 1.84 mmol, 1.0 equiv., ~80% ee), TFA (42 mg, 0.37 mmol, 0.2 equiv.) and butylamine (1343 mg, 18.36 mmol, 10.0 equiv.) in toluene (15 mL) was stirred for 16 h at 100° C. under $N_2$ atmosphere. The resulting mixture was concentrated under vacuum to afford the title compound (1.0 g, crude) as a light brown oil, which was used for next step directly. MS (ES, m/z): $[M+1]^+$ =437.2.

Step 2: 3-fluoro-5-(((2aS,3S)-1,1,2,2,3-pentafluoro-2a-hydroxy-4-oxo-2,2a,3,4-tetrahydro-1H-cyclopenta[cd] inden-5-yl)oxy)benzonitrile and 3-fluoro-5-(((2aS,3R)-1,1,2,2,3-pentafluoro-2a-hydroxy-4-oxo-2,2a,3,4-tetrahydro-1H-cyclopenta[cd]inden-5-yl)oxy)benzonitrile

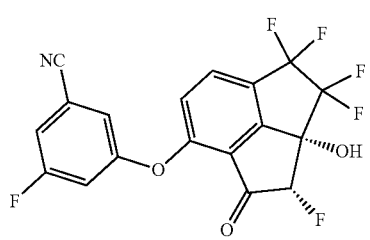

-continued

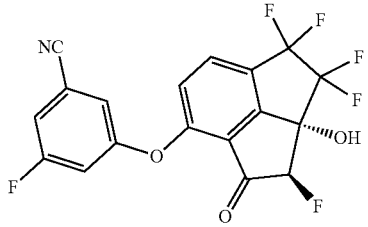

A mixture of (R)-3-((4-(butylimino)-1,1,2,2-tetrafluoro-2a-hydroxy-2,2a,3,4-tetrahydro-1H-cyclopenta [cd]inden-5-yl)oxy)-5-fluorobenzonitrile (1.0 g crude, 1.84 mmol, 1.0 equiv.), sodium sulfate (651 mg, 4.58 mmol, 2.5 equiv.) and Selectfluor (1.05 g, 2.96 mmol, 1.6 equiv.) in MeCN (15 mL) was stirred for 4 h at 60° C. under $N_2$ atmosphere. The crude product was purified by Prep-HPLC to afford 150 mg of 3-fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile and 300 mg of 3-fluoro-5-(((2aS,3R)-1,1,2,2,3-pentafluoro-2a-hydroxy-4-oxo-2,2a,3,4-tetrahydro-1H-cyclopenta[cd] inden-5-yl)oxy)benzonitrile. MS (ES, m/z): $[M-1]^-$=397.9.

Step 3: 3-fluoro-5-(((2aS,3R,4S)-1,1,2,2,3-pentafluoro-2a,4-dihydroxy-2,2a,3,4-tetrahydro-1H-cyclopenta[cd] inden-5-yl)oxy)benzonitrile

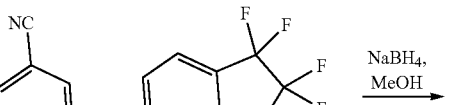

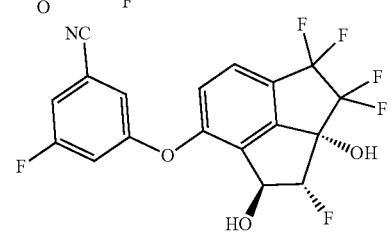

To a stirred solution of 3-fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile (100 mg, 0.25 mmol, 1.0 equiv) in MeOH (2 mL) was added $NaBH_4$ (19 mg, 0.50 mmol, 2.0 equiv) in portions at 0° C. under $N_2$ atmosphere. The resulting mixture was stirred for 1 h at room temperature under $N_2$ atmosphere and then quenched with saturated $NH_4Cl$ solution (2 mL) at rt. The resulting mixture was extracted with EtOAc. The combined organic layer was washed with brine (2×2 mL), dried over anhydrous $Na_2SO_4$, and concentrated to afford the title compound (90 mg, 90%). MS (ES, m/z): $[2M-1]^-$=801.2

Step 4: 3-fluoro-5-(((1R,2S,2aS)-1,2,3,3,4,4-hexafluoro-2a-hydroxy-2,2a,3,4-tetrahydro-1H-cyclopenta[cd] inden-7-yl)oxy)benzonitrile [24a]

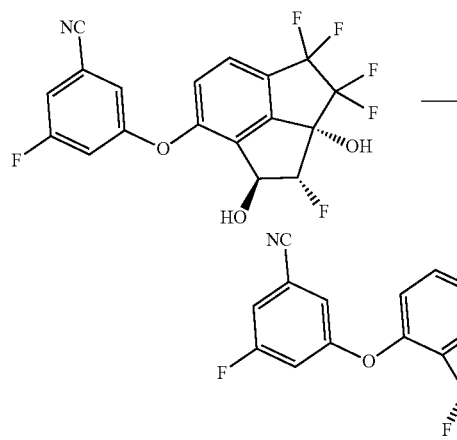

To a stirred solution of 3-fluoro-5-(((2aS,3R,4S)-1,1,2,2,3-pentafluoro-2a,4-dihydroxy-2,2a,3,4-tetrahydro-1H-cyclopenta[cd]inden-5-yl)oxy)benzonitrile (70 mg, 0.17 mmol, 1.0 equiv) in DCM (2 mL) was added DAST (42 mg, 0.26 mmol, 1.5 equiv) dropwise at −40° C. under $N_2$ atmosphere and the resulting mixture was stirred for 2 h at −40° C. under $N_2$ atmosphere. The reaction was quenched with saturated $NH_4Cl$ solution (2 mL) at room temperature and the resulting mixture was extracted with DCM. The combined organic layer was dried over anhydrous $Na_2SO_4$ and concentrated. The residue was purified by Prep-HPLC to afford the title compound (10 mg, 14%) as a light yellow solid. MS (ES, m/z): [M−1]⁻=402.0

Step 5: 3-fluoro-5-(((2aS,3S,4S)-1,1,2,2,3-pentafluoro-2a,4-dihydroxy-2,2a,3,4-tetrahydro-1H-cyclopenta[cd] inden-5-yl)oxy)benzonitrile

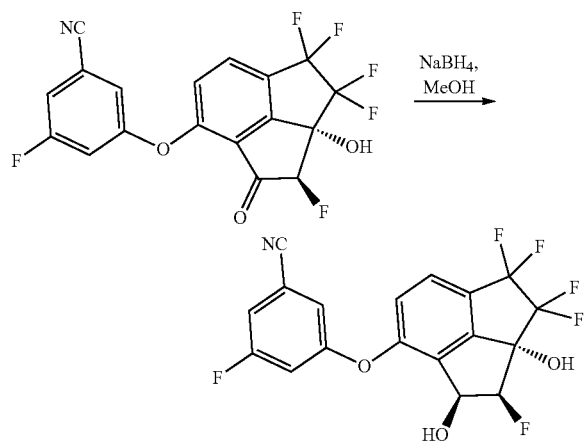

To a stirred solution of 3-fluoro-5-(((2aS,3R)-1,1,2,2,3-pentafluoro-2a-hydroxy-4-oxo-2,2a,3,4-tetrahydro-1H-cyclopenta[cd]inden-5-yl)oxy)benzonitrile (250 mg crude, 0.63 mmol, 1.0 equiv) in MeOH (3 mL) was added $NaBH_4$ (47 mg, 1.25 mmol, 2.0 equiv) in portions at 0° C. under $N_2$ atmosphere. The resulting mixture was stirred for 1.0 hour at room temperature under $N_2$ atmosphere. The reaction was quenched with saturated $NH_4Cl$ solution (2 mL) at room temperature. The resulting mixture was extracted with EtOAc. The combined organic layer was washed with brine, dried over anhydrous $Na_2SO_4$ and concentrated. The residue was purified by Prep-HPLC to afford the title compound (90 mg). MS (ES, m/z): [M−1]⁻=400.0

Step 6: 3-fluoro-5-(((1R,2R,2aS)-1,2,3,3,4,4-hexafluoro-2a-hydroxy-2,2a,3,4-tetrahydro-1H-cyclopenta[cd] inden-7-yl)oxy)benzonitrile [24b]

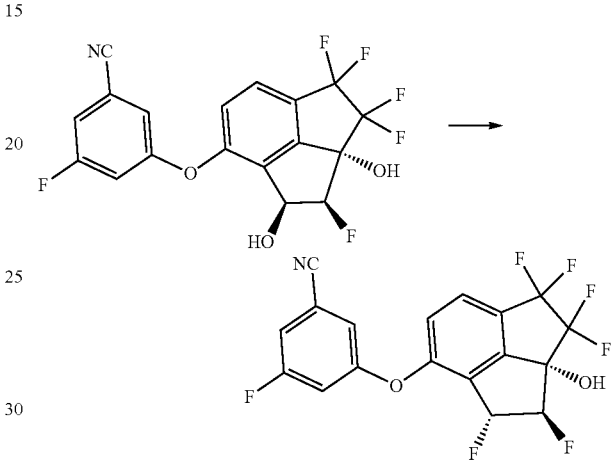

To a stirred solution of 3-fluoro-5-(((2aS,3S,4S)-1,1,2,2,3-pentafluoro-2a,4-dihydroxy-2,2a,3,4-tetrahydro-1H-cyclopenta[cd]inden-5-yl)oxy)benzonitrile (70 mg, 0.17 mmol, 1.00 equiv) in DCM (2 mL) was added DAST (42 mg, 0.26 mmol, 1.5 equiv) dropwise at −40° C. under $N_2$ atmosphere. The resulting mixture was stirred for 2 h at −40° C. under $N_2$ atmosphere. The reaction was quenched with saturated $NH_4Cl$ solution (2 mL) at room temperature. The resulting mixture was extracted with DCM. The combined organic layer was dried over anhydrous $Na_2SO_4$ and concentrated. The residue was purified by prep-HPLC to give the title compound. MS (ES, m/z): [M−1]⁻=402.1

BIOLOGICAL EXAMPLES

Example 1

VEGF ELISA Assay

The ability of the disclosed compounds to inhibit HIF-2α was measured by determining VEGF expression in 786-O cells. About 7500 786-O cells were seeded into each well of a 96-well, white, clear bottom plate (07-200-566, Fisher Scientific) with 200 ul growth medium. Four hours later, compounds were dispensed into wells by Tecan D300e digital dispenser with starting concentration of 10 uM and ½ log of dilution down to 1 nM as final concentration. Each concentration of treatment was performed in duplicate. About 20 hours later, medium was removed and fresh medium was added, followed by compounds treatment as described above. 24 hours later, cell culture medium was collected to determine VEGF concentration using an ELISA kit (R&D systems, cat #DVE00) following the manufacturer's instruction.

The EC$_{50}$ is calculated by GraphPad Prism using the dose-response-inhibition (four parameter) equation. The plate with cells was then subjected to CellTiter-Glo luminescence cell viability assay (Promega) to determine the effect of these compounds on cell numbers after the above treatment.

| Compound No. as in Cpd Table 1 | EC$_{50}$ (μM) |
|---|---|
| 1 | 0.013 |
| 4 | 0.010 |
| 5 | 0.006 |
| 7 | 2.10 |
| 8 | 0.32 |
| 9 | 0.17 |
| 10 | 0.41 |
| 11 | >5 |
| 12 | 0.10 |
| 13 | 0.33 |
| 14 | 0.63 |
| 15 | >5 |
| 19 | 4.1 |
| 21 | 0.006 |
| 23a | 0.007 |
| 24a | 0.002 |
| 24b | 0.011 |

Example 2

Co-Immunoprecipitation Assay for Inhibition of HIF-2α Dimerization

Cell Culture and Compound Treatment

Primary Pulmonary Artery Smooth Muscle Cells (PASMC, ATCC #PCS-100-023) were cultured in Vascular Cell Basal Medium (ATCC #PCS-100-030) supplemented with Vascular Smooth Muscle Cell Growth Kit (ATCC #PCS-100-042). Primary Pulmonary Artery Endothelial Cells (HPAEC, ATCC #PCS-100-022) were cultured in Vascular Cell Basal Medium (ATCC #PCS-100-030) supplemented with Endothelial Cell Growth Kit-BBE (ATCC #PCS-100-040). 0.5×10$^6$ cells were seeded into 6-well cell culture plates (Corning #3736) in 2 mL of media and cultured in a 37° C. cell culture incubator with atmospheric levels of oxygen and 5% CO$_2$ overnight. The following day, cells were cultured in normoxia condition (atmospheric levels of oxygen and 5% CO$_2$) or in hypoxia condition (1% O$_2$ and 5% CO$_2$) and treated with dimethyl sulfoxide (DMSO) or Compound 24a at 0.001, 0.01, 0.1, and 1 μM for 24 h.

Co-Immunoprecipitation Analysis of HIF and ARNT

After treatment, cells were washed with ice-cold PBS (containing compounds as in treatment step). The PBS wash was completely removed and 1 mL of ice-cold lysis buffer (#9803, Cell Signaling Tech) containing protease inhibitor and phosphatase inhibitor (#A32959, Thermo Scientific) was added to each well. Cells were then scraped off the wells and transferred to an Eppendorf tube. The sample was incubated on ice for 10 minutes and then centrifuged at 13,500 rpm (Eppendorf #5417R) at 4° C. for 15 minutes. Supernatant (cell lysate) was transferred to a new tube and protein concentration was measured by BCA protein assay. Lysates were then adjusted to same concentration by adding lysis buffer. For co-immunoprecipitation, 40 μL, of anti-human ARNT-protein A/G beads slurry (#sc-55526 AC, Santa Cruz Biotech) was added to 1 mL supernatant, followed by rotation at room temperature for 3 hr. Tubes were spun at 8,000 g for 5 minutes and supernatant was removed. Beads were then washed with cold lysis buffer for 3 times (with 5 minutes spin at 8,000 g between washes). After the last wash, as much supernatant was removed as was possible. 30 μL of loading buffer was added to the washed beads, which were then heated at 98° C. for 5 minutes. The sample was briefly spun to collect all liquid on the bottom of the tube. The supernatant was subjected to immunoblot analysis.

Cell lysates were also analyzed by immunoblot (Western analysis). For each immunoblot, an equal amount of protein samples was loaded onto SDS-PAGE gel and after electrophoresis, transferred to a nitrocellulose membrane. The membrane was incubated in 25 mL of blocking buffer (tris buffered saline (TBS) containing 0.1% Tween-20 and 5% non-fat milk) for 1 hour at room temperature. The blocked membrane was then incubated with primary antibody (1:1000 dilution, HIF-2α (D9E3 Rabbit mAb, #7098, Cell Signaling Tech), HIF1β/ARNT (D28F3 XP® Rabbit mAb, #5537, Cell Signaling Tech) and β-Tubulin (D2N5G Rabbit mAb, #15115, Cell Signaling Tech)) in 10 mL primary antibody dilution buffer (5% non-fat milk in 1×TBST) with gentle agitation overnight. Following incubation with the primary antibody, the membrane was subjected to three 5 minute washes. 15 mL of 1×TBST was used for each wash. The washed membrane was then incubated with HRP-linked secondary antibody (1:2000 dilution) in 10 mL secondary antibody dilution buffer (5% non-fat milk in 1×TBST) for 1 hour. After incubation with the secondary antibody, the membrane was subjected to three 5 minutes for each wash with 15 mL of 1×TBST. The washed membrane was incubated with 2 mL of SuperSignal West Femto Maximum Sensitivity Substrate (#P134095, Thermo Scientific) with gentle agitation for 1 minute at room temperature. The excess developing substrate was drained, and the membrane was then imaged with the Bio-Rad ChemiDoc MP imaging system.

Disruption of HIF-2α and ARNT Dimerization

As shown in FIG. 1, HIF-2α expression was very low at normoxia culture conditions and its expression was significantly enhanced under hypoxia culture conditions in both PASMC and HPAEC. Compound 24a disrupted the HIF-2α/ARNT dimerization and HIF-2α protein co-precipitated with ARNT was reduced in the lysate of cells treated with Compound 24a in a dose-dependent manner. Compound 24a at 0.01 μM could efficiently disrupt the HIF-2α/ARNT dimerization in PASMC/HPAEC under hypoxia condition.

Example 3

Combination Study of Compound 5 with Niraparib in 786-0 ccRCC Xenograft Tumor Model 786-O ccRCC cells (5×10$^6$) in 100 μL of PBS and Matrigel (1:1 ratio in volume) are inoculated subcutaneously in the right flank of each nude mouse (BALB/C) at 6-8 weeks of age for tumor development. When the xenograft tumors reach about 100-150 mm$^3$ in size, the tumor bearing mice are randomized to four groups (n=8) and treatment is started with vehicle (BID), Compound 5 (1 mg/kg, BID), niraparib (45 mg/kg, QD) or Compound 5 (1 mg/kg, BID) in combination with niraparib (45 mg/kg, QD). During the four weeks of study, tumor sizes are measured biweekly in two dimensions with a caliper and the volume is calculated using the formula V=0.5×A×B$^2$, with A and B are the long and short diameters of the tumor, respectively. Body weight of these mice are also measured biweekly. The effects of treatments on tumor growth are plotted and displayed as Mean and the standard error of the mean (SEM).

What is claimed:

1. A compound is selected from:

3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)benzonitrile according to following structure:

and 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile according to following structure:

or a pharmaceutically acceptable salt thereof.

2. The compound of claim 1, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

or a pharmaceutically acceptable salt thereof.

3. The compound of claim 2, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

4. The compound of claim 1, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl) oxy)-benzonitrile according to following structure:

or a pharmaceutically acceptable salt thereof.

5. The compound of claim 4, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl) oxy)-benzonitrile according to following structure:

6. A pharmaceutical composition comprising a compound selected from:

3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)benzonitrile according to following structure:

and 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile according to following structure:

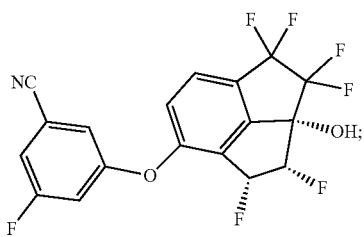 [SMILES: N#Cc1cc(F)cc(Oc2ccc3c4c2[C@@H](F)[C@@H](F)[C@]4(O)C(F)(F)C3(F)F)c1]

or
a pharmaceutically acceptable salt thereof.

7. The pharmaceutical composition of claim 6, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

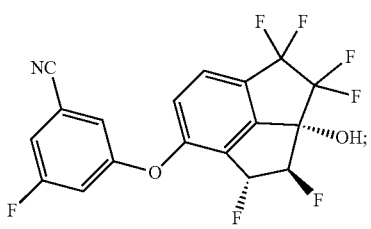 [SMILES: N#Cc1cc(F)cc(Oc2ccc3c4c2[C@@H](F)[C@H](F)[C@]4(O)C(F)(F)C3(F)F)c1]

or
a pharmaceutically acceptable salt thereof.

8. The pharmaceutical composition of claim 7, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

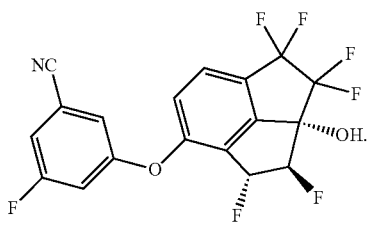 [SMILES: N#Cc1cc(F)cc(Oc2ccc3c4c2[C@@H](F)[C@H](F)[C@]4(O)C(F)(F)C3(F)F)c1]

9. The pharmaceutical composition of claim 6, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)-benzonitrile according to following structure:

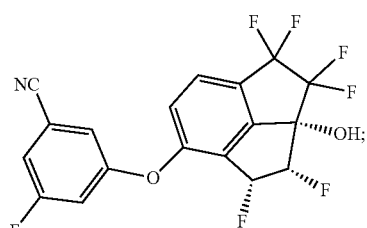

or
a pharmaceutically acceptable salt thereof.

10. The pharmaceutical composition of claim 9, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile according to following structure:

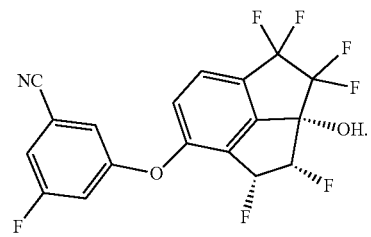 [SMILES: N#Cc1cc(F)cc(Oc2ccc3c4c2[C@@H](F)[C@@H](F)[C@]4(O)C(F)(F)C3(F)F)c1]

11. A method of treating pulmonary arterial hypertension comprising administering to a patient in need thereof, a therapeutically effective amount of a compound selected from:

3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)benzonitrile according to following structure:

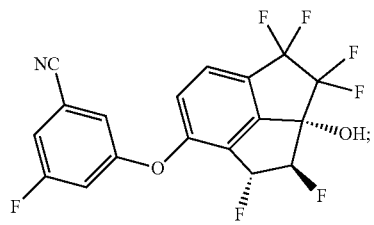

and 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile according to following structure:

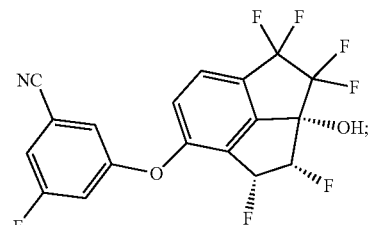

or
a pharmaceutically acceptable salt thereof, in a pharmaceutical composition comprising said compound, or a pharmaceutically acceptable salt thereof, and a pharmaceutically acceptable excipient.

12. The method of claim 11, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

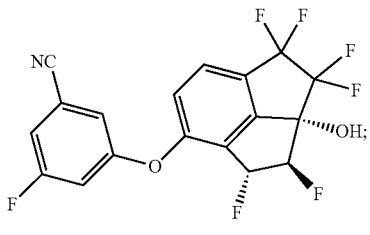

or
a pharmaceutically acceptable salt thereof.

13. The method of claim 12, wherein the compound is 3-fluoro-5-(((1R,2R,2aS)-1,2,3,3,4,4-hexafluoro-2a-hydroxy-2,2a,3,4-tetrahydro-1H-cyclopenta[cd]inden-7-yl)oxy)-benzonitrile according to following structure:

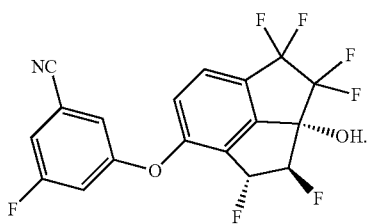 [SMILES: N#Cc1cc(F)cc(Oc2ccc3c4c2[C@@H](F)[C@H](F)[C@]4(O)C(F)(F)C3(F)F)c1]

14. The method of claim 11, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)-benzonitrile according to following structure:

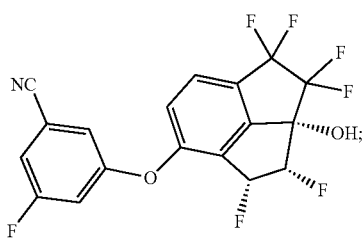

or
a pharmaceutically acceptable salt thereof.

15. The method of claim 14, wherein the compound is 3-fluoro-5-(((1R,2S,2aS)-1,2,3,3,4,4-hexafluoro-2a-hydroxy-2,2a,3,4-tetrahydro-1H-cyclopenta[cd]inden-7-yl)oxy)benzonitrile according to following structure:

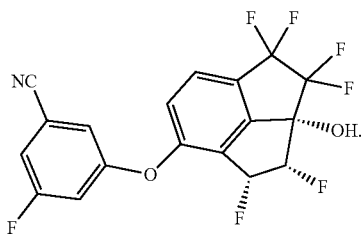 [SMILES: N#Cc1cc(F)cc(Oc2ccc3c4c2[C@@H](F)[C@@H](F)[C@]4(O)C(F)(F)C3(F)F)c1]

\* \* \* \* \*

UNITED STATES PATENT AND TRADEMARK OFFICE
CERTIFICATE OF CORRECTION

PATENT NO. : 11,420,936 B2  Page 1 of 7
APPLICATION NO. : 17/686385
DATED : August 23, 2022
INVENTOR(S) : Jiping Fu, Yan Lou and Yigang He It is certified that error appears in the above-identified patent and that said Letters Patent is hereby corrected as shown below:

In the Claims

In Column 93, Claim 1, Line 6, replace "A compound is" with --A compound--.

In Column 93, Claim 1, Line 9, insert --the-- before "following structure:".

In Column 93, Claim 1, Lines 12-20, replace " 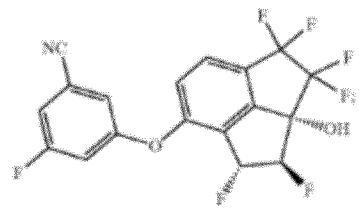 " with 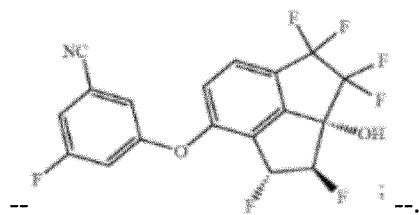 --.

In Column 93, Claim 1, Line 27, insert --the-- before "following structure:".

In Column 93, Claim 1, Lines 30-38, replace " 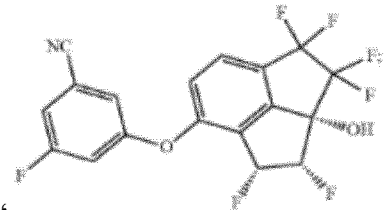 " with

Signed and Sealed this
Fifth Day of September, 2023

Katherine Kelly Vidal
*Director of the United States Patent and Trademark Office*

CERTIFICATE OF CORRECTION (continued)
U.S. Pat. No. 11,420,936 B2

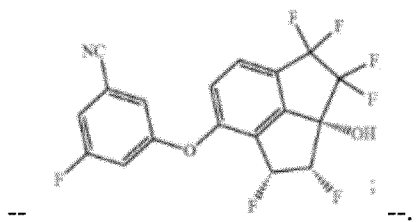
-- --.

In Column 93, Claim 2, Line 46, insert --the-- before "following structure:".

In Column 93, Claim 2, Lines 50-57, replace " 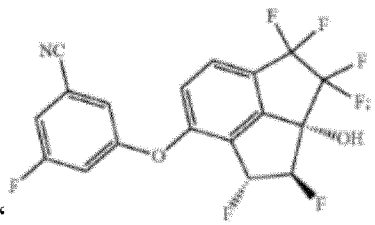 " with 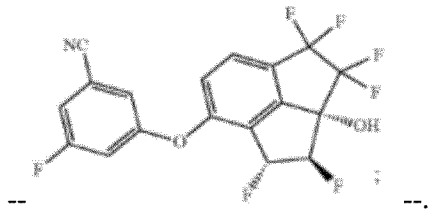 -- --.

In Column 93, Claim 3, Line 67, insert --the-- before "following structure:".

In Column 94, Claim 3, Lines 1-10, replace " 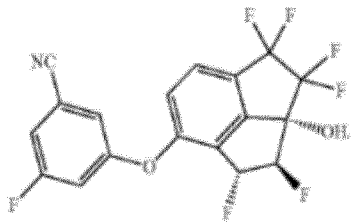 " with 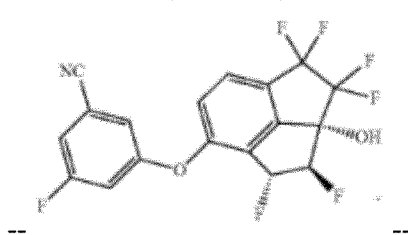 -- --.

In Column 94, Claim 4, Line 15, insert --the-- before "following structure:".

In Column 94, Claim 4, Lines 18-26, replace " 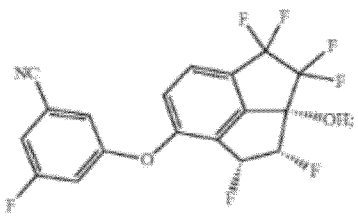 " with
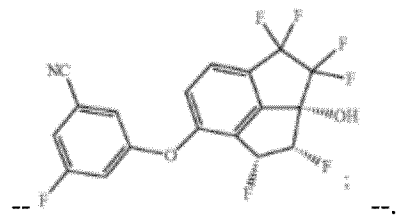
-- --.
In Column 94, Claim 5, Line 34, insert --the-- before "following structure:".
In Column 94, Claim 5, Lines 36-44, replace " 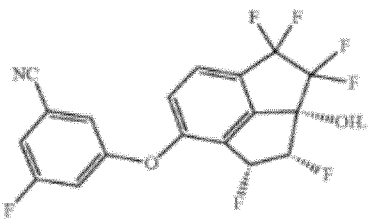 " with
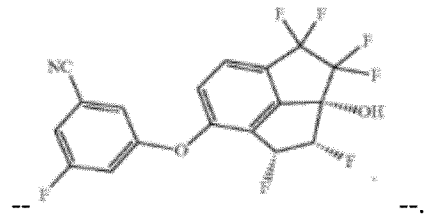
-- --.
In Column 94, Claim 6, Line 51, insert --the-- before "following structure:".
In Column 94, Claim 6, Lines 45-61, replace " 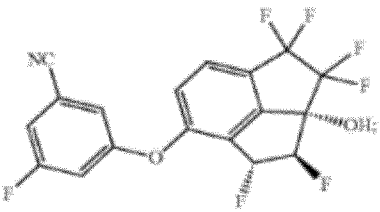 " with
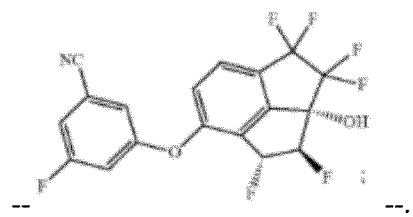
-- --.
In Column 94, Claim 6, Line 67, insert --the-- before "following structure:".

In Column 95, Claim 6, Lines 1-10, replace " 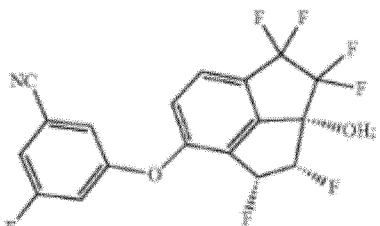 " with
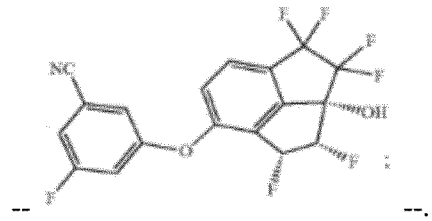 -- --.
In Column 95, Claim 7, Line 16, insert --the-- before "following structure:".
In Column 95, Claim 7, Lines 20-28, replace " 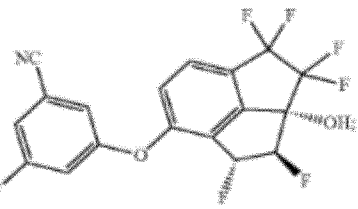 " with
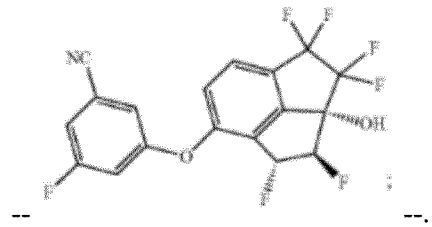 -- --.
In Column 95, Claim 8, Line 35, insert --the-- before "following structure:".
In Column 95, Claim 8, Lines 38-46, replace " 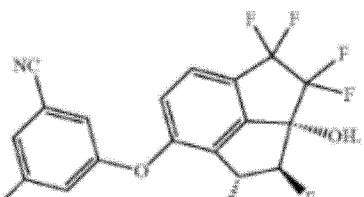 " with
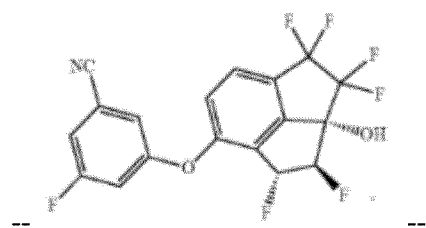 -- --.

CERTIFICATE OF CORRECTION (continued)
U.S. Pat. No. 11,420,936 B2

In Column 95, Claim 9, Line 52, insert -- the -- before "following structure:".

In Column 95, Claim 9, Lines 55-62, replace " 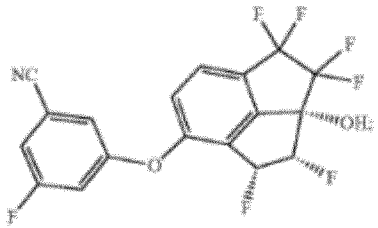 " with

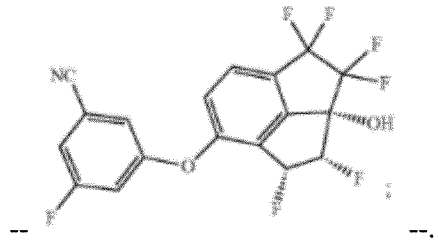

-- --.

In Column 96, Claim 10, Line 4, insert --the-- before "following structure:".

In Column 96, Claim 10, Lines 7-16, replace " 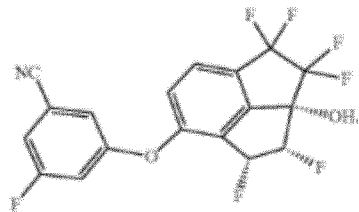 " with

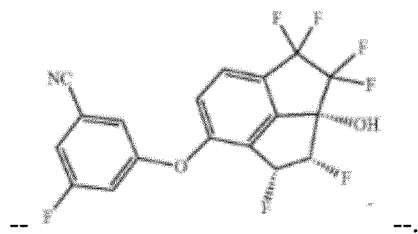

-- --.

In Column 96, Claim 11, Line 26, insert --the-- before "following structure:".

In Column 96, Claim 11, Lines 29-37, replace " 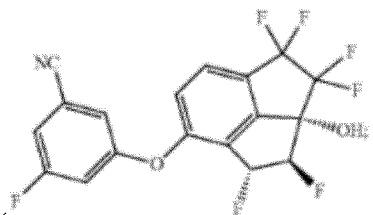 " with

CERTIFICATE OF CORRECTION (continued)
U.S. Pat. No. 11,420,936 B2

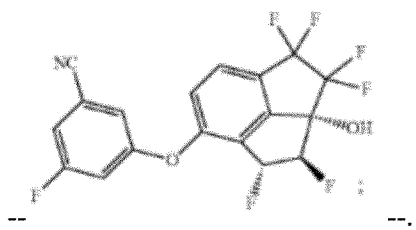

-- --.

In Column 96, Claim 11, Line 43, insert --the-- before "following structure:".

In Column 96, Claim 11, Lines 47-55, replace " 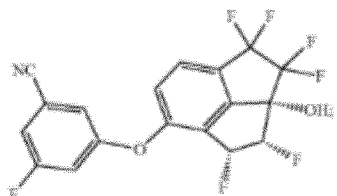 " with

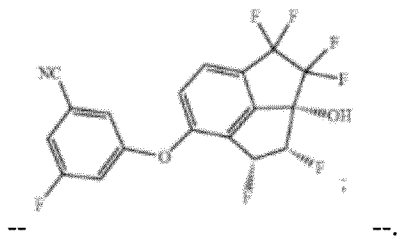

-- --.

In Column 96, Claim 12, Line 67, insert --the-- before "following structure:".

In Column 97, Claim 12, Lines 1-10, replace " 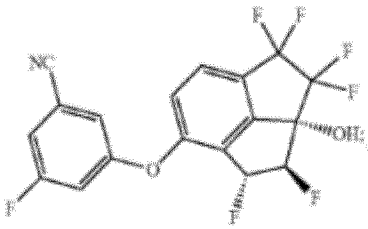 " with

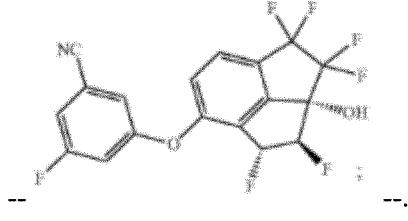

-- --.

In Column 97, Claim 13, Line 16, insert --the-- before "following structure:".

CERTIFICATE OF CORRECTION (continued)
U.S. Pat. No. 11,420,936 B2

In Column 97, Claim 13, Lines 18-26, replace " 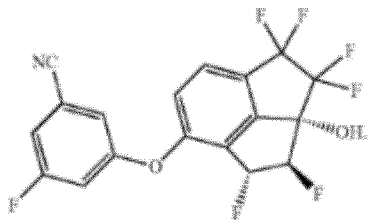 " with

-- 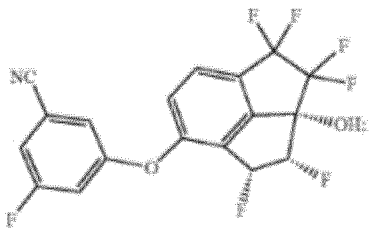 --.

In Column 97, Claim 14, Line 32, insert --the-- before "following structure:".

In Column 98, Claim 14, Lines 1-10, replace " 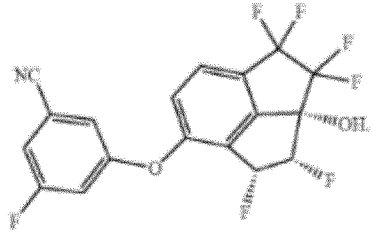 " with

-- 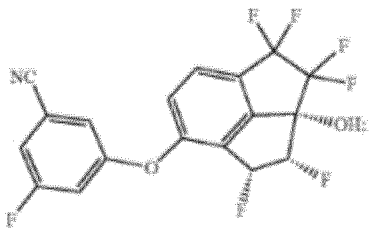 --.

In Column 98, Claim 15, Line 18, insert --the-- before "following structure:".

In Column 98, Claim 15, Lines 21-29, replace " 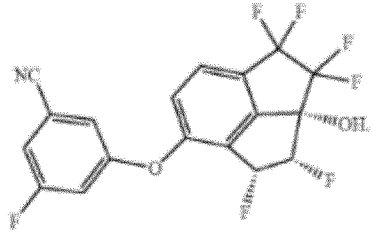 " with

-- 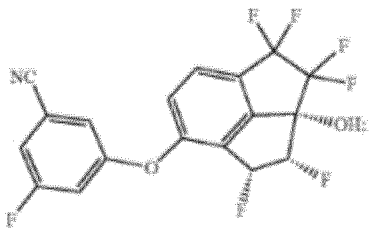 --.